(12) United States Patent
Haga et al.

(10) Patent No.: US 7,625,639 B2
(45) Date of Patent: Dec. 1, 2009

(54) METAL-COMPLEX COMPOUND AND ORGANIC ELECTROLUMINESCENCE DEVICE USING THE COMPOUND

(75) Inventors: Masa-aki Haga, Tokyo (JP); Fumio Okuda, Chiba (JP)

(73) Assignees: Idemitsu Kosan Co., Ltd., Tokyo (JP); Chuo University, Hachioji-Shi (JP)

( * ) Notice: Subject to any disclaimer, the term of this patent is extended or adjusted under 35 U.S.C. 154(b) by 505 days.

(21) Appl. No.: 11/270,500

(22) Filed: Nov. 10, 2005

(65) Prior Publication Data

US 2006/0115675 A1    Jun. 1, 2006

(30) Foreign Application Priority Data

Nov. 10, 2004    (JP)    ............................. 2004-326428
Aug. 2, 2005    (JP)    ............................. 2005-224670

(51) Int. Cl.
*H01L 51/54*    (2006.01)
*C09K 11/06*    (2006.01)

(52) U.S. Cl. ...................... 428/690; 428/917; 313/504; 313/506; 257/40; 257/102; 257/E51.044; 544/225; 546/4; 548/101; 548/103; 548/402

(58) Field of Classification Search ................ 428/690, 428/917; 313/504, 506; 257/40, E51.044; 544/225; 546/2, 4; 548/101, 103, 402, 108
See application file for complete search history.

(56) References Cited

U.S. PATENT DOCUMENTS

2001/0019782 A1 * 9/2001 Igarashi et al. .............. 428/690

FOREIGN PATENT DOCUMENTS

WO    WO 03/087258 A1    10/2003

OTHER PUBLICATIONS

Yoshikawa et al. "Electrochemical and phosphorescent properties of new mixed-ligand Ir(III) complexes with both terpyridine and various bipyridine derivatives." Analytical Sciences, 2003, vol. 19, pp. 761-765.*
Wilkinson et al. "Synthesis and luminescent of a charge-neutral, cyclometalated iridium(III) complex containing NACAN- and CANAC-coordinating terdentate ligands." Inorg. Chem. 2004, vol. 43, pp. 6513-6515.*
Patent Abstracts of Japan, JP 2001-270893, Oct. 2, 2001.
Patent Abstracts of Japan, JP 2003-147345, May 21, 2003.
Patent Abstracts of Japan, JP 2003-308978, Oct. 31, 2003 (with corresponding WO 03/087258 A1).
U.S. Appl. No. 11/269,808, Nov. 9, 2005, Haga, et al.
Tomona Yutaka, et al, "Syntheses and Properties of Emissive Iridium(III) Complexes with Tridentate Benzimidazole Derivatives", Inorganic Chemistry, vol. 44, No. 13, XP-002455102, 2005, pp. 4737-4746.
U.S. Appl. No. 11/515,777, filed Sep. 6, 2006, Haga, et al.

* cited by examiner

*Primary Examiner*—D. Lawrence Tarazano
*Assistant Examiner*—Michael Wilson
(74) *Attorney, Agent, or Firm*—Oblon, Spivak, McClelland, Maier & Neustadt, L.L.P.

(57) ABSTRACT

A metal-complex compound which comprises a tridentate chelate ligand having a specified partial structure. An organic electroluminescence device which comprises at least one organic thin film layer sandwiched between a pair of electrode consisting of an anode and a cathode, wherein the organic thin film layer comprises the metal-complex compound, which emits light by applying an electric voltage between the pair of electrode. The present invention provides an organic EL device which emits blue light with high purity and of short wavelength with an enhanced efficiency of light emission.

11 Claims, 7 Drawing Sheets

METAL-COMPLEX COMPOUND AND ORGANIC ELECTROLUMINESCENCE DEVICE USING THE COMPOUND

TECHNICAL FIELD

The present invention relates to a novel metal-complex compound and an organic electroluminescence device using the compound. Particularly, the present invention relates to an organic electroluminescence device ("electroluminescence" will be referred to as "EL", hereinafter) which emits blue light with high purity and of short wavelength, and to a metal-complex compound realizing it.

BACKGROUND ART

The organic EL devices have been expected to be applied to color wide screen image display devices replacing liquid crystal display devices, and have been intensively developed. Recently, although displays using the organic EL devices have now been used in practical applications, full-color image display devices using the same are still in the course of development because they lack in sufficient light-emitting property. In order for improving the light-emitting property, very high-efficiency green organic light-emitting devices based on electrophosphorescence employing ortho metalized iridium complex (fac-tris(2-phenylpyridine) iridium) as a phosphorus light emitting material for the organic EL device are proposed. (refer to Non-patent literatures 1 and 2 below)

Because the current organic EL devices employing the phosphorus photoluminescence are limited to emitting only green light, coverage as the color display devices is narrow. Therefore, it has been demanded to develop organic EL devices which emit light of different colors from green with improved light emission property. Regarding particularly with EL devices which emit blue light, those having an external quantum yield exceeding 5% is not reported yet. Accordingly, an improvement in the EL devices which emit blue light, if possible, enables the display devices to display full colors or white light resultantly advancing toward practical use of phosphorus light EL device greatly.

Currently, developments about a compound having Ir atom as a phosphorus photoluminescence complex are actively carried out, and Compound A below is known as a material employable for an EL device which emits green light. On the other hand, Compound B below is known as a material for an EL device which emits blue light, however, the EL device employing Compound B is not practical in view points of both lifetime and efficiency of the device. Accordingly, it is necessary to develop another complex for EL devices which emit blue light, however, any material except Compound B has not been found yet now.

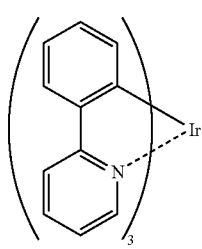

Compound A

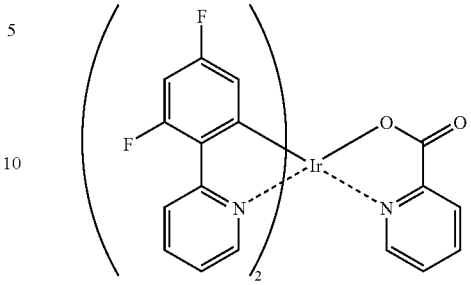

Compound B

Although the above Compounds A and B are complexes having a bidentate chelate ligand, almost no complex having a tridentate chelate ligand similar to the above compounds is known except Compound C below. (refer to Non-patent literature 3 below)

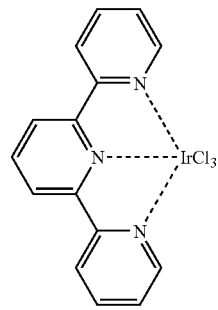

Compound C

However, Compound C serves to emit reddish light having light emission wavelength of around 600 nm, without capability of serving to emit bluish light. Accordingly a realization of a complex having a tridentate chelate ligand which serves to emit bluish light, if possible, has a possibility of new technology development.

Non-patent literature 1: D. F. O'Brien and M. A. Baldo et al. "Improved energy transfer in electrophosphorescent devices" Applied Physics letters Vol. 74 No. 3, pp 442-444, Jan. 18, 1999

Non-patent literature 2: M. A. Baldo et al. "Very high-efficiency green organic light-emitting devices based on electrophosphorescence" Applied Physics letters Vol. 75 No. 1, pp 4-6, Jul. 5, 1999

Non-patent literature 3: J-P. Collin et al, J. Am. Chem. Soc., 121,5009 (1999)

DISCLOSURE OF THE INVENTION

The present invention has been made to overcome the above problems and has an object of providing an organic EL device which emits blue light with high purity and of short wavelength, and an object of providing a metal-complex compound realizing it.

The inventors clarified a novel structural factor for enabling to emit blue light that employing a metal-complex compound with partial structure having a tridentate chelate ligand represented by a following general formula (I) or by a following general formula (II) enables to emit highly pure blue light of short wavelength and the present invention has been accomplished.

Namely, the present invention provides a metal-complex compound which comprises a tridentate chelate ligand having a partial structure represented by a following general formula (I) or by a following general formula (II).

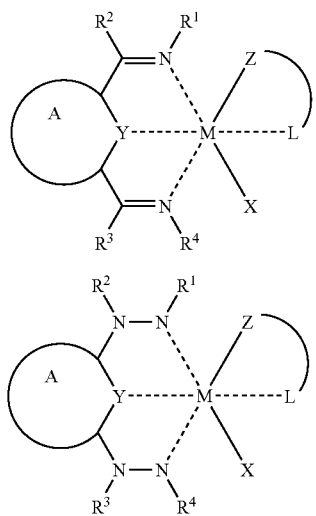

wherein M represents any one metal atom of Group 9 in Periodic Table;

L and Z each independently represents an organic group possessing any one atom of Groups 14 to 16 in Periodic Table respectively;

X represents a monovalent ligand having an atom of Groups 14 to 17 in Periodic Table;

Y represents an atom of Groups 14 to 16 in Periodic Table;

A represents a cycloalkane moiety having 5 to 20 carbon atoms and further may have a substituent, an aromatic hydrocarbon group having 6 to 20 carbon atoms and further may have a substituent or a heterocyclic group having 2 to 20 carbon atoms and further may have a substituent indicating that a circle enclosing the sign A shows a ring structure comprising Y;

$R^1$ to $R^4$ each independently represents a hydrogen atom, a cyano group, a halogen atom, an alkyl group having 1 to 12 carbon atoms and further may have a substituent, an alkylamino group having 1 to 12 carbon atoms and further may have a substituent, an arylamino group having 6 to 20 carbon atoms and further may have a substituent, an alkoxy group having 1 to 12 carbon atoms and further may have a substituent, an alkoxy halide group having 1 to 12 carbon atoms and further may have a substituent, an aryloxy group having 6 to 20 carbon atoms and further may have a substituent, an aromatic hydrocarbon group having 6 to 20 carbon atoms and further may have a substituent, a heterocyclic group having 3 to 20 carbon atoms and further may have a substituent, an alkyl halide group having 1 to 12 carbon atoms and further may have a substituent, an alkenyl group having 1 to 12 carbon atoms and further may have a substituent, an alkynyl group having 1 to 12 carbon atoms and further may have a substituent or a cycloalkyl groups having 1 to 12 carbon atoms and further may have a substituent; and $R^1$ & $R^2$ or $R^3$ & $R^4$ may bond each other to form a ring structure.

Furthers the present invention provides an organic EL device which comprises at least one organic thin film layer sandwiched between a pair of electrode consisting of an anode and a cathode, wherein the organic thin film layer comprises the above metal-complex compound, which emits light by applying an electric voltage between the pair of electrode.

The present invention provides an organic EL device which emits blue light with high purity and of short wavelength with an enhanced efficiency of light emission, and also provides a metal-complex compound realizing the EL device.

THE PREFERRED EMBODIMENT TO CARRY OUT THE INVENTION

Figure 1:
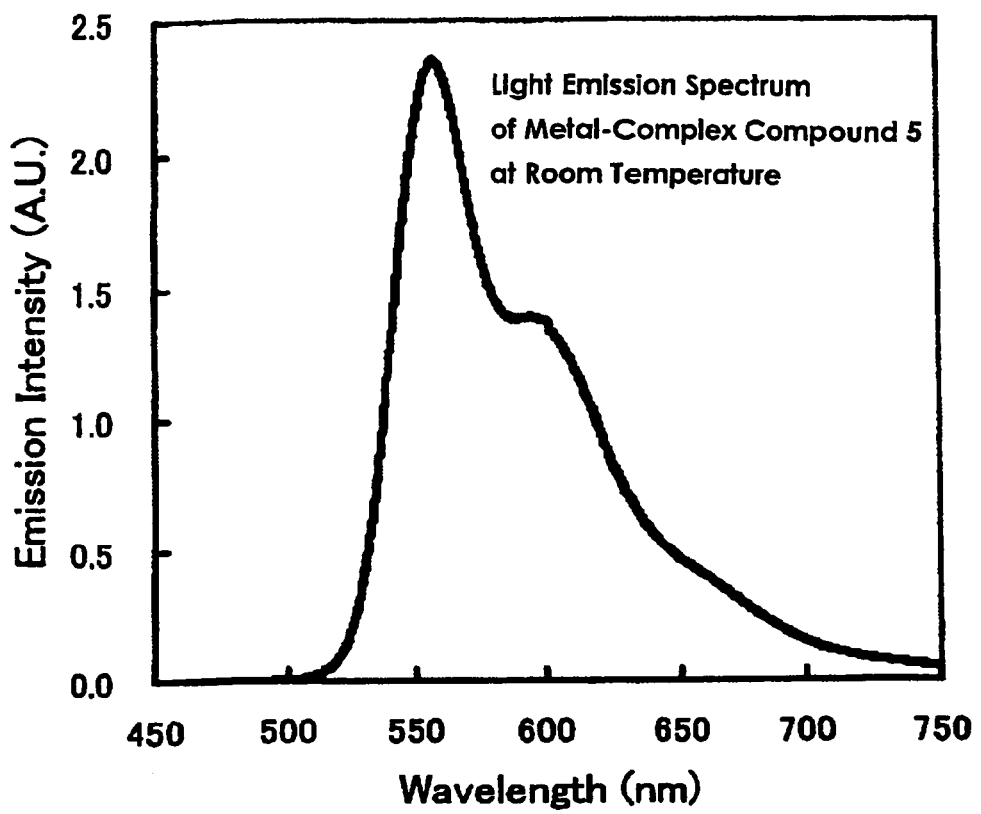
FIG. 1 is a diagram showing a light emission spectrum of Metal-Complex Compound 5 in the present invention at room temperature.

The present invention provides a metal-complex compound which comprises a tridentate chelate ligand having a partial structure represented by a following general formula (I) or by a following general formula (II):

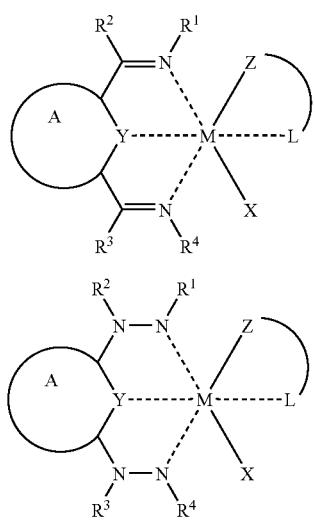

In the general formulae (I) and (II), M represents any one metal atom of Group 9 in Periodic Table, and examples include Co (cobalt) atoms, Rh (rhodium) atom, Ir (iridium) atom and 60 on while Ir being preferable.

In the general formulae (I) and (II), L and Z each independently represents an organic group possessing any one atom of Groups 14 to 16 in Periodic Table respectively;

Examples of the above atom of Groups 14 to 16 in Periodic Table possessed by L and Z include C (carbon) atom, N (nitrogen) atom, O (oxygen) atom, Si (silicon) atom, P (phosphor) atom, S (sulfur) atom, Ge (germanium) atom, As (arsenic) atom, Se (Se) atom and so on, while carbon atom, nitrogen atom and oxygen atom are preferable.

Further, the organic group represented by L and Z are preferably a hydrogen atom, a cyano group, a halogen atom, an alkyl group having 1 to 12 carbon atoms and further may have a substituent, an alkylamino group having 1 to 12 carbon atoms and further may have a substituent, an arylamino group having 6 to 20 carbon atoms and further may have a substituent, an alkoxy group having 1 to 12 carbon atoms and further may have a substituent, an alkoxy halide group having 1 to 12 carbon atoms and further may have a substituent, an aryloxy group having 6 to 20 carbon atoms and further may have a substituent, an aromatic hydrocarbon group having 6 to 20 carbon atoms and further may have a substituent, a heterocyclic group having 3 to 20 carbon atoms and further may have a substituent, an alkyl halide group having 1 to 12 carbon atoms and further may have a substituent, an alkenyl group having 1 to 12 carbon atoms and further may have a substituent, an alkynyl group having 1 to 12 carbon atoms and further may have a substituent or a cycloalkyl groups having 3 to 20 carbon atoms and further may have a substituent.

Examples of the halogen atom include fluorine atom, chlorine atom, bromine atom and iodine atom, etc.

Examples of the alkyl group described above include methyl group, ethyl group, propyl group, isopropyl group, n-butyl group, s-butyl group, isobutyl group, t-butyl group, n-pentyl group, n-hexyl group, n-heptyl group, n-octyl group, etc.

Examples of the aromatic hydrocarbon group include moieties of benzene, naphthalene, anthracene, phenanthrene, pyrene, biphenyl terphenyl, fluoranthene, etc.

Examples of the heterocyclic group include moieties of imidazole, benzimidazole, pyrrole, furan, thiophene, benzothiophene, oxadiazoline, indoline, carbazole, pyridine, quinoline, isoquinoline, benzoquinone, pyrazoline, imidazolidine, piperidine, etc.

Examples of the alkylamino group include a group formed by substituting a hydrogen atom of the amino group with the above alkyl group.

Examples of the arylamino group include a group formed by substituting a hydrogen atom of the amino group with the aromatic hydrocarbon group.

The alkoxy group is expressed as —OY', wherein Y' represents a methyl group, an ethyl group, a propyl group, an isopropyl group, a n-butyl group, a s-butyl group, an isobutyl group, a t-butyl group, a n-pentyl group, a n-hexyl group, a n-heptyl group, a n-octyl group, etc.

Examples of the alkoxy halide group include a group formed by substituting a hydrogen atom of the alkoxy group with the above halogen atom.

The aryloxy group is expressed as —OY", wherein Y" represents moieties of benzene, naphthalene, anthracene, phenanthrene, pyrene, biphenyl, terphenyl fluoranthene, etc.

Examples of the alkyl halide group include a group formed by substituting a hydrogen atom of the alkyl group with the above halogen atom.

Examples of the alkenyl group include vinyl group, allyl group, 2-butenyl group, 3-pentenyl group, etc.

Examples of the alkynyl group include ethynyl group, methyl ethynyl group, etc.

Examples of the cycloalkyl group include cyclopropyl group, cyclobutyl group, cyclopentyl group, cyclohexyl group, etc.

Further, examples of the substituent for those groups include halogen atom, hydroxyl group, substituted or unsubstituted amino group, nitro group, cyano group, substituted or unsubstituted alkyl group, fluorination alkyl group, substituted or unsubstituted alkenyl group, a substituted or unsubstituted cycloalkyl group, substituted or unsubstituted alkoxyl group, substituted or unsubstituted heterocyclic group, substituted or unsubstituted arylalkyl group, a substituted or unsubstituted aryloxy group, substituted or unsubstituted alkoxycarbonyl group, carboxyl group, etc.

In the general formulae (I) and (II), X represents a monovalent ligand possessing an atom of Groups 14 to 17 in Periodic Table.

Examples of the atom of Groups 14 to 17 in Periodic Table and possessed by X include C (carbon) atom, N (nitrogen) atom, O (oxygen) atom, F (fluorine) atom, Si (silicon) atom, P (phosphor) atom, S (sulfur) atom, Cl (chlorine) atom, Ge (germanium) atom, As (arsenic) atom, Se (Se) atom, Br (bromine) atom, I (iodine) atom and so on, while carbon atom, nitrogen atom, chlorine atom, bromine atom and iodine atom are preferable.

Further, examples of the ligand represented by X include methoxy group, phenoxy group, cyano group, chlorine atom, bromine atom, iodine atom and so on, while cyano group, chlorine atom, bromine atom and iodine atom are preferable.

In the general formulae (I) and (II), Y represents an atom of Groups 14 to 16 in Periodic Table. Examples of the above atom of Groups 14 to 16 in Periodic Table expressed by Y include C (carbon) atom, N (nitrogen) atom, O (oxygen) atom, Si (silicon) atom, P (phosphor) atom, S (sulfur) atom, Ge (germanium) atom, As (arsenic) atom, Se (Se) atom and so on, while carbon atom, nitrogen atom and oxygen atom are preferable.

In the general formulae (I) and (II), A represents a cycloalkane moiety having 5 to 20 carbon atoms and further may have a substituent, an aromatic hydrocarbon group having 6 to 20 carbon atoms and further may have a substituent or a heterocyclic group having 2 to 20 carbon atoms and further may have a substituent indicating that a circle enclosing the sign A shows a ring structure comprising Y.

Examples of the above moiety of cycloalkane include moieties of cyclopropane, cyclobutane, cyclopropane, cyclohexane, cycloheptane, etc.

Further, specific examples of the aromatic hydrocarbon group and the heterocyclic group are preferably a hydrogen atom, a cyano group, a halogen atom, an alkyl group having 1 to 12 carbon atoms and further may have a substituent, an alkylamino group having 1 to 12 carbon atoms and further may have a substituent, an arylamino group having 6 to 20 carbon atoms and further may have a substituent, an alkoxy group having 1 to 12 carbon atoms and further may have a substituent, an alkoxy halide group having 1 to 12 carbon atoms and further may have a substituent, an aryloxy group having 6 to 20 carbon atoms and further may have a substituent, an aromatic hydrocarbon group having 6 to 20 carbon atoms and further may have a substituent, a heterocyclic group having 3 to 20 carbon atoms and further may have a substituent, an alkyl halide group having 1 to 12 carbon atoms and further may have a substituent, an alkenyl group having 1 to 12 carbon atoms and further may have a substituent, an alkynyl group having 1 to 12 carbon atoms and further may have a substituent or a cycloalkyl groups having 3 to 20 carbon atoms and further may have a substituent.

Specific substituents of those groups are the same as the foregoing description.

In the general formulae (I) and (II), $R^1$ to $R^4$ each independently represents a hydrogen atom, a cyano group, a halogen atom, an alkyl group having 1 to 12 carbon atoms and further may have a substituent, an alkylamino group having 1 to 12 carbon atoms and further may have a substituent, an arylamino group having 6 to 20 carbon atoms and further may have a substituent, an alkoxy group having 1 to 12 carbon atoms and further may have a substituent, an alkoxy halide group having 1 to 12 carbon atoms and further may have a substituent, an aryloxy group having 6 to 20 carbon atoms and further may have a substituent, an aromatic hydrocarbon group having 6 to 20 carbon atoms and further may have a substituent, a heterocyclic group having 3 to 20 carbon atoms and further may have a substituent, an alkyl halide group having 1 to 12 carbon atoms and further may have a substituent, an alkenyl group having 1 to 12 carbon atoms and further may have a substituent, an alkynyl group having 1 to 12 carbon atoms and further may have a substituent or a cycloalkyl groups having 1 to 12 carbon atoms and further may have a substituent; and Specific examples of those groups are the same as the foregoing specific examples of L and Z.

Further, $R^1$ & $R^2$ or $R^3$ & $R^4$ may bond each other to form a ring structure. The ring structure is exemplified as a heterocyclic group having nitrogen atom, and examples include imidazole, benzimidazole, pyrrole, indoline, carbazole, pyridine, a quinoline, isoquinoline, pyrazoline, imidazolidine, piperidine and so on, while pyridine, imidazole and benzimidazole are preferable.

Specific substituents of those groups are the same as the foregoing description.

In the general formula (I), the above tridentate chelate ligand is any one of compounds shown by following general formulae (1) to (21) and (22) to (30):

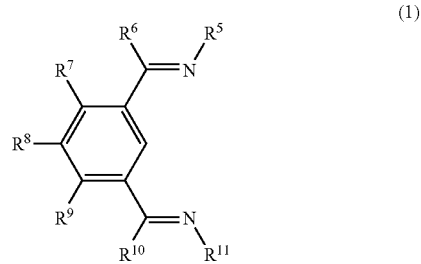

(1)

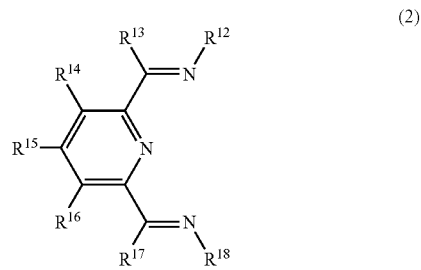

(2)

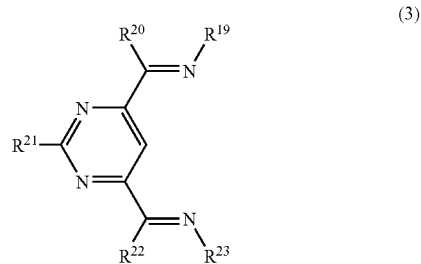

(3)

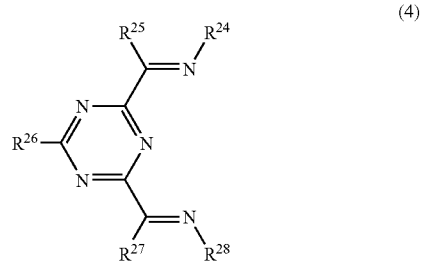

(4)

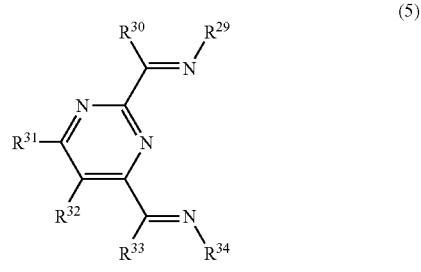

(5)

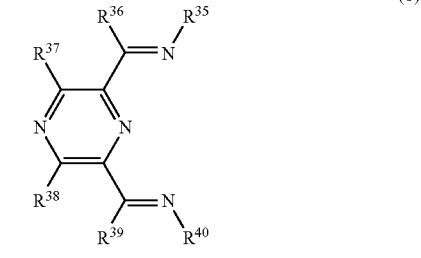

(6)

-continued
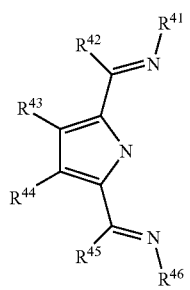 (7)
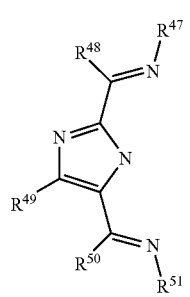 (8)
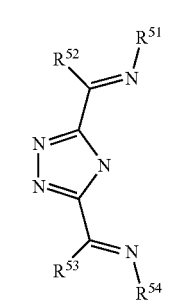 (9)
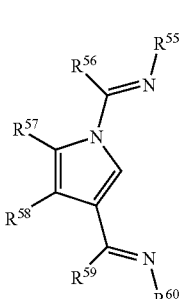 (10)
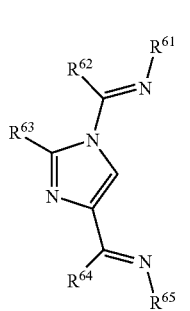 (11)
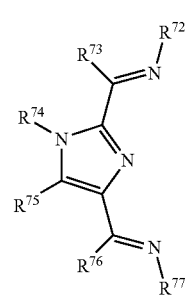 (12)
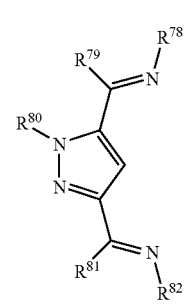 (13)
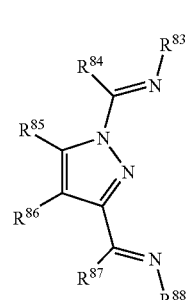 (14)
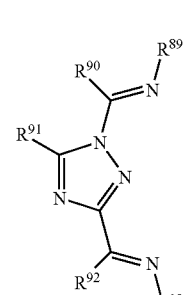 (15)
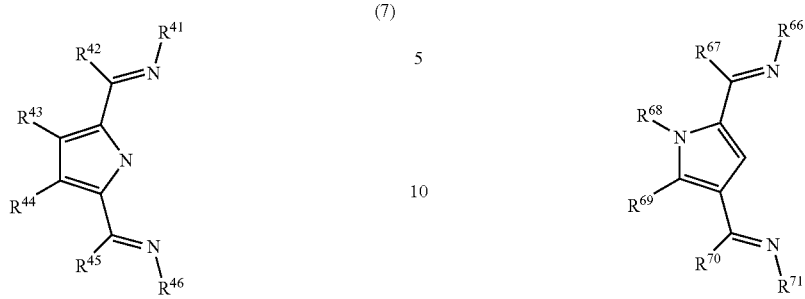

-continued

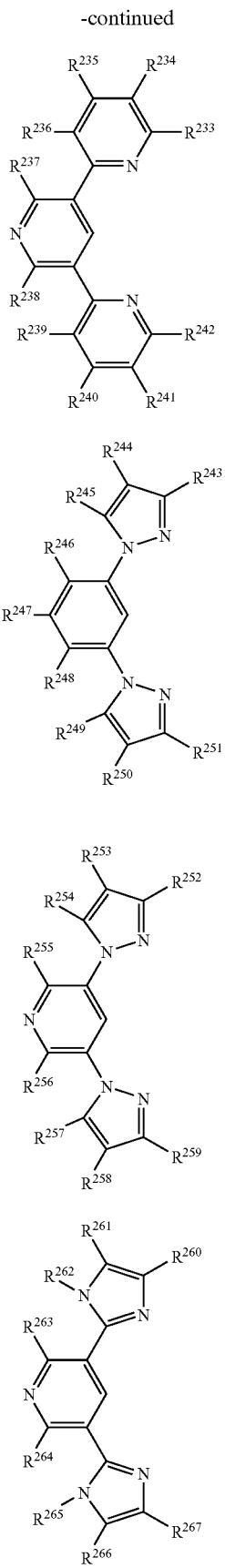

In the general formulae (1) to (21) and (22) to (30), $R^5$ to $R^{98}$, $R^{157}$ to $R^{196}$ and $R^{207}$ to $R^{232}$ each independently represents a hydrogen atom, a cyano group, a halogen atom, an alkyl group having 1 to 12 carbon atoms and further may have a substituent, an alkylamino group having 1 to 12 carbon atoms and further may have a substituent, an arylamino group having 6 to 20 carbon atoms and further may have a substituent, an alkoxy group having 1 to 12 carbon atoms and further may have a substituent, an alkoxy halide group having 1 to 12 carbon atoms and further may have a substituent, an aryloxy group having 6 to 20 carbon atoms and further may have a substituent, an aromatic hydrocarbon group having 6 to 20 carbon atoms and further may have a substituent, a heterocyclic group having 3 to 20 carbon atoms and further may have a substituent, an alkyl halide group having 1 to 12 carbon atoms and further may have a substituent, an alkenyl group having 1 to 12 carbon atoms and further may have a substituent, an alkynyl group having 1 to 12 carbon atoms and further may have a substituent or a cycloalkyl groups having 1 to 12 carbon atoms and further may have a substituent; Specific examples and substituents of the each above groups are the same as those described about the foregoing $R^1$ to $R^4$. Further, $R^5$ to $R^{98}$, $R^{157}$ to $R^{196}$ and $R^{207}$ to $R^{232}$ each independently exists two or more allowing that $R^5$ to $R^{98}$, $R^{157}$ to $R^{196}$ and $R^{207}$ to $R^{232}$ each are the same with or different from each other; and each adjacent couple among $R^5$ to $R^{98}$, $R^{157}$ to $R^{196}$ and $R^{207}$ to $R^{282}$ may bond each other to form a ring structure.

Examples of the ring structure include/cycloalkane (for example, cyclopropane, cyclobutane, cyclopropane, cyclohexane, cycloheptane, etc.), aromatic hydrocarbon ring (for example, benzene, naphthalene, anthracene, phenanthrene, pyrene, biphenyl, terphenyl fluoranthene, etc.) and heterocycle (for example, imidazole, benzimidazole, pyrrole, furan, thiophene, benzothiophene, oxadiazoline, diphenylanthracene, indoline, carbazole, pyridine, quinoline, isoquinoline, benzoquinone, pyrazoline, imidazolidine, piperidine, etc.).

In the general formulae (I) and (II), a ligand formed by L—Z is any one of compounds shown by following general formulae (31) to (39):

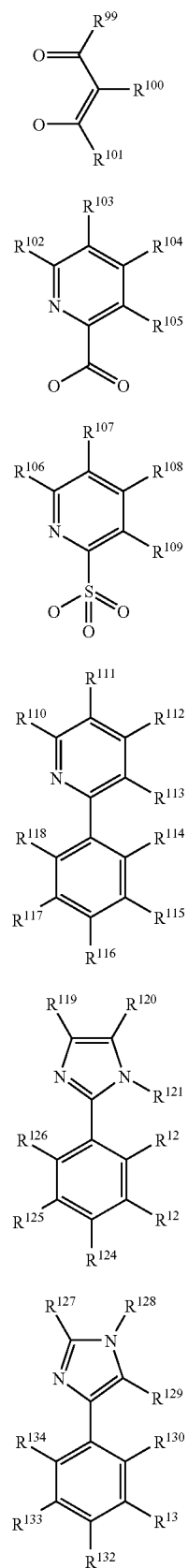

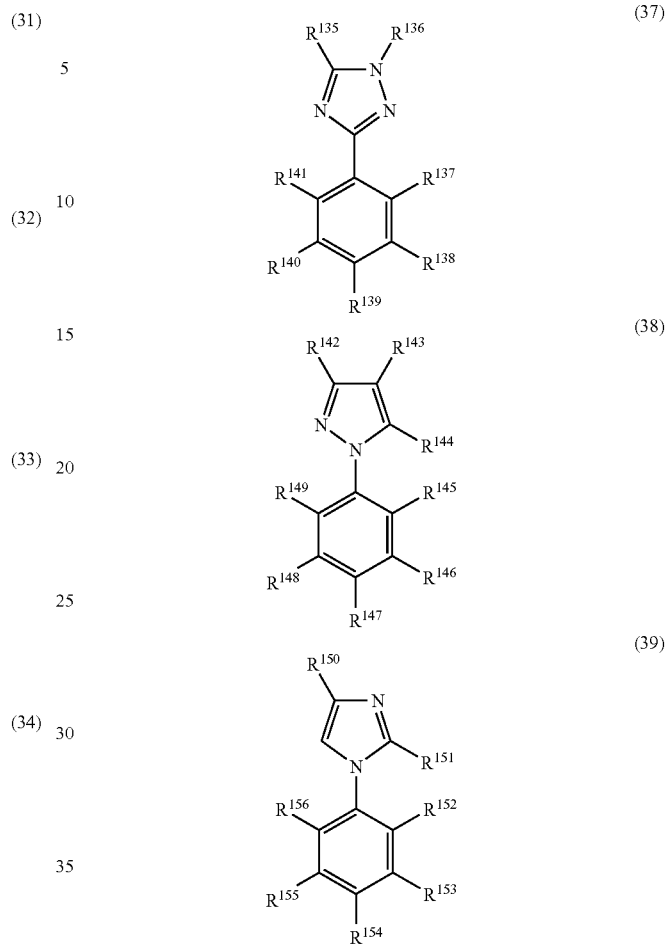

In the general formulae (31) to (39), $R^{99}$ to $R^{156}$ each independently represents a hydrogen atom, a cyano group, a halogen atom, an alkyl group having 1 to 12 carbon atoms and further may have a substituent, an alkylamino group having 1 to 12 carbon atoms and further may have a substituent, an arylamino group having 6 to 20 carbon atoms and further may have a substituent, an alkoxy group having 1 to 12 carbon atoms and further may have a substituent, an alkoxy halide group having 1 to 12 carbon atoms and further may have a substituent, an aryloxy group having 6 to 20 carbon atoms and further may have a substituent, an aromatic hydrocarbon group having 6 to 20 carbon atoms and further may have a substituent, a heterocyclic group having 3 to 20 carbon atoms and further may have a substituent, an alkyl halide group having 1 to 12 carbon atoms and further may have a substituent, an alkenyl group having 1 to 12 carbon atoms and further may have a substituent, an alkynyl group having 1 to 12 carbon atoms and further may have a substituent or a cycloalkyl groups having 1 to 12 carbon atoms and further may have a substituent; Specific examples and substituents of the each above groups are the same as those described about the foregoing $R^1$ to $R^4$. Further, $R^{99}$ to $R^{156}$ each independently exists two or more allowing that $R^{99}$ to $R^{156}$ each are the same with or different from each other; and each adjacent couple among $R^{99}$ to $R^{156}$ may bond each other to form a ring structure.

Examples of the ring structure are the same as those described about the foregoing $R^5$ to $R^{98}$, $R^{157}$ to $R^{196}$, and $R^{207}$ to $R^{276}$.
It is preferable that the metal-complex compound represented by the general formula (I) of the present invention is shown by following general formulae (I-1) to (I-9) and (I-10) to (I-15).
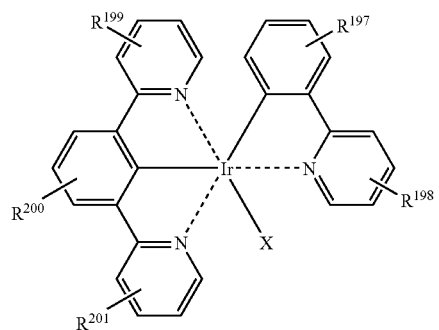
(I-1)
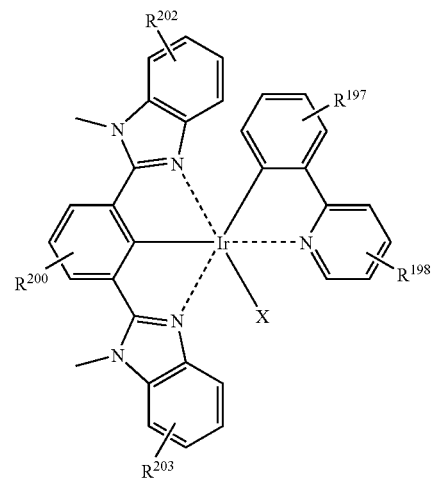
(I-2)
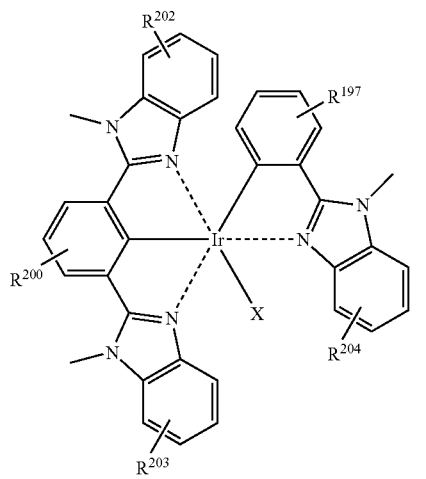
(I-3)
-continued
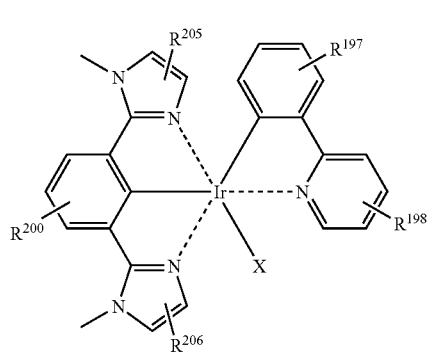
(I-4)
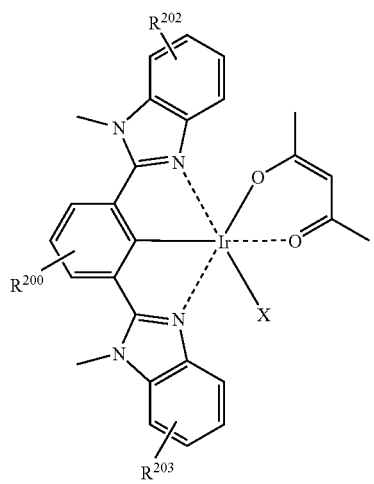
(I-5)
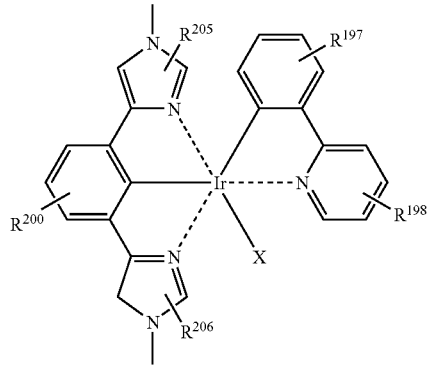
(I-6)

-continued
(I-7)
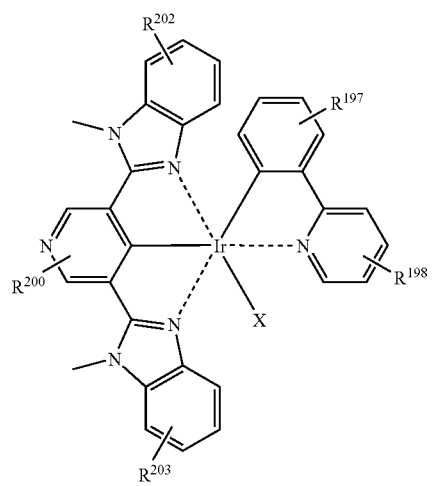
(I-8)
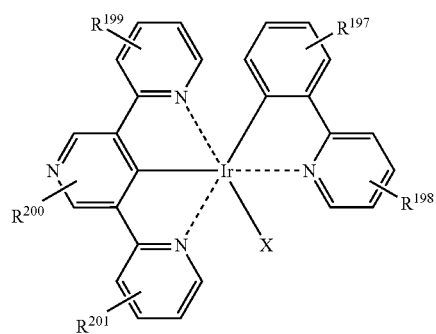
(I-9)
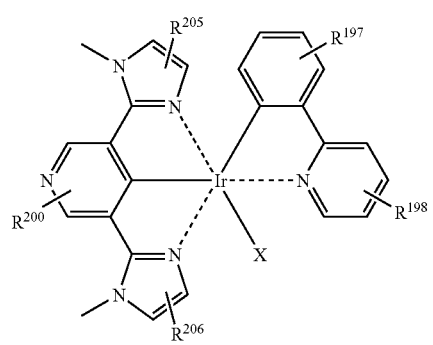
(I-10)
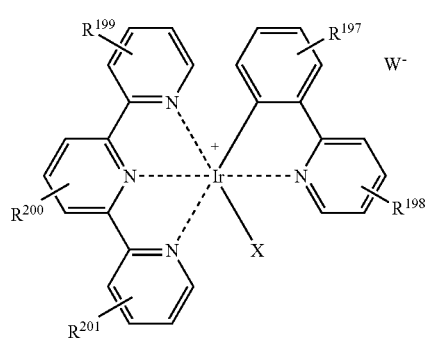
-continued
(I-11)
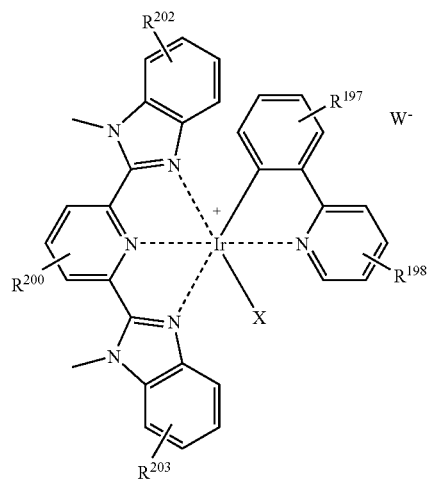
(I-12)
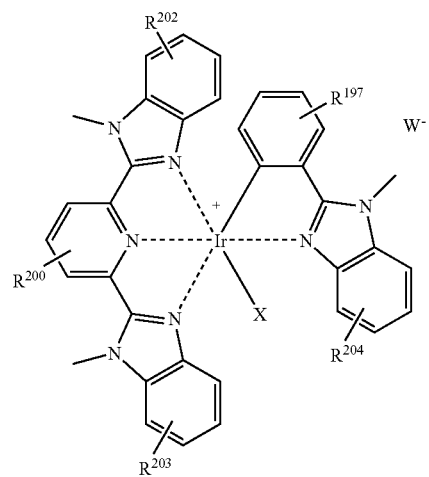
(I-13)
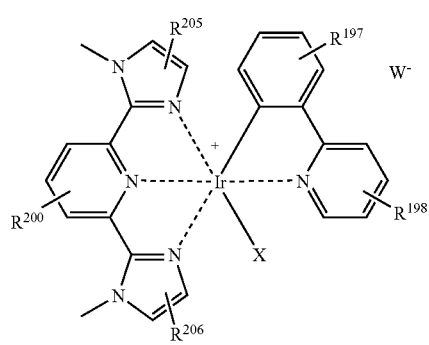

-continued (I-14)
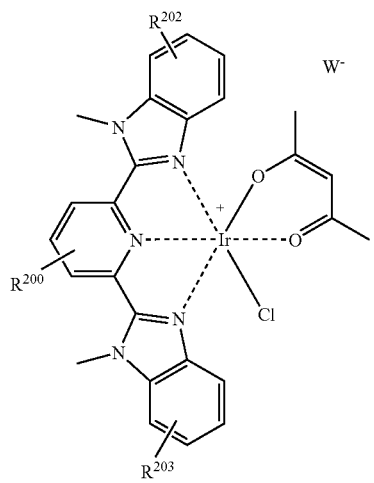

(I-15)
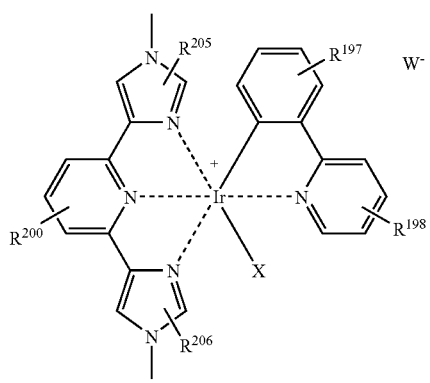

In the general formulae (I-1) to (I-15), $R^{197}$ to $R^{206}$ each independently represents a hydrogen atom, a cyano group, a halogen atom, an alkyl group having 1 to 12 carbon atoms and further may have a substituent, an alkylamino group having 1 to 12 carbon atoms and further may have a substituent, an arylamino group having 6 to 20 carbon atoms and further may have a substituent, an alkoxy group having 1 to 12 carbon atoms and further may have a substituent, an alkoxy halide group having 1 to 12 carbon atoms and further may have a substituent, an aryloxy group having 6 to 20 carbon atoms and further may have a substituent, an aromatic hydrocarbon group having 6 to 20 carbon atoms and further may have a substituent, a heterocyclic group having 3 to 20 carbon atoms and further may have a substituent, an alkyl halide group having 1 to 12 carbon atoms and further may have a substituent, an alkenyl group having 1 to 12 carbon atoms and further may have a substituent, an alkynyl group having 1 to 12 carbon atoms and further may have a substituent or a cycloalkyl groups having 1 to 12 carbon atoms and further may have a substituent. Specific examples and substituents of the each above groups are the same as those described about the foregoing $R^1$ to $R^4$. Further, $R^{197}$ to $R^{206}$ each independently exists two or more allowing that $R^{197}$ to $R^{206}$ each are the same with or different from each other; and each adjacent couple among $R^{197}$ to $R^{206}$ may bond each other to form a ring structure.

Examples of the ring structure are the same as those described about the foregoing $R^5$ to $R^{98}$ and $R^{157}$ to $R^{198}$.

In the general formulae (I-1) to (I-15), W⁻ represents a minus ion of valence −1 having at least one kind of metal atom among Groups 13 to 16 of Periodic Table. Examples include $PF_6^-$, $ClO_4^-$, $SbF_6^-$, OTf, OTs⁻, $BF_4^-$, $BPh_4^-$, $B(C_6F_5)^-$ and so on, while $PF_6^-$ is preferable.

In the general formula (II), the foregoing tridentate chelate ligand is preferably any one of compounds shown by following general formulae (40) to (42) and (43) to (44):

(40)
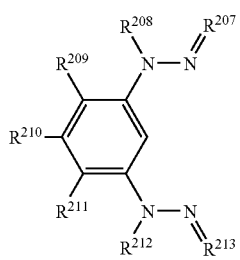

(41)
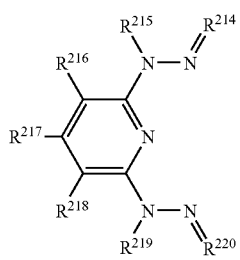

(42)
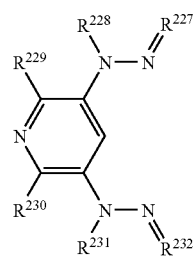

-continued

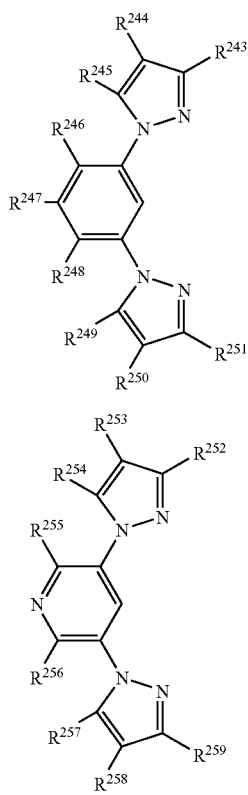

(43)

(44)

In the general formulae (40) to (42) and (43) to 4) $R^{207}$ to $R^{220}$, $R^{227}$ to $R^{232}$ and $R^{243}$ to $R^{259}$ each independently represents a hydrogen atom, a cyano group, a halogen atom, an alkyl group having 1 to 12 carbon atoms and further may have a substituent, an alkylamino group having 1 to 12 carbon atoms and further may have a substituent, an arylamino group having 6 to 20 carbon atoms and further may have a substituent, an alkoxy group having 1 to 12 carbon atoms and further may have a substituent, an alkoxy halide group having 1 to 12 carbon atoms and further may have a substituent, an aryloxy group having 6 to 20 carbon atoms and further may have a substituent, an aromatic hydrocarbon group having 6 to 20 carbon atoms and further may have a substituent, a heterocyclic group having 3 to 20 carbon atoms and further may have a substituent, an alkyl halide group having 1 to 12 carbon atoms and further may have a substituent, an alkenyl group having 1 to 12 carbon atoms and further may have a substituent, an alkynyl group having 1 to 12 carbon atoms and further may have a substituent or a cycloalkyl groups having 1 to 12 carbon atoms and further may have a substituent. Specific examples and substituents of the each above groups are the same as those described about the foregoing $R^1$ to $R^4$. Further, $R^{207}$ to $R^{220}$, $R^{227}$ to $R^{232}$ and $R^{243}$ to $R^{259}$ each independently exists two or more allowing that $R^{207}$ to $R^{220}$, $R^{227}$ to $R^{232}$ and $R^{243}$ to $R^{259}$ each are the same with or different from each other; and each adjacent couple among $R^{207}$ to $R^{220}$, $R^{227}$ to $R^{232}$ and $R^{243}$ to $R^{259}$ may bond each other to form a ring structure.

It is preferable that the metal-complex compound represented by the general formula (II) of the present invention is shown by following general formula (II-1) or general formula (II-2):

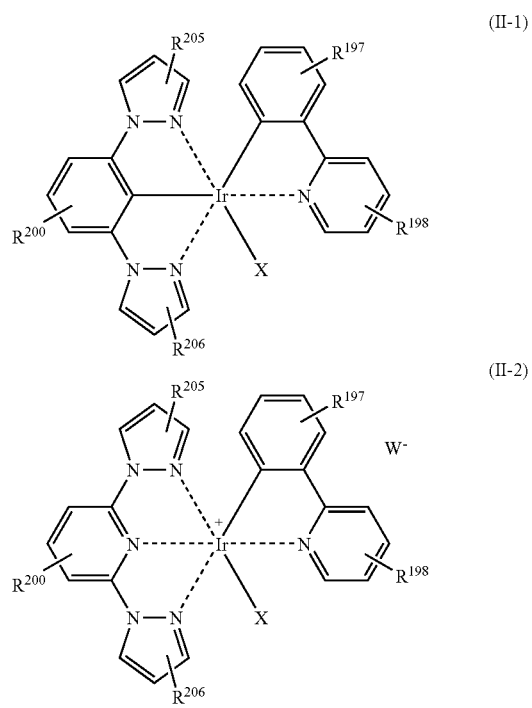

(II-1)

(II-2)

In the general formulae (II-1) and (II-2), $R^{197}$ to $R^{206}$ each independently represents a hydrogen atom, a cyano group, a halogen atom, an alkyl group having 1 to 12 carbon atoms and further may have a substituent, an alkylamino group having 1 to 12 carbon atoms and further may have a substituent, an arylamino group having 6 to 20 carbon atoms and further may have a substituent, an alkoxy group having 1 to 12 carbon atoms and further may have a substituent, an alkoxy halide group having 1 to 12 carbon atoms and further may have a substituent, an aryloxy group having 6 to 20 carbon atoms and further may have a substituent, an aromatic hydrocarbon group having 6 to 20 carbon atoms and further may have a substituent, a heterocyclic group having 3 to 20 carbon atoms and further may have a substituent, an alkyl halide group having 1 to 12 carbon atoms and further may have a substituent, an alkenyl group having 1 to 12 carbon atoms and further may have a substituent, an alkynyl group having 1 to 12 carbon atoms and further may have a substituent or a cycloalkyl groups having 1 to 12 carbon atoms and further may have a substituent; Specific examples and substituents of the each above groups are the same as those described about the foregoing $R^1$ to $R^4$. Further, $R^{197}$ to $R^{206}$ each independently exists two or more allowing that $R^{197}$ to $R^{206}$ each are the same with or different from each other; and each adjacent couple among $R^{197}$ to $R^{206}$ may bond each other to form a ring structure.

Examples of the ring structure are the same as those described about the foregoing $R^5$ to $R^{98}$ and $R^{157}$ to $R^{196}$.

In the general formula (II-2), W$^-$ represents a minus ion of valence −1 having at least one kind of metal atom among Groups 13 to 16 of Periodic Table. Examples include $PF_6^-$, $ClO_4^-$, $SbF_6^-$, OTf, OTs$^-$, $BF_4^-$, $BPh_4^-$, $B[C_6F_5]_4^-$ and so on, while $PF_6^-$ is preferable.

Specific examples of the metal-complex compound of the present invention are as follows, however, the present invention is not limited to these typical compounds.
1
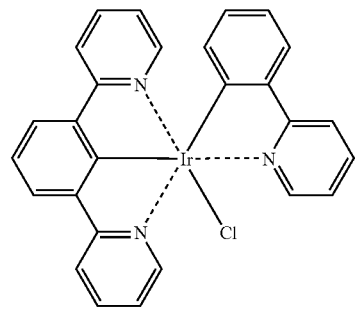
2
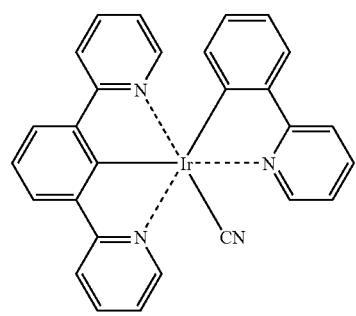
3
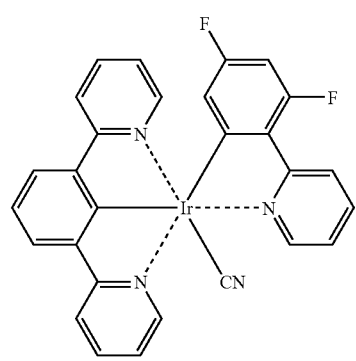
4
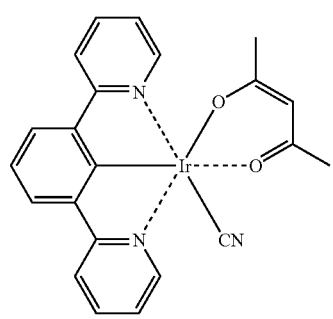
5
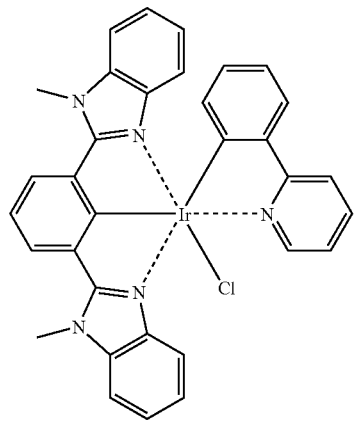
6
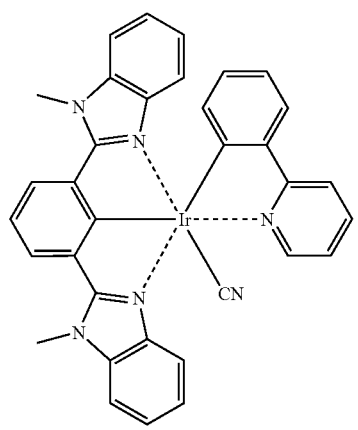
7
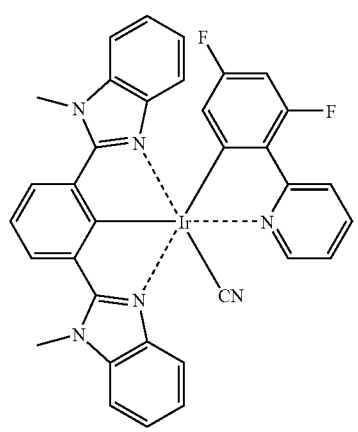

-continued
8
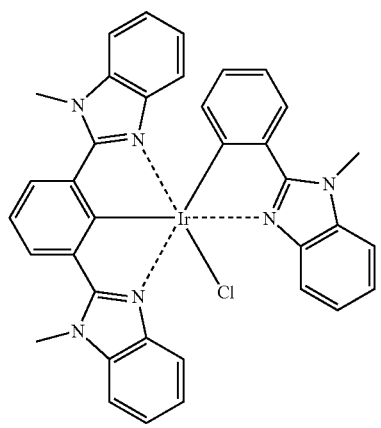
9
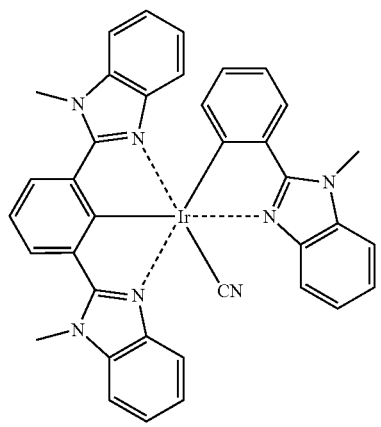
10
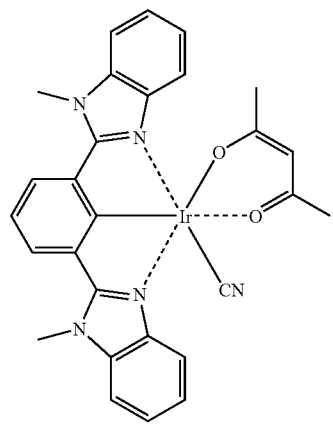
11
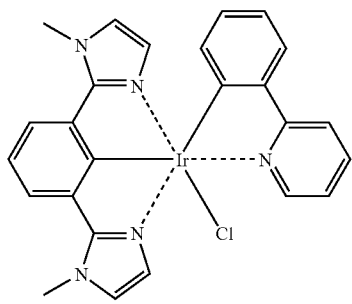
-continued
12
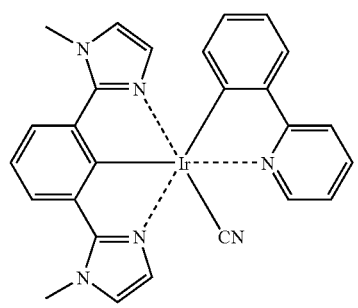
13
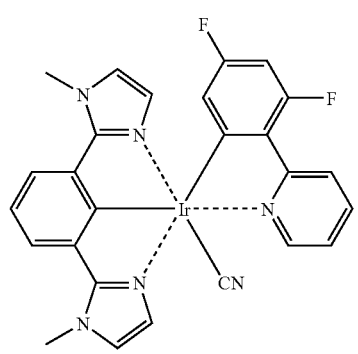
14
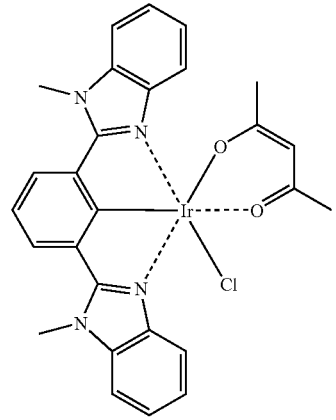
15
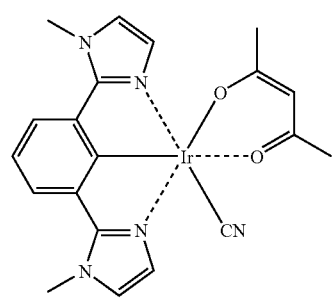

-continued
16
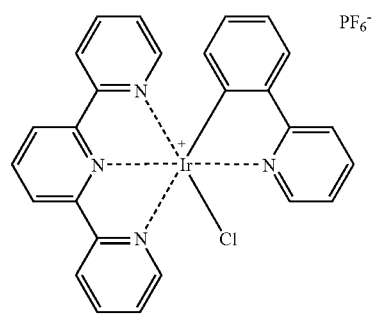
17
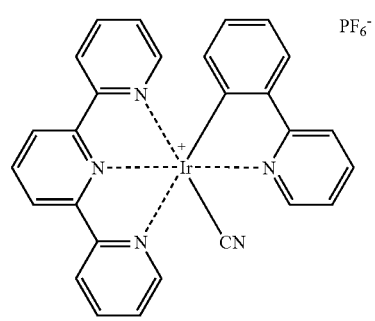
18
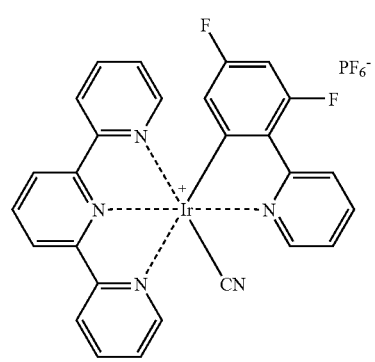
19
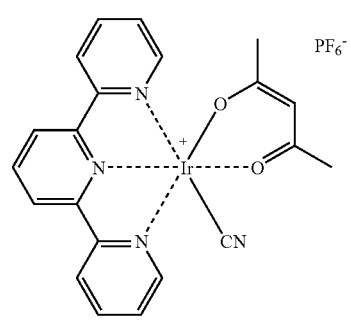
-continued
20
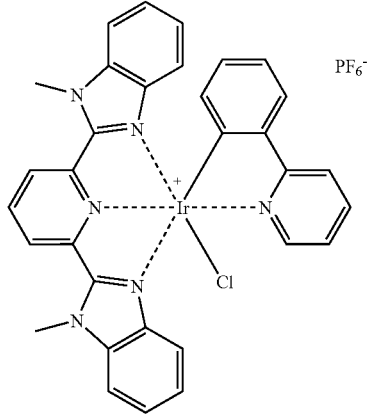
21
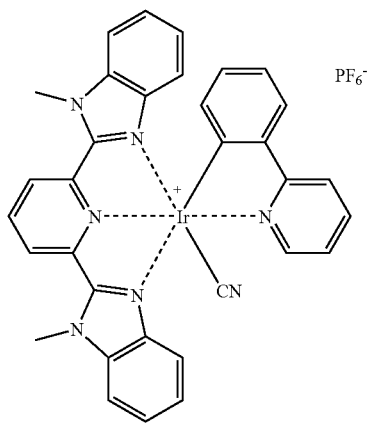
22
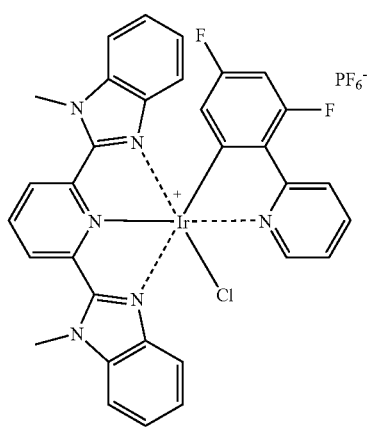

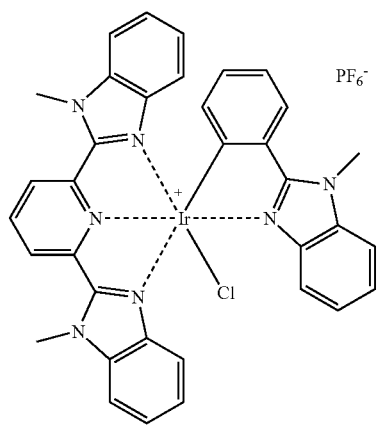
23
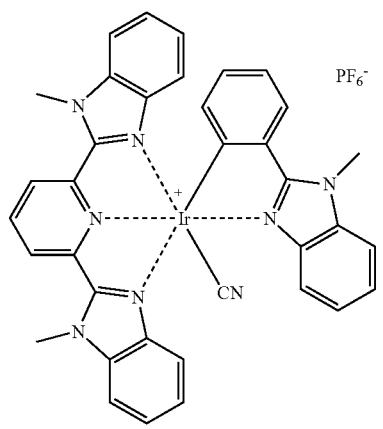
24
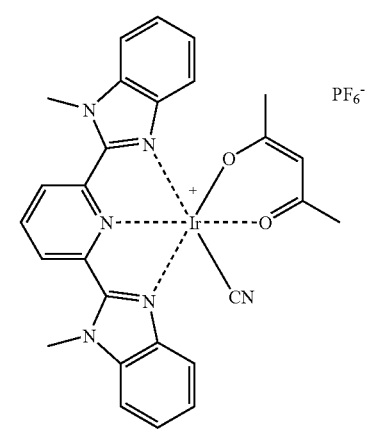
25
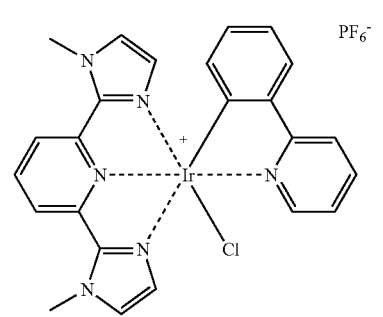
26
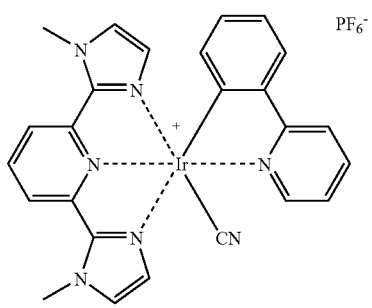
27
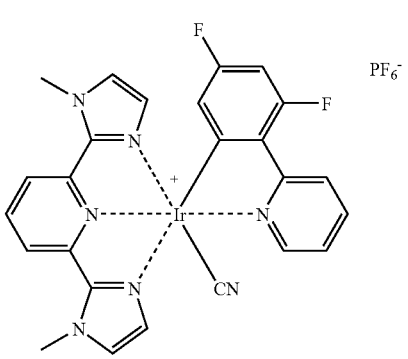
29
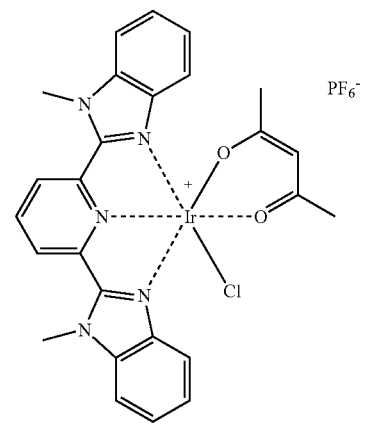
30
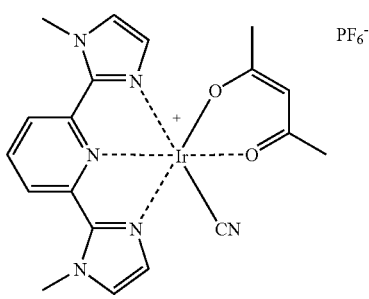
31

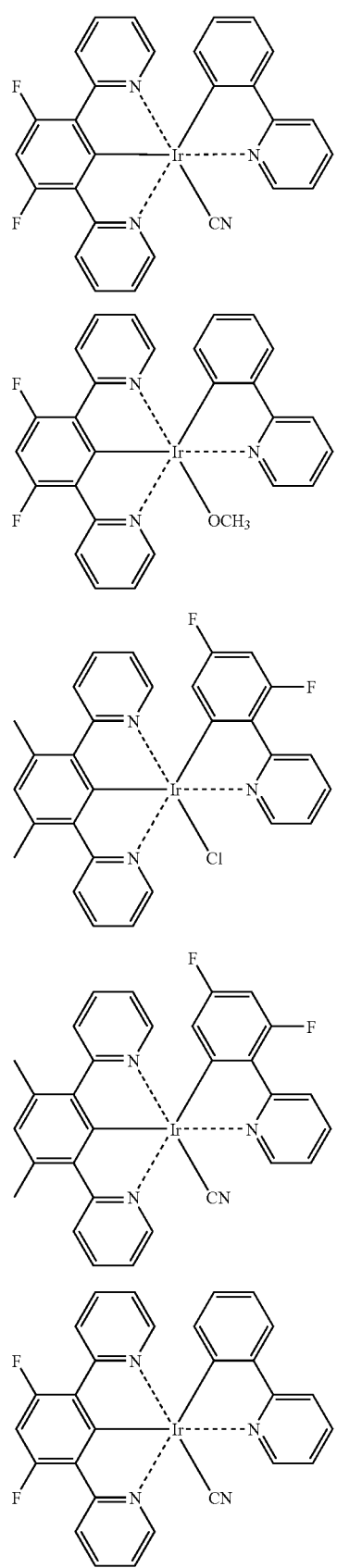

41
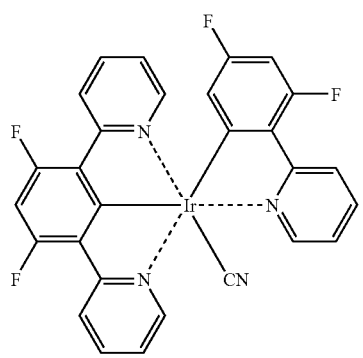
42
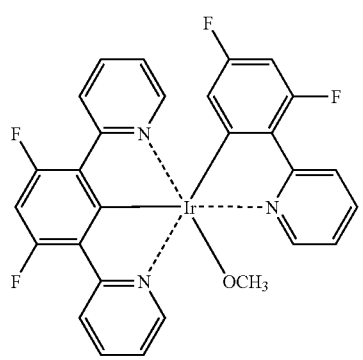
43
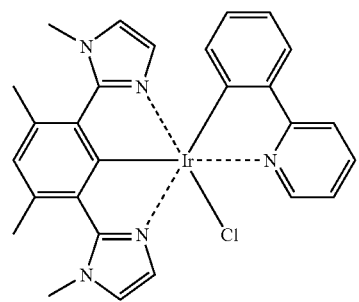
44
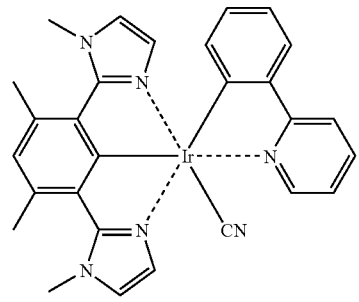
45
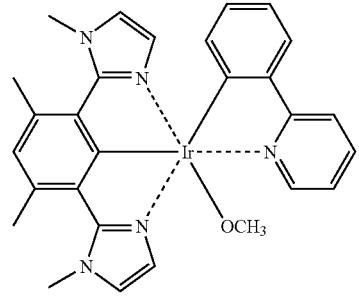
46
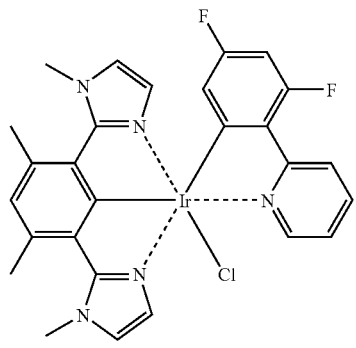
47
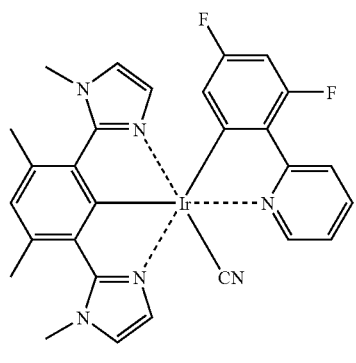
48
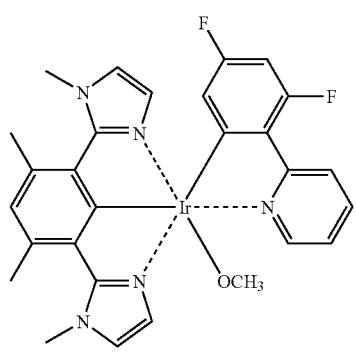
49
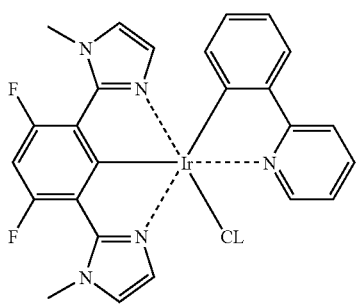
50
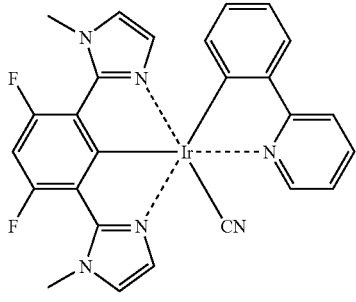

51
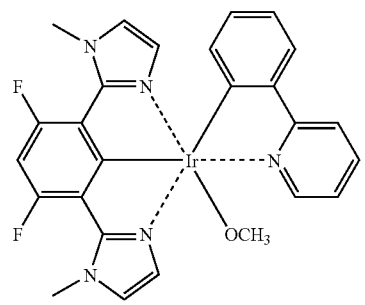
52
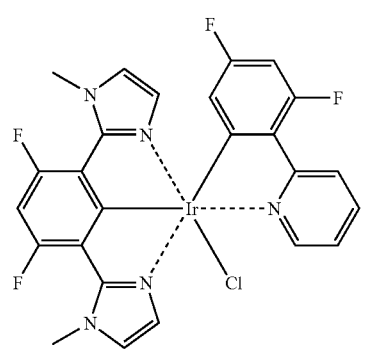
53
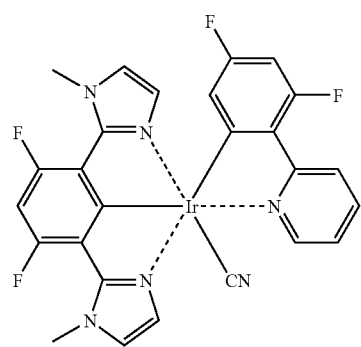
54
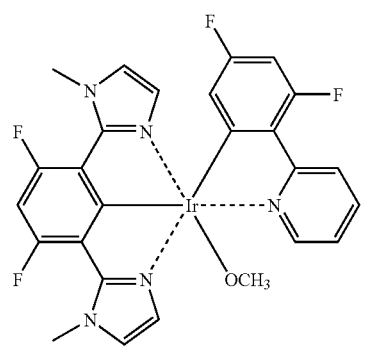
55
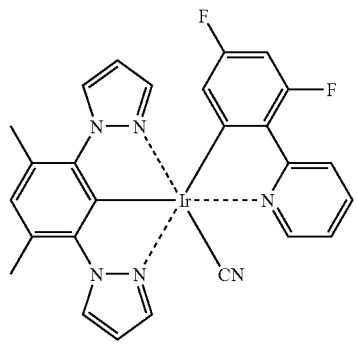
56
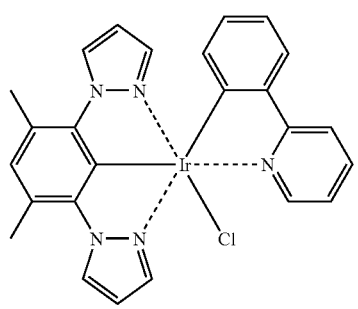
57
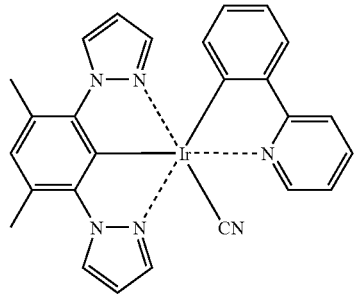
58
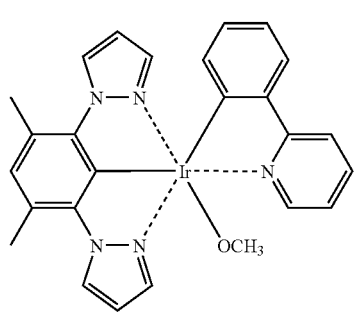
59
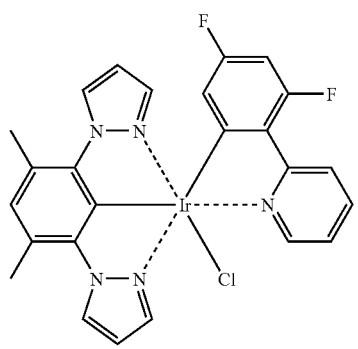

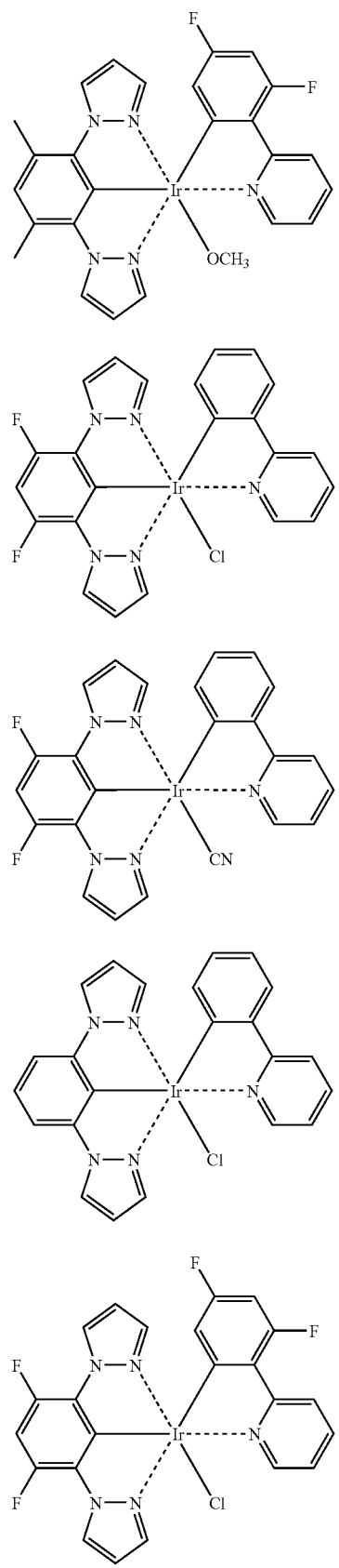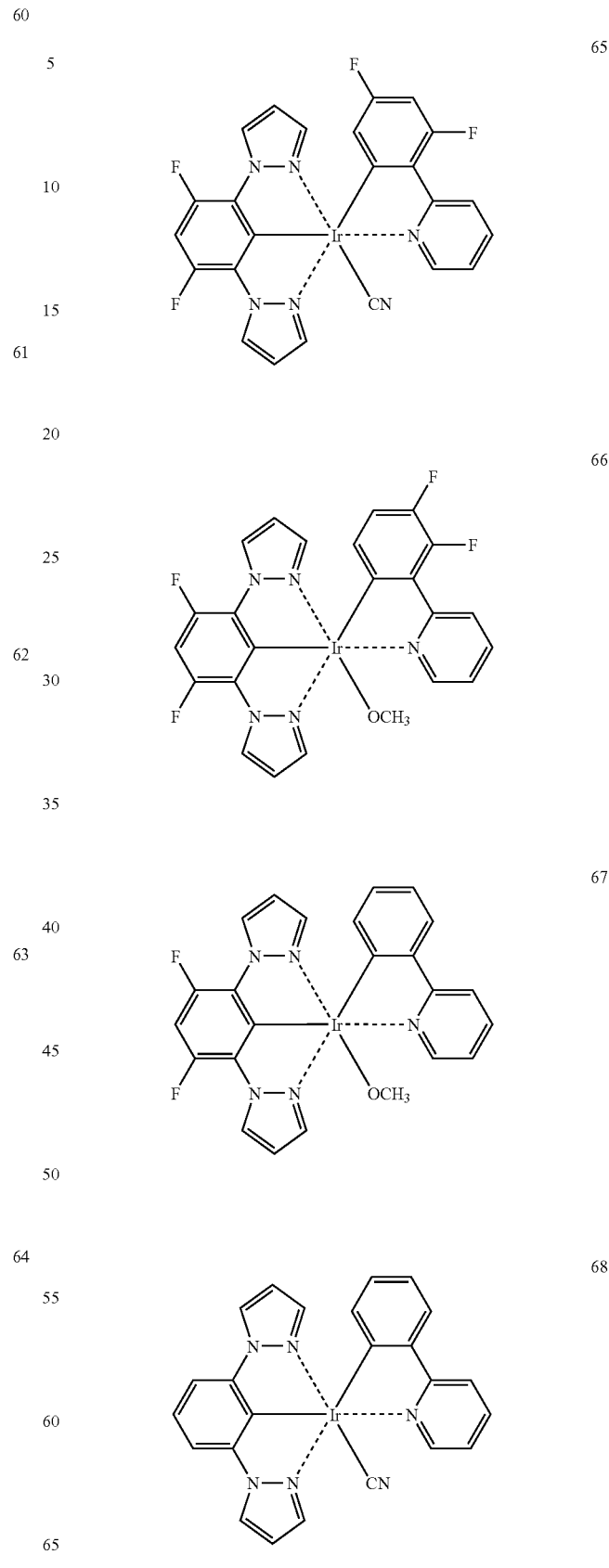

69
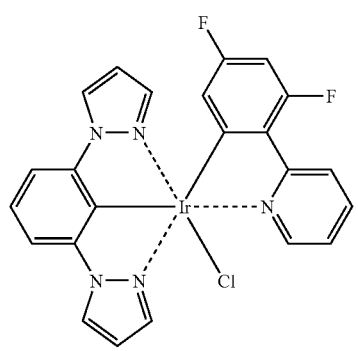
70
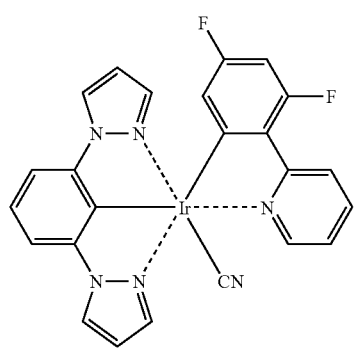
71
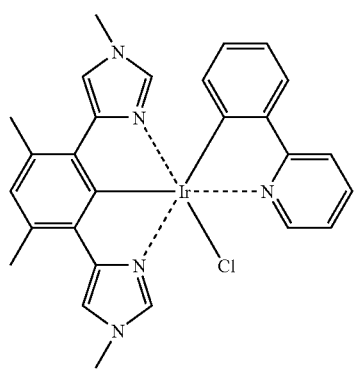
72
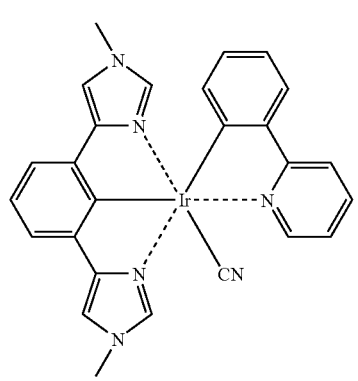
73
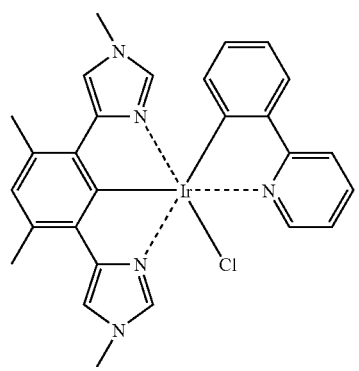
74
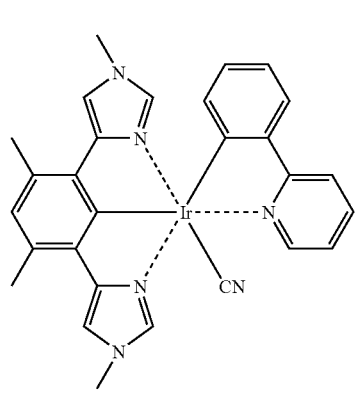
75
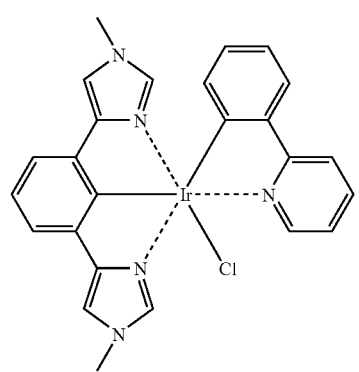
76
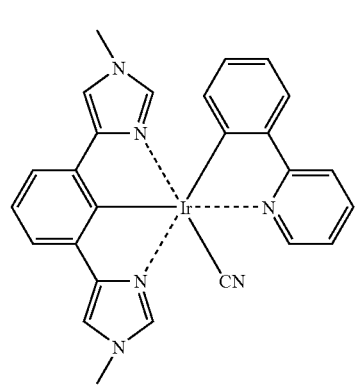

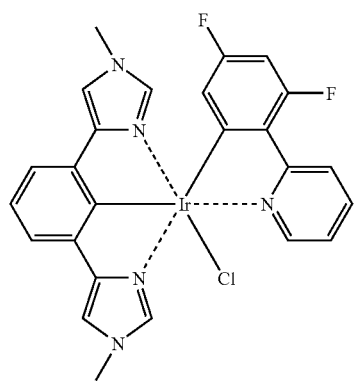 77
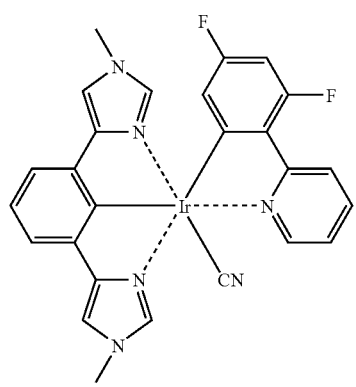 78
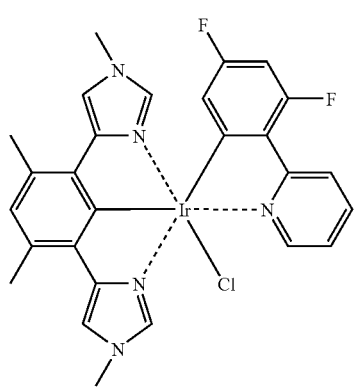 79
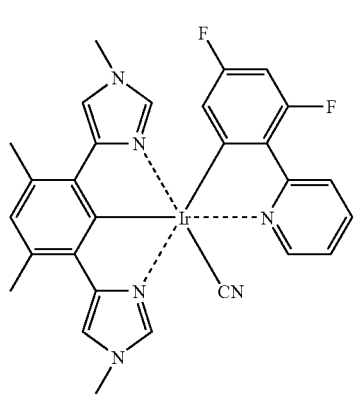 80
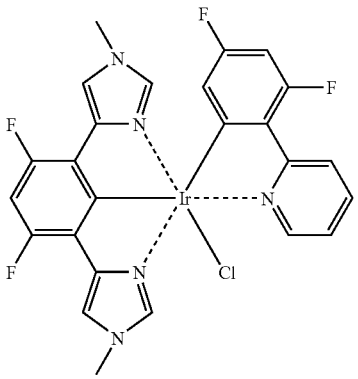 81
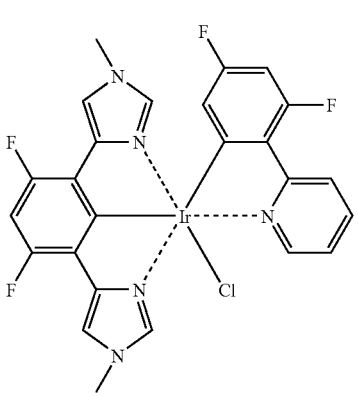 82
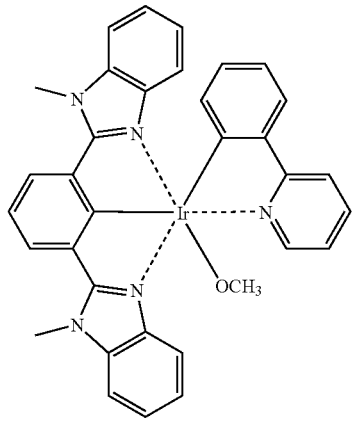 83
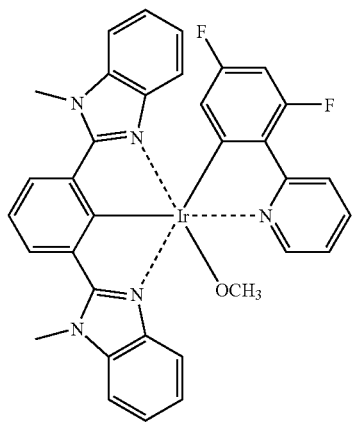 84

-continued
85
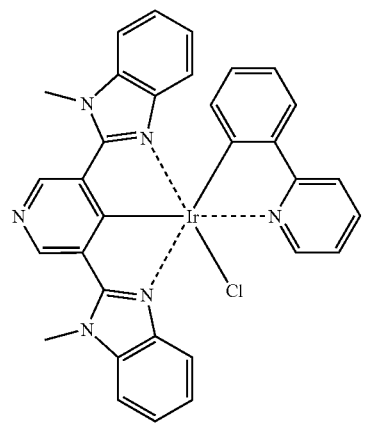
86
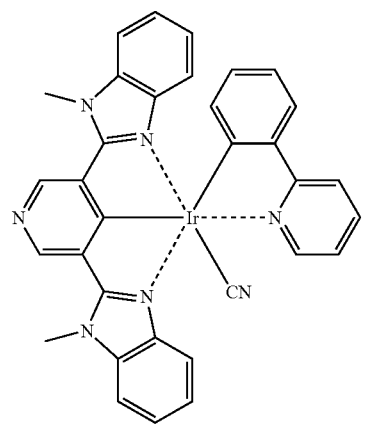
87
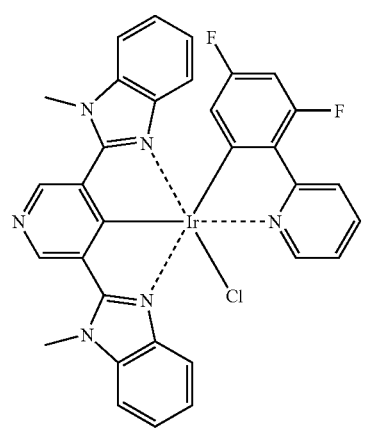
-continued
88
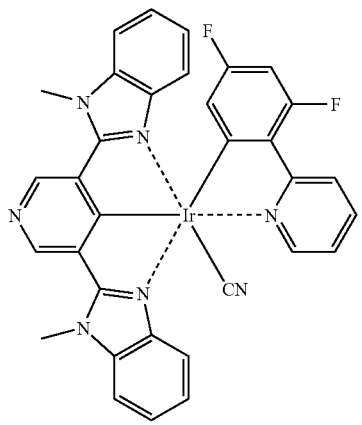
89
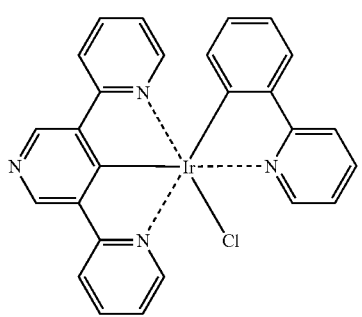
90
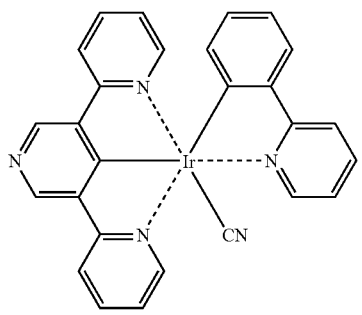
91
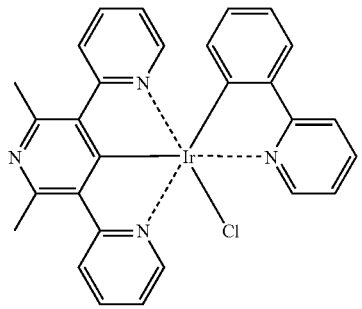

-continued
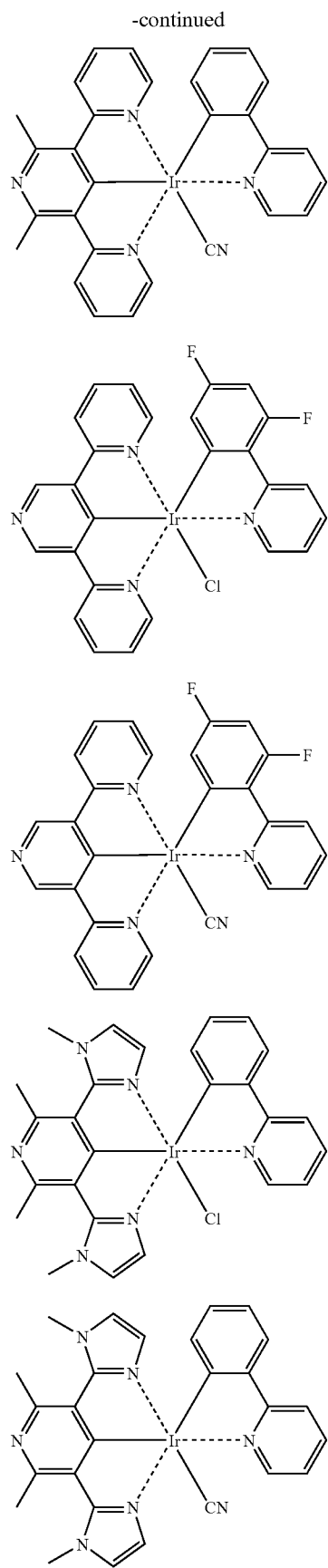
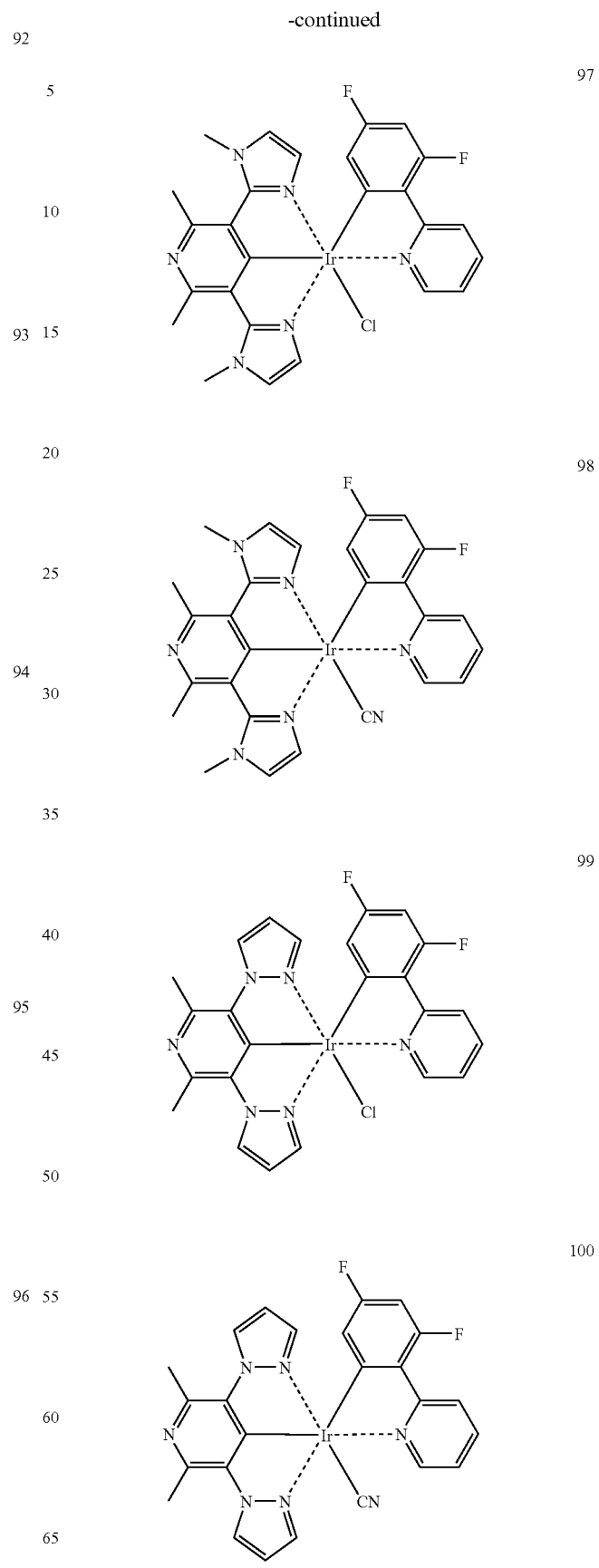

-continued
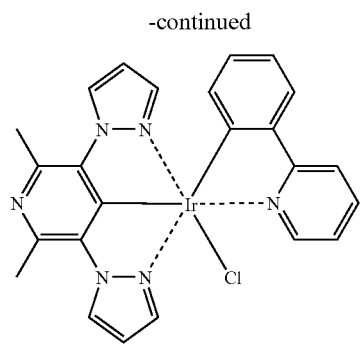
101
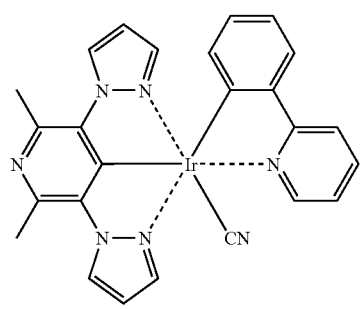
102
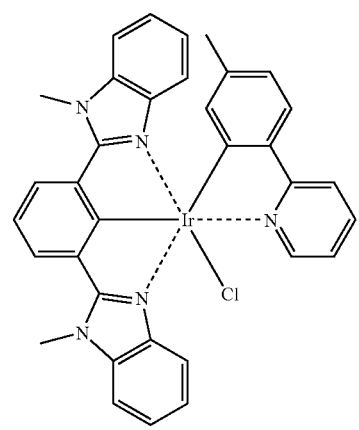
103
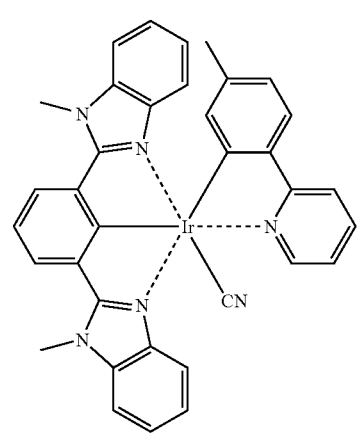
104
-continued
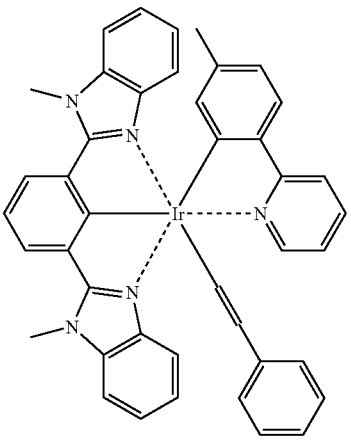
105
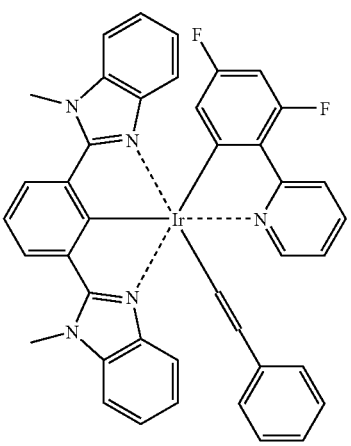
106
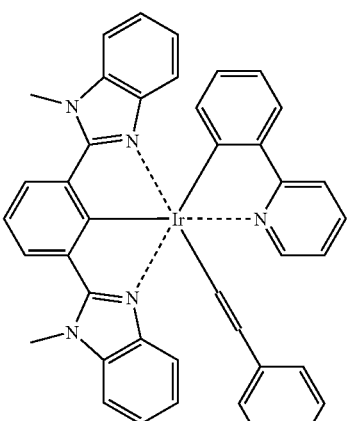
107

-continued
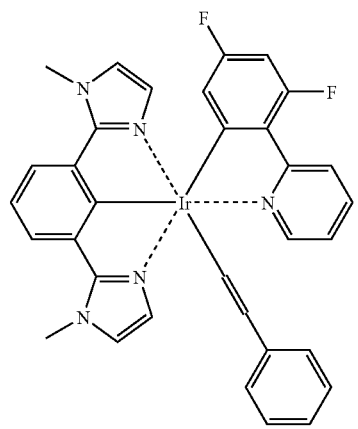 108
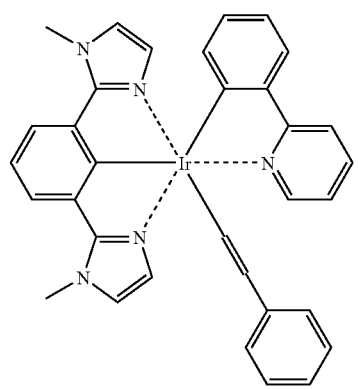 109
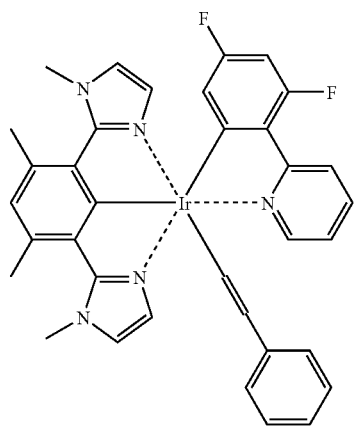 110
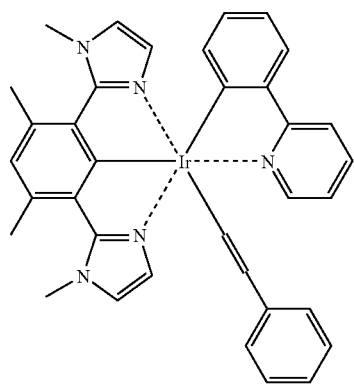 111
-continued
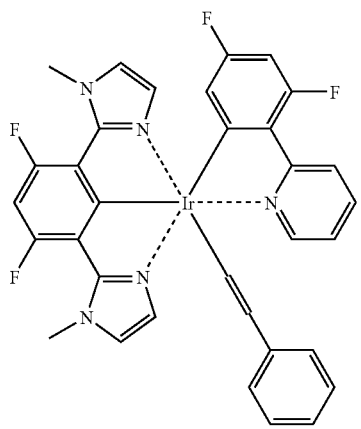 112
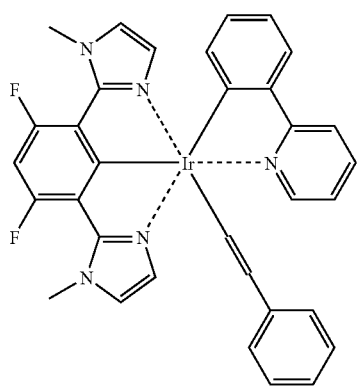 113
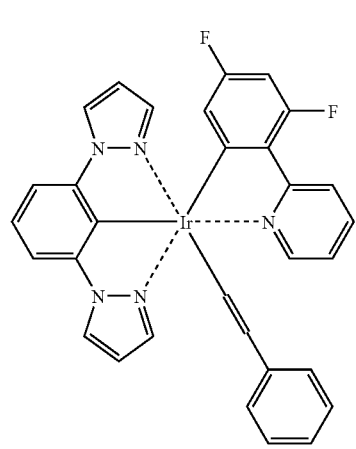 114
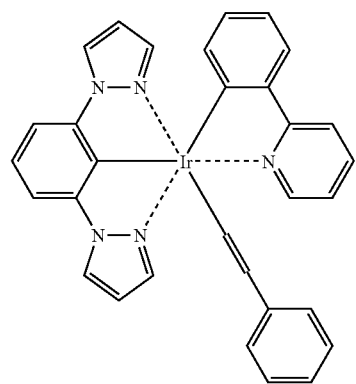 115

-continued
116
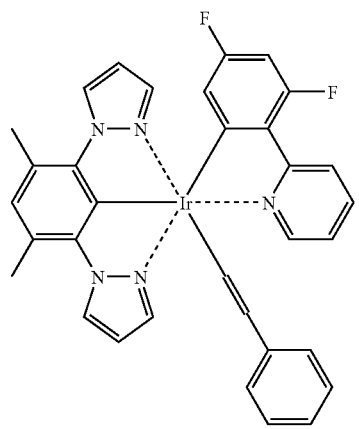
117
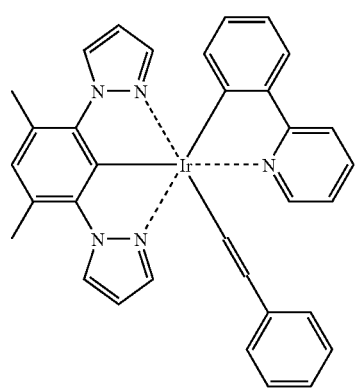
118
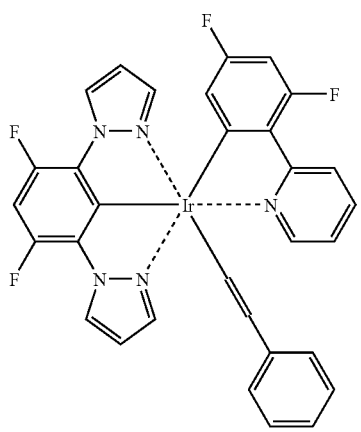
119
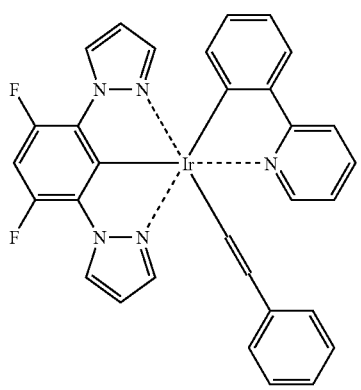
-continued
120
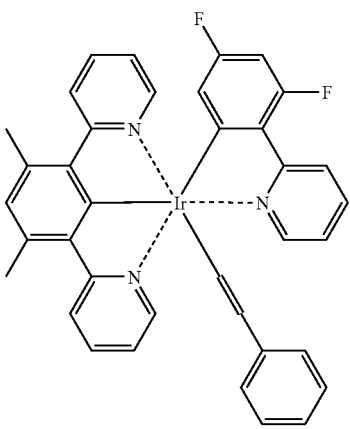
121
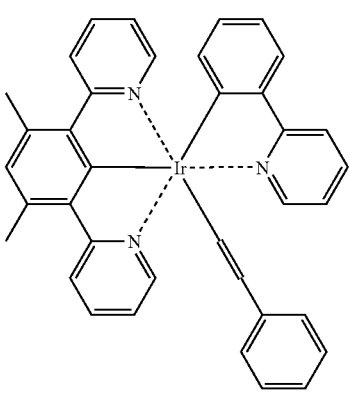
122
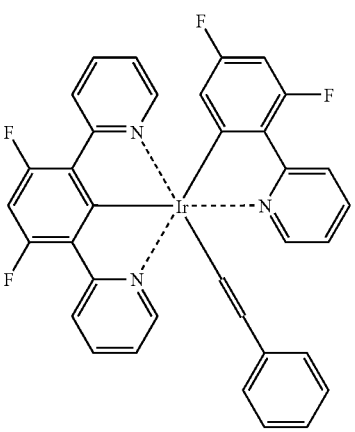
123
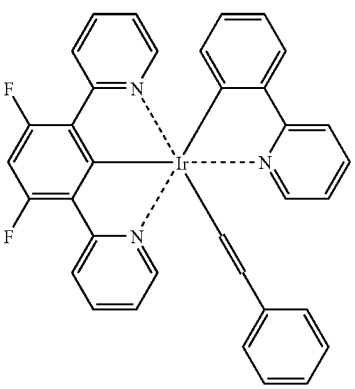

-continued
124
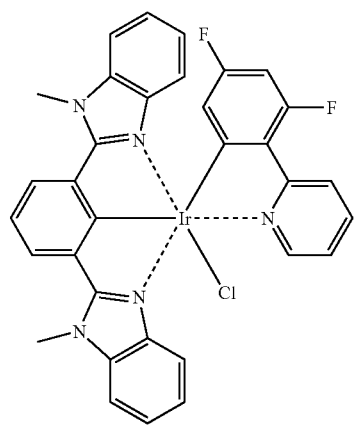
125
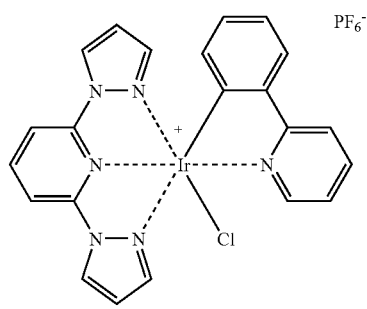
126
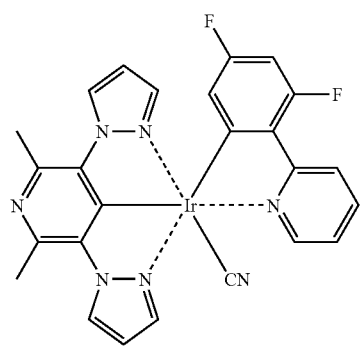
127
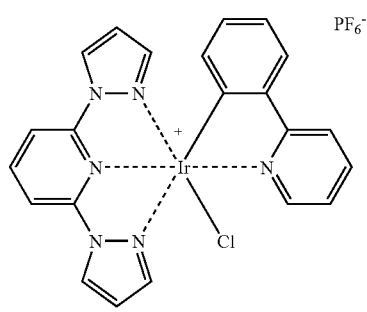
-continued
128
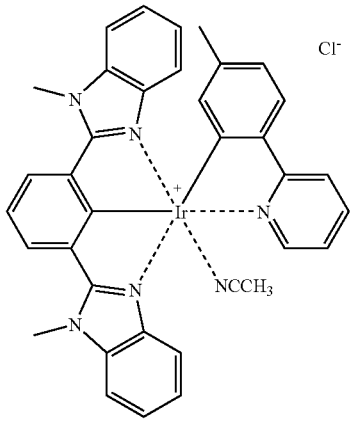
129
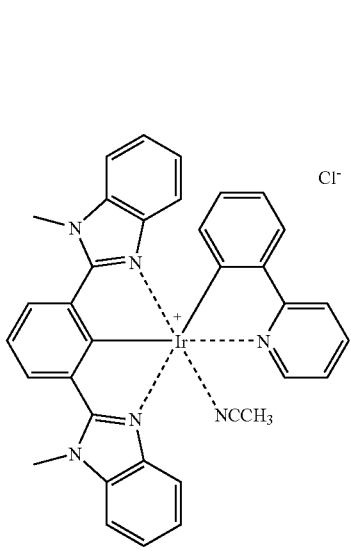
130
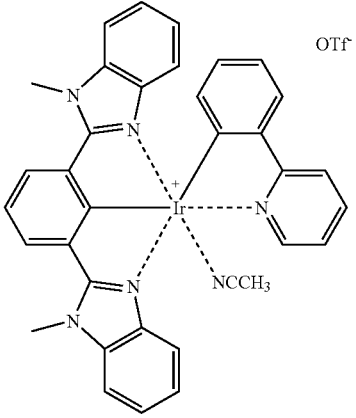

-continued

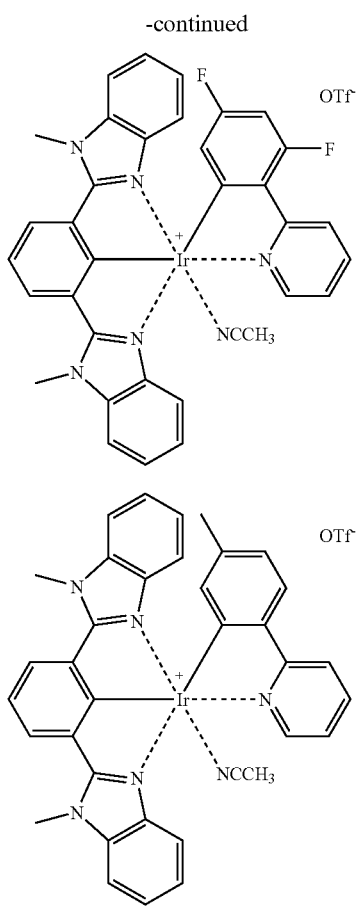

The present invention provides an organic EL device which comprises at least one organic thin film layer sandwiched between a pair of electrode consisting of an anode and a cathode, wherein the organic thin film layer comprises the above metal-complex compound, which emits light by applying an electric voltage between the pair of electrode.

It is preferable for the organic EL device of the present invention that the light emitting layer comprises the metal-complex compound of the present invention, and that it comprises the metal-complex compound of the present invention in an amount of 1 to 30% by weight of total weight of the light emitting layer.

Further, the light emitting layer is usually formed to a thin film by means of vapor deposition or coating, however, it is preferable that the layer comprising the metal-complex compound of the present invention is formed into film by coating because it simplifies the production process.

Typical examples of the construction of the organic EL device include (i) an anode/a light emitting layer/a cathode; (ii) an anode/a hole injecting or a hole transporting layer/a light emitting layer/an electron injecting or an electron transporting layer/a cathode; (iii) an anode/a hole injecting or a hole transporting layer/a light emitting layer/an electron injecting or an electron transporting layer/a cathode; and (iV) an anode/a light emitting layer/an electron injecting or an electron transporting layer/a cathode.

The compound in the present invention may be used in any of the foregoing organic layer, or may be doped into other hole transporting materials, light emitting materials and electron transporting materials. The process for forming the layers in the organic EL device of the present invention is not particularly limited. Except the vapor deposition process, after dissolving the light emitting composition of the present invention or after dissolving the compound forming the composition, the resultant solution may be formed into a light emitting medium or a light emitting layer by means of various wet processes. Namely, they may be formed in accordance with a conventional coating process such as the dipping process, the spin coating process, the casting process, the bar coating process and the roller coating process or with an ink-jet process. The thickness of each layer in the organic thin film layer in the organic EL device of the present invention is not particularly limited. In general, an excessively thin layer tends to have defects such as pin holes, and an excessively thick layer requires a high applied voltage resulting in decreasing the efficiency. Therefore, a thickness within the range of several nanometers to 1 µm is preferable.

Examples of the solvent used for preparing light emitting solution for the light emitting layer include, halogen-based hydrocarbon solvent such as dichloro-methane, dichloroethane, chloroform, tetrachloromethane, tetrachloro ethane, trichloroethane, chlorobenzene, dichlorobenzene, chlorotoluene, etc.; ether-based solvent such as dibutyl ether, tetrahydrofuran, dioxane, anisole, etc.; alcohol-based solvent such as methanol ethanol propanol butanol, pentanol, hexanol, cyclohexanol, methyl cellosolve, ethylcellosolve, ethylene glycol etc.; hydrocarbon-based solvent such as benzene, toluene, xylene, ethyl benzene, hexane, octane, decane, etc.; ester-based solvent such as ethyl acetate, butyl acetate, amyl acetate, etc. Among those, halogen-based hydrocarbon solvent, hydrocarbon-based solvent and ether-based solvent are preferable. Further, the solvent may be used alone, or in combination of two or more kind thereof. Additionally, the employable solvent is not limited to the above examples. Still further, a dopant may be optionally dissolved in advance, into the solution for the light emitting layer.

Electron injecting or transporting material employed for the present invention is not particularly specified and any compound usually employed as electron injecting or transporting material may be employable. Examples include oxadiazole derivatives such as 2-(4-biphenlyl)-5-(4-t-butylphenyl)-1,3,4-oxadiazole, bis {2-(4-t-butylphenyl)-1,3,4-oxadiazole}-m-phenylene, triazole derivatives and quinolinol-based metal-complex. As an inorganic compound for an electron injecting or transporting layer it is preferable to employ an insulating material or a semiconductor.

The electron injecting or transporting layer effectively prevents leak in the electric current and improves the electron injecting capability. It is preferable that at least one metal compound selected from the group consisting of alkali metal chalcogenides, alkaline earth metal chalcogenides, alkali metal halides and alkaline earth metal halides is used as the insulating material. It is preferable that the electron injecting or transporting layer is constituted with the above alkali metal chalcogenide since the electron injecting property can be improved.

Preferable examples of the alkali metal chalcogenide include $Li_2O$, LiO, $Na_2S$ and $Na_2Se$. Preferable examples of the alkaline earth metal chalcogenide include CaO, BaO, SrO, BeO, BaS and CaSe. Preferable examples of the alkali metal halide include LiF, NaF, KF, LiCl, KCl and NaCl. Preferable examples of the alkaline earth metal halide include fluorides such as $CaF_2$, $BaF_2$, $SrF_2$, $MgF_2$ and $BeF_2$ and halides other than the fluorides.

Examples of the semiconductor constituting the electron injecting or transporting layer include oxides, nitrides and nitriding oxides containing at least one element selected from Ba, Ca, Sr, Yb, Al, Ga, In, Li, Na, Cd, Mg, Si, Ta, Sb and Zn, which are used singly or in combination of two or more. It is preferable that the inorganic compound constituting the electron injecting or transporting layer is in the form of a fine crystalline or amorphous insulating thin film. When the electron injecting or transporting layer is constituted with the above insulating thin film, a more uniform thin film can be formed and defective pixels such as dark spots can be decreased Examples of the inorganic compound include the alkali metal chalcogenides, the alkaline earth metal chalcogenides, the alkali metal halides and the alkaline earth metal halides which are described above.

In the present invention, a reductive dopant with a work function of 2.9 eV or smaller may be added in the electron injecting or transporting layer. The reductive dopant used in the present invention is defined as a substance which reduces the electron transporting compound. Accordingly, various compounds having a reductive capability are employable and examples include at least one compound selected from alkali metals, alkali metallic complexes, alkali metal compounds, alkaline earth metals, alkaline earth metallic complexes, alkaline earth metal compounds, rare earth metals, rare earth metallic complexes and rare earth metal compounds.

Examples of the preferable reductive dopant include at least one alkali metal selected from a group consisting of Li (the work function: 2.93 ev), Na (the work function: 2.36 eV), K (the work function: 2.28 eV), Rb (the work function: 2.16 eV) and Cs (the work function: 1.95 eV) or at least one alkaline earth metals selected from a group consisting of Ca (the work function: 2.9 eV), Sr (the work function: 2.0 to 2.5 eV) and Ba (the work function: 2.52 eV); whose work function of 2.9 eV or smaller is particularly preferable. Among those, more preferable reductive dopants include at least one kind selected from the group consisting of K, Rb and Ca, the latter Rb or Cs being farther more preferable and the last Cs being the most preferable. Those alkaline metals have particularly high reducing capability, and only an addition of relatively small amount of them into an electron injection zone enables to expect both improvement of luminance and lifetime extension of the organic EL device.

Further, with regard to the reductive dopant with work function of 2.9 eV or smaller, a combination of two or more kinds of the alkali metal is also preferable, and particularly, combinations containing Ca, for example, combinations of Cs and Na, Cs and K, Cs and Rb, Cs and Na and K are preferable. Containing Cs in combination enables to reveal reducing capability effectively, and the addition into the electron injection zone expects both improvement of luminance and lifetime extension of the organic EL device.

The anode in the organic EL device covers a role of injecting holes into a hole injecting or transporting layer or into a light emitting layer, and it is effective that the anode has a work function of 4.5 eV or greater. Specific examples of the material for the anode include indium tin oxide (ITO) alloy, tin oxide (NESA), gold, silver, platinum, copper, etc. With regard to the cathode, its material preferably has a small work function with the aim of injecting electrons into an electron injecting or transporting layer or into a light emitting layer.

Further in the organic EL device, a hole injecting (transporting) layer may be disposed over the anode. Various organic compounds and polymers usually used for the organic EL device, for example, which are described in Japanese Unexamined Patent Application Laid-Open Nos. Shou 63-295695 and Hei 2-191694 may be employed as the hole injecting or transporting layer. Examples include aromatic tertiary amine, hydrazone derivative, carbazole derivatives, triazole derivatives, imidazole derivatives or polyvinylcarbazole, polyethylendihydroxythiophene poly sulfonic acid (PEDOT/PSS), etc.

Although materials for the cathode of the organic EL device are not particularly specified, examples include indium, aluminium, magnesium, magnesium-indium alloy, magnesium-aluminium alloy, aluminium-lithium alloy, aluminium-scandium lithium alloy, magnesium-silver alloy, etc.

EXAMPLES

The present invention shall be explained below in further details with reference to examples, but the present invention shall by no means be restricted by the following examples.

Synthesis Example 1

Synthesis of Metal-Complex Compound 5

The route for synthesis of the above Metal-Complex Compound 5 is shown as follows:

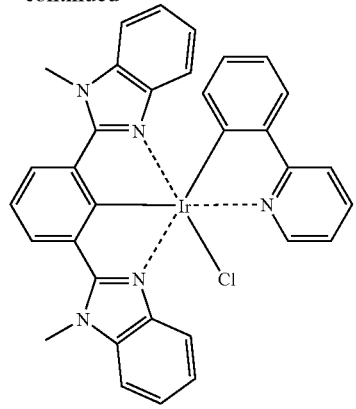

5

(1) Synthesis of mbib

Isophthalic acid in an amount of 18 mmol (3.0 g) and N-methyl-1,2-phenylenediamine in an amount of 36 mmol (4.4 g) were placed into an eggplant type flask with a capacity of 600 milliliter and added polyphosphoric acid in an amount of 75 milliliter. The resultant solution reacted at the temperature of 100° C. for 0.15 hours and further, it was heated at the temperature of 200° C. for 4 hours. After the resultant solution was cooled by leaving it standing, it was added to 600 milliliter of pure water and then, the resultant solution was neutralized with NaOH aqueous solution of 5M until it became pH7, subsequently gathering a precipitated purple solid by filtration, the purple solid was washed with pure water thoroughly. The resultant solid was re-crystallized with the use of methanol and as a result, 3.3 g of aimed mbib was obtained (yield: 54%).

(2) Synthesis of (mbib)IrCl$_2$

Iridic chloride in an amount of 0.27 mmol (0.1 g), mbib in an amount of 0.54 mmol (0.18 g) and methanol in an amount of 15 milliliter were placed into an eggplant type flask having a capacity of 100 milliliter, and the resultant solution was refluxed with heating for 5 hours under the atmospheric nitrogen gas flow. After the resultant solution was cooled by leaving it standing, a precipitate was collected by filtration, the precipitate was washed with the use of methanol and ether, followed by drying and as a result, yellow powders were obtained. The yellow powders were identified by means of Matrix Assisted Laser Desorption/Ionization-time of flight type Mass Spectrometry apparatus (MALDI-MS), and it was confirmed that they were the aimed substance.

(3) Synthesis of Metal-Complex Compound 5

Into an eggplant type flask having a capacity of 100 milliliter, (mbib) IrCl$_2$ in an amount of 0.084 mmol (0.1 g), 2-phenyl pyridine in an amount of 0.168 mmol (0.026 g) and glycerin in an amount of 10 milliliter were placed, and the resultant solution was exposed to microwave irradiation for 6 minutes under an atmospheric nitrogen gas flow. After the resultant solution was cooled by leaving it standing, pure water in an amount of 50 milliliter was added and a precipitate was collected by filtration. Subsequently, the precipitate was washed with the use of hexane and ether, then, dissolving the precipitate into dichloromethane, and after concentrating by pressure reduction, hexane was diffused and as a result, 3 mg of orange powders of Metal-Complex Compound 5 were obtained (yield: 23%). It was confirmed in accordance with Field Desorption Mass Spectrometry ED-MS) that the obtained orange powders were the aimed compound. The result of the measurement in accordance with FD-MS is shown as the following:

FD-MS: calcd for $IrC_{88}H_{25}ClN_5=719$, found, m/z=719 (100)

Further, it was confirmed in accordance with a measurement of light emission spectrum about Metal-Complex Compound 5 obtained, that λ max=552 nm (excitation wavelength: 400 nm) (refer to FIG. 1).

Synthesis Example 2

Synthesis of Metal-Complex Compound 6

The route for synthesis of the above Metal-Complex Compound 6 is shown as follows:

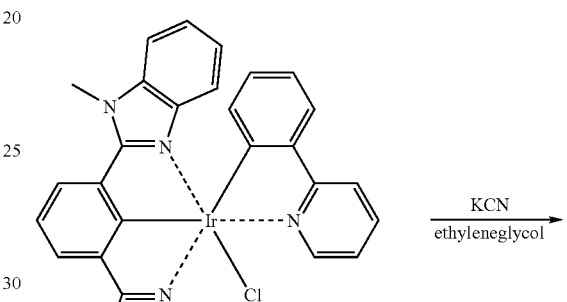

5

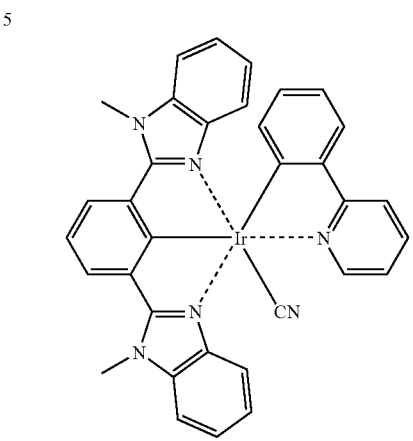

6

Metal-Complex Compound 5 obtained in Synthesis Example 1 in an amount of 0.07 mmol (0.05 g), potassium cyanide in an amount of 0.14 mmol (9.2 mg) and ethylene glycol in an amount of 10 milliliter were placed into an eggplant type flask having a capacity of 100 milliliter, and the resultant solution was exposed to microwave irradiation for a 5 minutes under the atmospheric nitrogen gas flow. After the resultant solution was cooled by leaving it standing, pure water in an amount of 50 milliliter was added and a precipitate was collected by filtration. Subsequently, the precipitate was washed with the use of water and ether, then, dissolving the precipitate into acetonitrile, and after concentrating by pressure reduction, ether was diffused and as a result, 0.03 g of yellow powders of Metal-Complex Compound 6 were obtained (yield: 61%). It was confirmed in accordance with FD-MS that the obtained yellow powders were the aimed compound. The result of the measurement in accordance with FD-MS is shown as the following:

FD-MS: calcd for $IrC_{34}H_{25}N_6$=709, found, m/z=710 (100)

Figure 2:
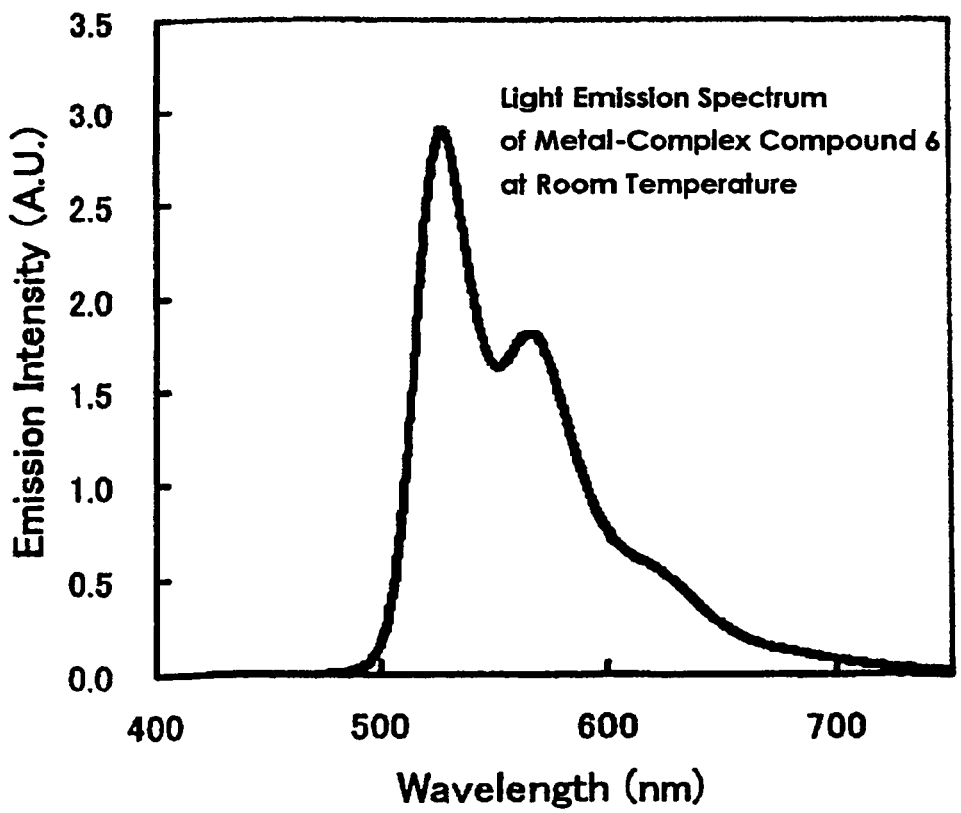
FIG. 2 is a diagram showing a light emission spectrum of Metal-Complex Compound 6 in the present invention at room temperature.

Further, it was confirmed in accordance with a measurement of light emission spectrum about Metal-Complex Compound 6 obtained, that λ max=525 nm (excitation wavelength: 400 nm) (refer to FIG. 2).

Synthesis Example 3

Synthesis of Metal-Complex Compound 20

The route for synthesis of the above Metal-Complex Compound 20 is shown as follows:

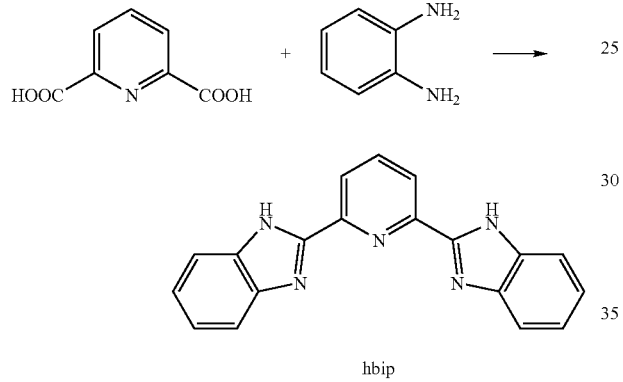

hbip

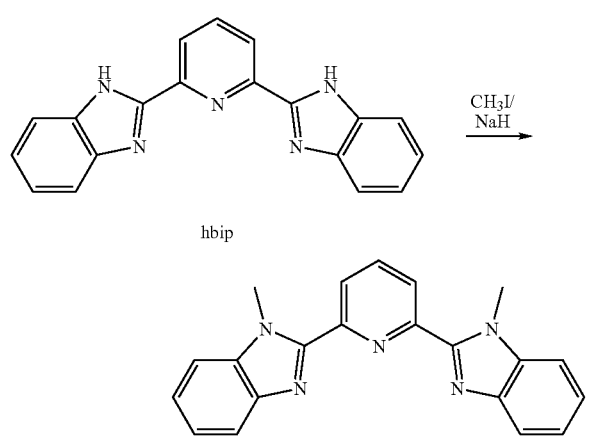

hbip mbip

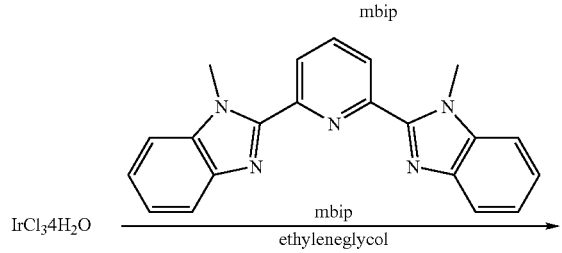

mbip

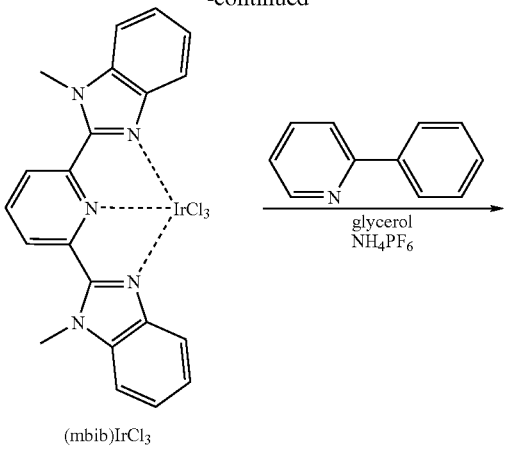

(mbib)IrCl₃

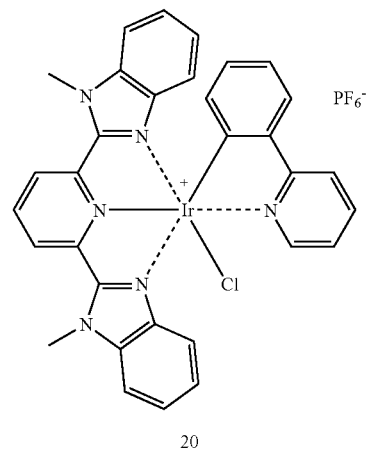

20

(1) Synthesis of hbip

Thoroughly crushed solid dipicolinic acid in an amount of 24 mmol (4.0 g) and o-phenylenediamine in an amount of 48 mmol (5.2 g) were thrown into 40 milliliter of polyphosphoric acid, and the resultant solution was stirred under heating at a temperature of 180° C. for 15 hours. After the resultant solution was cooled by leaving it standing, the resultant homogeneous reaction solution was poured into 500 milliliter of pure water and a precipitate generated. The solution was further stirred in the same condition for 30 minutes. Neutralizing pH of the solution with the use of sodium hydroxide aqueous solution, the precipitate was filtered and dried. After the drying, 6.6 g of white crystal was obtained through re-crystallization from methanol (yield: 88%).

(2) Synthesis of mbip(2,6-bis(N-methyl-2-benzimidazolyl)pyridine)

Under an atmospheric nitrogen gas flow, sodium hydride in an amount of 12.8 mmol (containing 438 mg of 30% liquid paraffin) was placed into a three neck flask having a capacity of 100 milliliter, and adding n-pentane in an amount of 10 milliliter, the resultant solution was stirred at room temperature for 15 minutes. Subsequently, n-pentane was removed and then, after adding n-pentane again, the resultant solution was stirred. Repeating the above operation 4 times totally, the liquid paraffin was removed. Afterwards, the refined sodium hydride was vacuum dried among the flask. Thereafter, adding 10 milliliter of N,N-dimethylformamide and hbip in an amount of 3.2 mmol (1.0 g), the resultant solution was further stirred for 1 hour at a temperature of 35° C. Further adding methyl iodide in an amount of 9.6 mmol (1.36 g), the resultant solution was stirred at a temperature of 40° C. for 3 hours. After the resultant solution was cooled by leaving it standing, 50 milliliter of pure water was added and a generated precipitate was collected by filtration followed by drying, and as a result, 0.87 g of the aimed substance was obtained (yield: 81%).

(3) Synthesis of (mbip)IrCl₃

Iridic chloride in an amount of 0.27 mmol (0.1 g), mbip in an amount of 0.27 mmol and ethylene glycol in an amount of 20 milliliter were placed into an eggplant type flask having a capacity of 100 milliliter, and the resultant solution was stirred with heating at a temperature of 100° C. for 3 hours under the atmospheric nitrogen gas flow. After the resultant solution was cooled by leaving it standing, 40 milliliter of ethanol was added and centrifugal separation of a precipitate was conducted and then, the precipitate was collected by filtration. Further, the precipitate was washed with the use of chloroform and ether, followed by drying, and as a result, 0.1 g of the aimed substance was obtained (yield: 59%).

(4) Synthesis of Metal-Complex Compound 20

Into an eggplant type flask having a capacity of 100 milliliter, (mbip)IrCl₃ in an amount of 0.156 mmol (0.1 g), 2-phenyl pyridine in an amount of 0.234 mmol (0.036 g) and glycerin in an amount of 15 milliliter were placed, and the resultant solution was exposed to microwave irradiation by means of 650 W microwave irradiation equipment (ZMW-007 type; produced by Shikoku Instrumentation Co., Ltd) intermittently 5 times for 3 minutes while stirring under heating. After the resultant solution was cooled to room temperature by leaving it standing, hexafluorophosphate ammonium aqueous solution was added. Afterwards, a supernatant solution was removed with centrifugal separation manipulation, and a precipitate was collected by filtration, washed with the use of hexane and diethyl ether, followed by drying. Dissolving the complex obtained into 30 milliliter of acetonitrile, after conducting celite filtration, the resultant solution was vacuum concentrated. Subsequently, the concentrated solution was re-crystallized with the use of diethyl ether and as a result, 0.08 g of Metal-Complex Compound 20 as red crystals were obtained (yield: 61%). It was confirmed in accordance with FD-MS that the obtained red crystals were the aimed compound. The result of the measurement in accordance with FD-MS is shown as the following:

FD-MS: calcd for $IrC_{32}H_{25}ClF_6N_6P$=866, found, m/z=866 (100)

Figure 3:
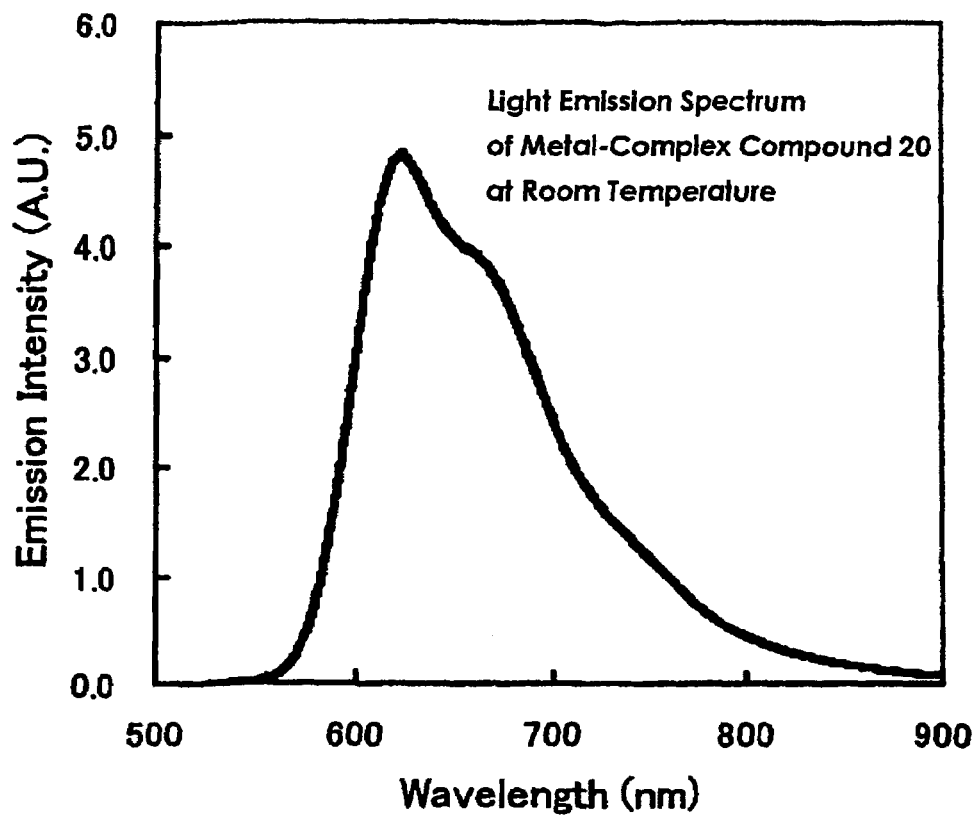
FIG. 3 is a diagram showing a light emission spectrum of Metal-Complex Compound 20 in the present invention at room temperature.

Further, it was confirmed in accordance with a measurement of light emission spectrum about Metal-Complex Compound 20 obtained, that λ max=610 nm (excitation wavelength: 400 nm) (refer to FIG. 3).

Synthesis Example 4

Synthesis of Metal-Complex Compound 23

The route for synthesis of the above Metal-Complex Compound 23 is shown as follows:

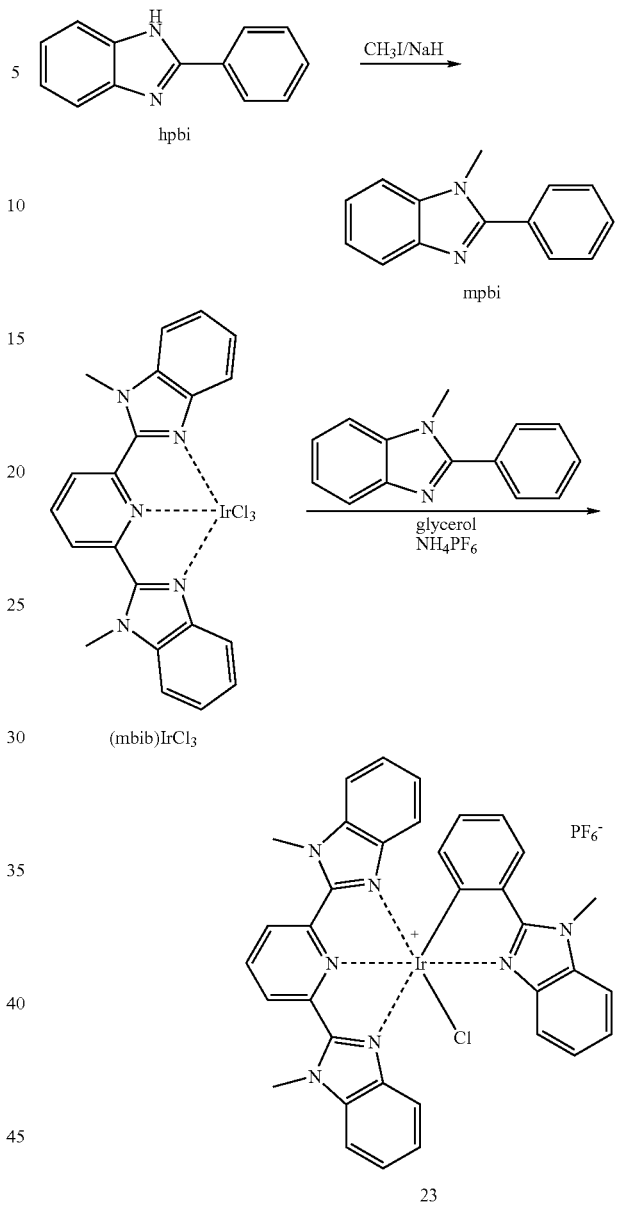

(1) Synthesis of mpbi Ligand

Under an atmospheric nitrogen gas flow, sodium hydride in an amount of 12.8 mmol (containing 438 mg of 30% liquid paraffin) was placed into a three neck flask having a capacity of 100 milliliter, and adding n-pentane in an amount of 10 milliliter, the resultant solution was stirred at room temperature for 15 minutes. Subsequently, n-pentane was removed and then, after adding n-pentane again, the resultant solution was stirred. Repeating the above operation 4 times totally, the liquid paraffin was removed. Afterwards, the refined sodium hydride was vacume dried among the flask. Then, adding N,N-dimethylformamide in an amount of 15 milliliter and hpbi in an amount of 7.7 mmol (1.5 g), the resultant solution was stirred at a temperature of 35° C. for 1 hour and, further adding methyl iodide in an amount of 9.6 mmol (1.36 g), the resultant solution was further stirred at a temperature of 40° C. for 3 hours. After the resultant solution was cooled by leaving it standing, the solvent was removed by pressure reduction, and adding pure water, the resultant solution was stirred. Further, after adding dichloromethane, the resultant solution was divided by extraction. Gathering an organic layer, and after dehydration with the use of sodium sulfate, the solvent was concentrated by pressure reduction. A white precipitate generated by adding n-hexane was separated by filtration and 0.99 g of the aimed substance was obtained (yield: 62%).

(2) Synthesis of Metal-Complex Compound 23

Similar reaction as Synthesis Example 3 (4) was carried out except that mpbi was used instead of 2-phenyl pyridine, and 0.1 g of the aimed compound as red complex was obtained (yield: 41%). It was confirmed in accordance with FD-MS that the obtained red complex was the aimed compound. The result of the measurement in accordance with FD-MS is shown as the following:

FD-MS: calcd for $IrC_{35}H_{28}F_6N_7P=919$, found, m/z=919 (100)

Figure 4:
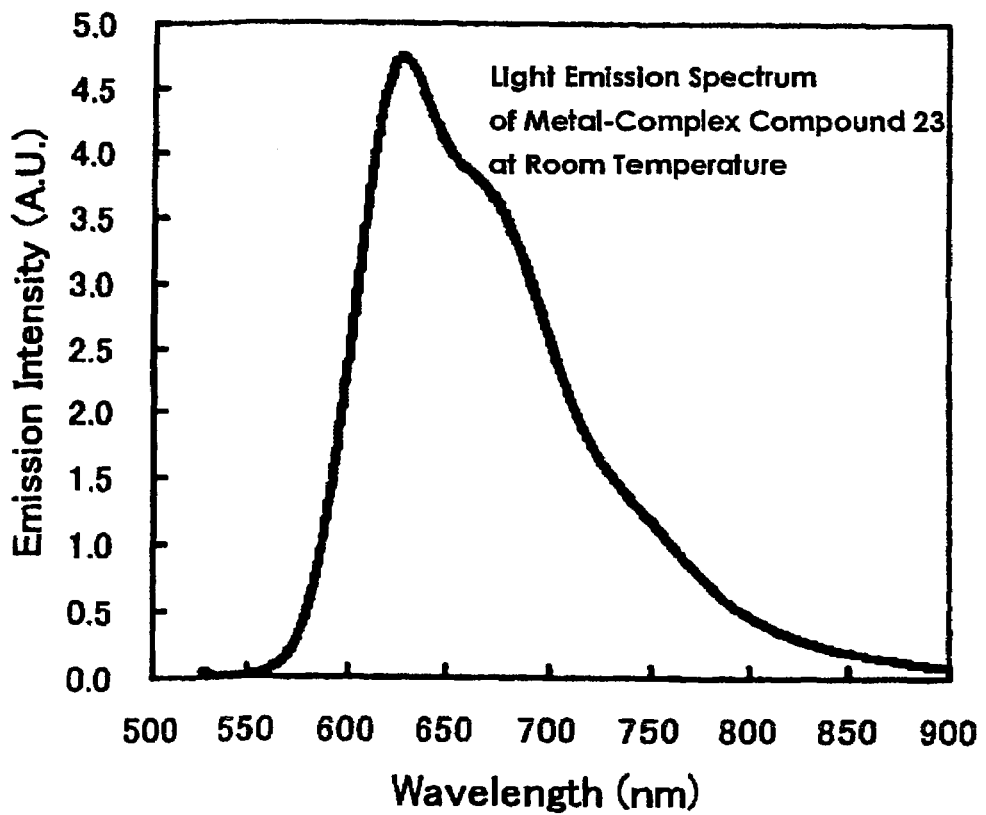
FIG. 4 is a diagram showing a light emission spectrum of Metal-Complex Compound 23 in the present invention at room temperature.

Further, it was confirmed in accordance with a measurement of light emission spectrum about Metal-Complex Compound 23 obtained, that λ max=614 nm (excitation wavelength: 400 nm) (refer to FIG. 4).

Synthesis Example 5

Synthesis of Metal-Complex Compound 124

The route for synthesis of the above Metal-Complex Compound 124 is shown as follows:

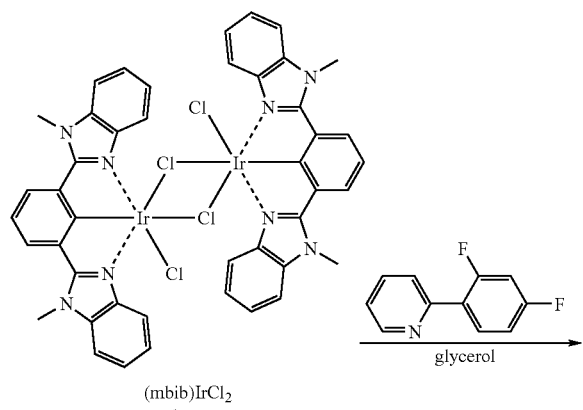

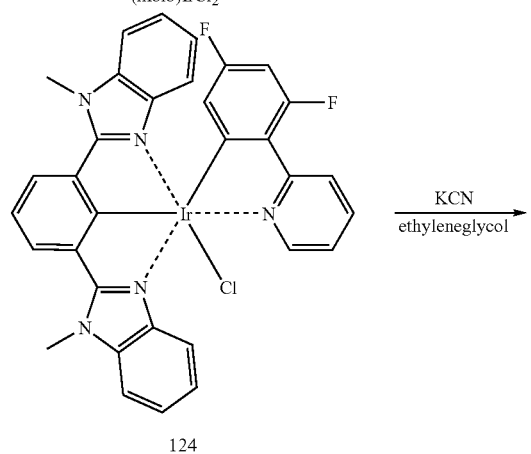

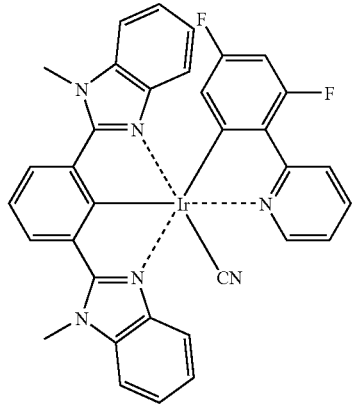

7

Synthesis of (mbib)IrCl$_2$ was conducted in the same manner as described in Synthesis Example 1. Into an eggplant type flask having a capacity of 100 milliliter, (mbib)IrCl$_2$ in an amount of 0.084 mmol (0.1 g), 2-phenyl pyridine in an amount of 0.17 mmol (0.033 g) and glycerin in an amount of 10 milliliter were placed, and the resultant solution was exposed to microwave irradiation for 8 minutes under an atmospheric nitrogen gas flow. After the resultant solution was cooled by leaving it standing, 50 milliliter of pure water was added and a precipitate was collected by filtration, washed with the use of hexane and ether and then, dissolved into methylene chloride. After concentrating the resultant solution by pressure reduction, ether was diffused and as a result, 0.04 g of orange crystals as Metal-Complex Compound 124 were obtained (yield: 32%). It was confirmed in accordance with FD-MS that the obtained orange crystals were the aimed compound. The result of the measurement in accordance with FD-MS is shown as the following:

FD-MS: calcd for $IrC_{33}H_{23}ClF_2N_5=755$, found, m/z=755 (100)

Figure 5:
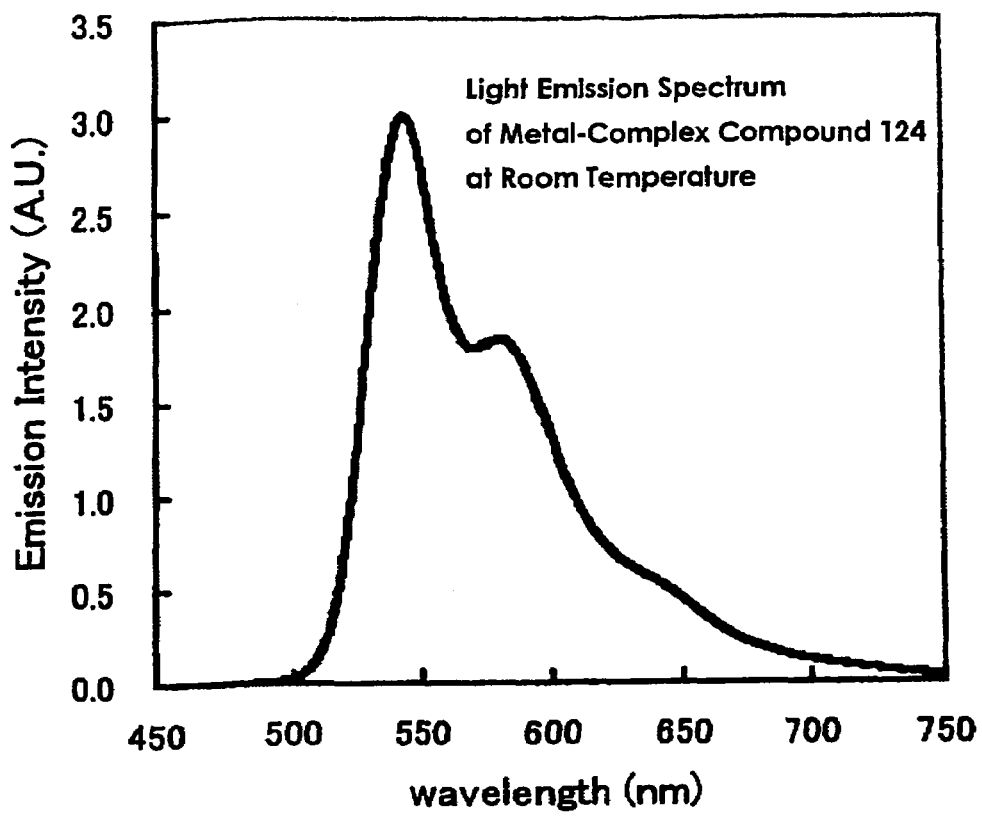
FIG. 5 is a diagram showing a light emission spectrum of Metal-Complex Compound 124 in the present invention at room temperature.

Further, it was confirmed in accordance with a measurement of light emission spectrum about Metal-Complex Compound 124 obtained, that λ max=540 nm (excitation wavelength: 400 nm) (refer to FIG. 5).

Synthesis Example 6

Synthesis of Metal-Complex Compound 7

As described in the route for Synthesis Example 5, Metal-Complex Compound 124 in an amount of 0.07 mmol (0.053 g), potassium cyanide in an amount of 0.14 mmol (9.2 mg) and ethylene glycol in an amount of 10 milliliter were placed into an eggplant type flask having a capacity of 100 milliliter, and the resultant solution was exposed to microwave irradiation for 5 minutes under the atmospheric nitrogen gas flow. After the resultant solution was cooled by leaving it standing, pure water in an amount of 50 milliliter was added and a precipitate was collected by filtration. Subsequently, the precipitate was washed with the use of water and ether, then, dissolving the precipitate into methylene chloride, and after concentrating by pressure reduction, ether was diffused and as a result, 0.037 g of yellow powders as Metal-Complex Compound 7 were obtained (yield: 72%). It was confirmed in accordance with Matrix-Assisted Laser Desorption Ionization-Mass Spectrum (MALDI-MS) measurement that the yellow powders are the aimed compound. The result of the measurement in accordance with MALDI-MS is shown as the following:

MALDI-MS: calcd for $IrC_{34}H_{23}N_6F_2$=746, found, m/z=746 (100)

Figure 6:
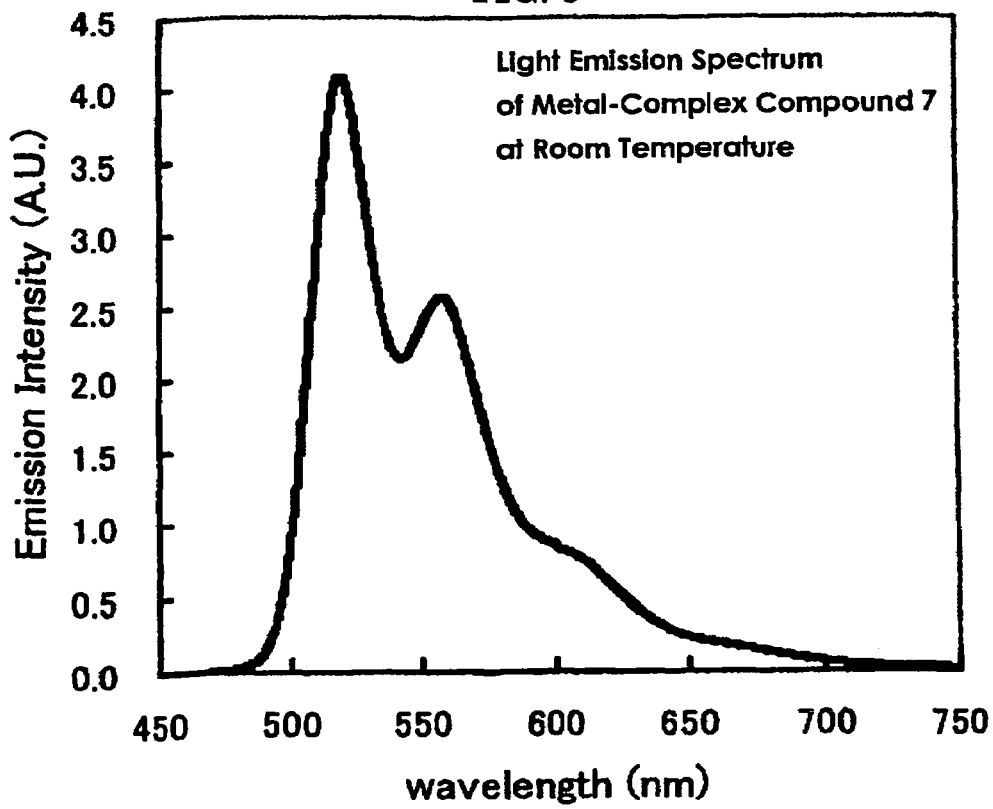
FIG. 6 is a diagram showing a light emission spectrum of Metal-Complex Compound 7 in the present invention at room temperature.

Further, it was confirmed in accordance with a measurement of light emission spectrum about Metal-Complex Compound 7 obtained, that λ max=517 nm (excitation wavelength: 400 nm) (refer to FIG. 6).

Synthesis Example 7

Synthesis of Metal-Complex Compound 103

The route for synthesis of the above Metal-Complex Compound 103 is shown as follows:

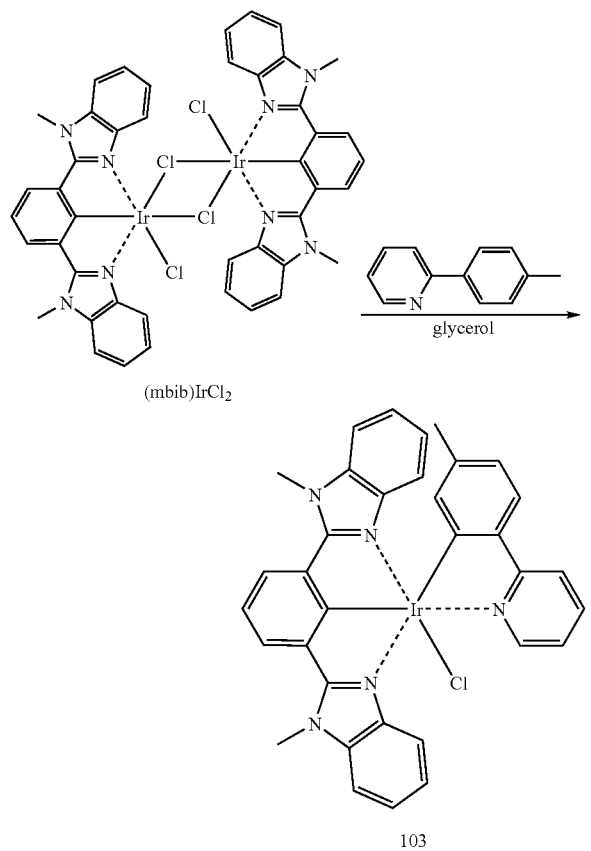

Synthesis of (mbib)IrCl$_2$ was conducted in the same manner as described in Synthesis Example 1. Into an eggplant type flask having a capacity of 100 milliliter, (mbib)IrCl$_2$ in an amount of 0.084 mmol (0.1 g), 2-(4'-methylphenyl) pyridine in an amount of 0.17 mmol (0.029 g) and glycerin in an amount of 10 milliliter were placed, and the resultant solution was exposed to microwave irradiation for 6 minutes under an atmospheric nitrogen gas flow. After the resultant solution was cooled by leaving it standing, 50 milliliter of pure water was added and a precipitate was collected by filtration, washed with the use of hexane and ether and then, dissolved into methylene chloride. After concentrating the resultant solution by pressure reduction, ether was diffused and as a result, 0.039 g of orange crystals as Metal-Complex Compound 103 was obtained (yield: 32%). It was confirmed in accordance with Electrospray Ionization-Mass Spectrum (ESI-MS) measurement that the orange crystals were the aimed compound. The result of the measurement in accordance with ESI-MS is shown as the following:

ESI-MS: calcd for $IrC_{34}H_{27}ClN_5$=733, found, m/z 733 (100)

Figure 7:
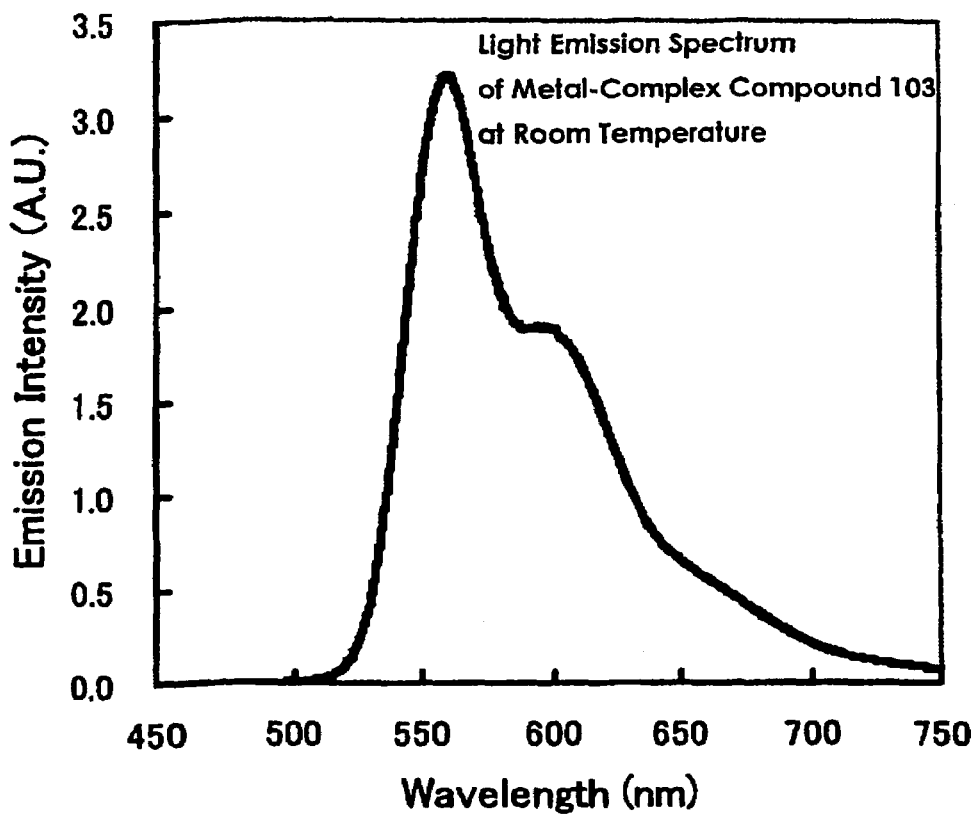
FIG. 7 is a diagram showing a light emission spectrum of Metal-Complex Compound 103 in the present invention at room temperature.

Further, it was confirmed in accordance with a measurement of light emission spectrum about Metal-Complex Compound 103 obtained, that λ max=556 nm (excitation wavelength: 400 nm) (refer to FIG. 7).

Synthesis Example 8

Synthesis of Metal-Complex Compound 130

The route for synthesis of the above Metal-Complex Compound 130 is shown as follows:

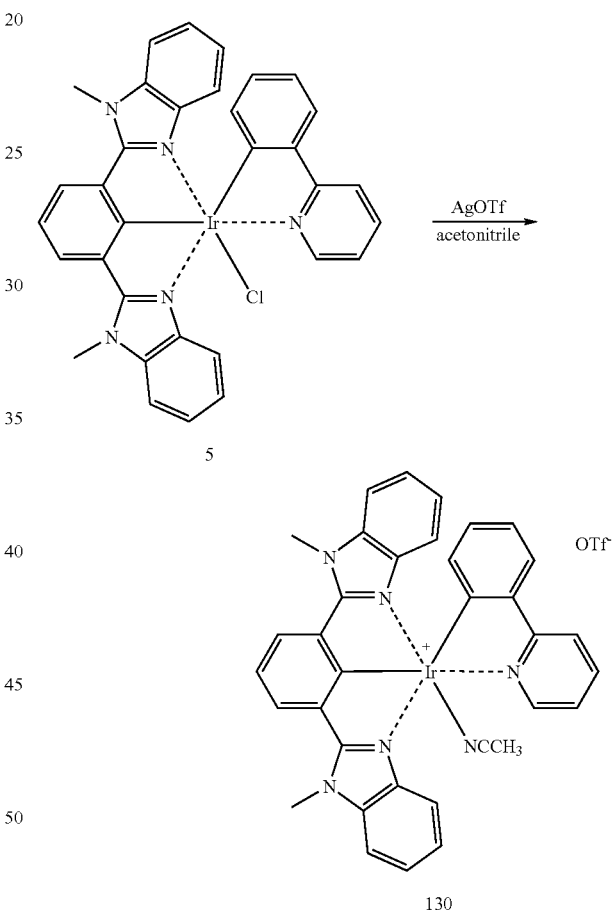

Metal-Complex Compound 5 in an amount of 0.07 mmol (0.05 g), silver trifluoromethyl sulfide in an amount of 0.14 mmol (0.036 g) and acetonitrile in an amount of 20 milliliter were placed into an eggplant type flask having a capacity of 100 milliliter and the resultant solution was refluxed with heating for 3 hours under an atmospheric nitrogen gas flow. After the resultant solution was cooled by leaving it standing, the resultant reaction solution was filtered by means of a celite and concentrated by pressure reduction, then, ether was diffused and as a result, 0.04 g of yellow powders as Metal-Complex Compound 130 were obtained yield: 92%). It was confirmed in accordance with ESI-MS that the yellow powders were the aimed compound. The result of the measurement in accordance with ESI-MS is shown as the following:

ESI-MS: calcd for $IrC_{35}H_{28}N_6$=725, found, m/z 725 (100)

Further, it was confirmed in accordance with a measurement of light emission spectrum about Metal-Complex Compound 130 obtained, that λ max 513 nm (excitation wavelength: 400 nm).

Synthesis Example 9

Synthesis of Metal-Complex Compound 131

The route for synthesis of the above Metal-Complex Compound 131 is shown as follows:

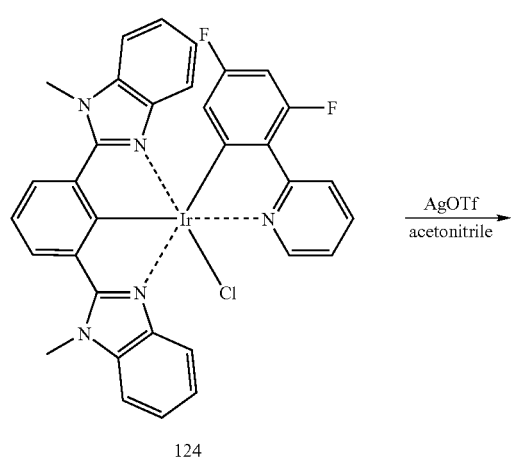

124

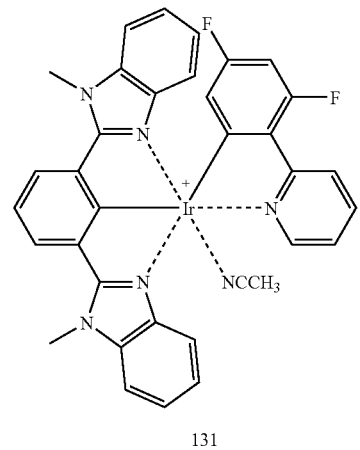

131

ESI-MS: calcd for $IrC_{35}H_{26}N_6F_2$=761, found, m/z=761 (100)

It was confirmed in accordance with a measurement of light emission spectrum about Metal-Complex Compound 131 obtained, that λ max=502 nm (excitation wavelength: 400 nm).

Synthesis Example 10

Synthesis of Metal-Complex Compound 132

The route for synthesis of the above Metal-Complex Compound 132 is shown as follows:

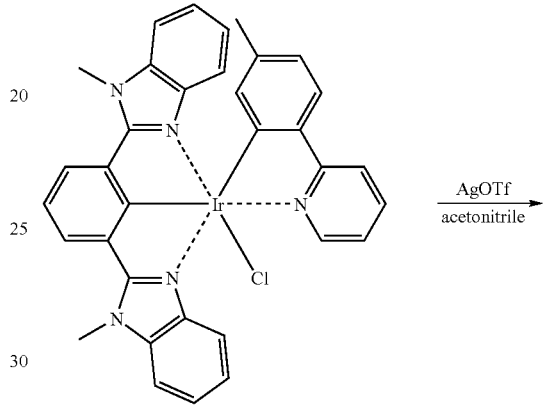

103

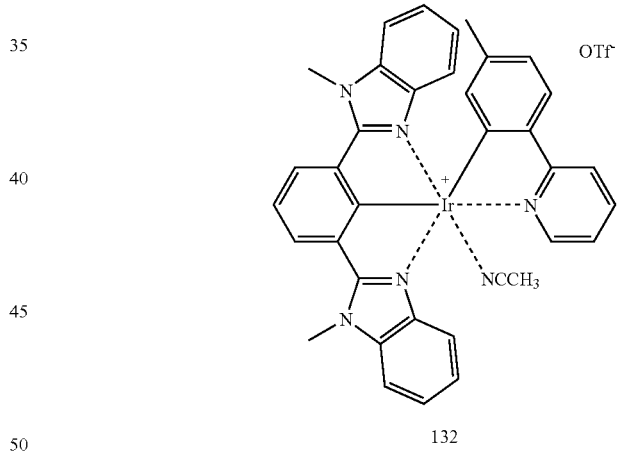

132

Metal-Complex Compound 124 in an amount of 0.07 mmol (0.053 g), silver trifluoromethyl sulfide in an amount of 0.14 mmol (0.036 g) and acetonitrile in an amount of 20 milliliter were placed into an eggplant type flask having a capacity of 100 milliliter and the resultant solution was refluxed with heating for 3 hours under an atmospheric nitrogen gas flow. After the resultant solution was cooled by leaving it standing, the resultant reaction solution was filtered by means of a celite and concentrated by pressure reduction, then, ether was diffused and as a result, 0.04 g of yellow powders as Metal-Complex Compound 131 were obtained (yield: 95%). It was confirmed in accordance with ESI-MS that the yellow powders were the aimed compound. The result of the measurement in accordance with ESI-MS is shown as the following:

Metal-Complex Compound 103 in an amount of 0.07 mmol (0.051 g), silver trifluoromethyl sulfide in an amount of 0.14 mmol (0.036 g) and acetonitrile in an amount of 20 milliliter were placed into an eggplant type flask having a capacity of 100 milliliter and the resultant solution was refluxed with heating for 3 hours under an atmospheric nitrogen gas flow. After the resultant solution was cooled by leaving it standing, the resultant reaction solution was filtered by means of a celite and concentrated by pressure reduction, then, ether was diffused and as a result, 0.046 g of yellow powders as Metal-Complex Compound 132 were obtained (yield: 88%). It was confirmed in accordance with ESI-MS that the yellow powders were the aimed compound. The result of the measurement in accordance with ESI-MS is shown as the following:

ESI-MS: calcd for IrC$_{36}$H$_{30}$N$_6$=739, found, m/z=739 (100)

It was confirmed in accordance with a measurement of light emission spectrum about Metal-Complex Compound 132 obtained, that λ max=512 nm (excitation wavelength: 400 nm).

Synthesis Example 11

Synthesis of Metal-Complex Compound 105

The route for synthesis of the above Metal-Complex Compound 105 is shown as follows:

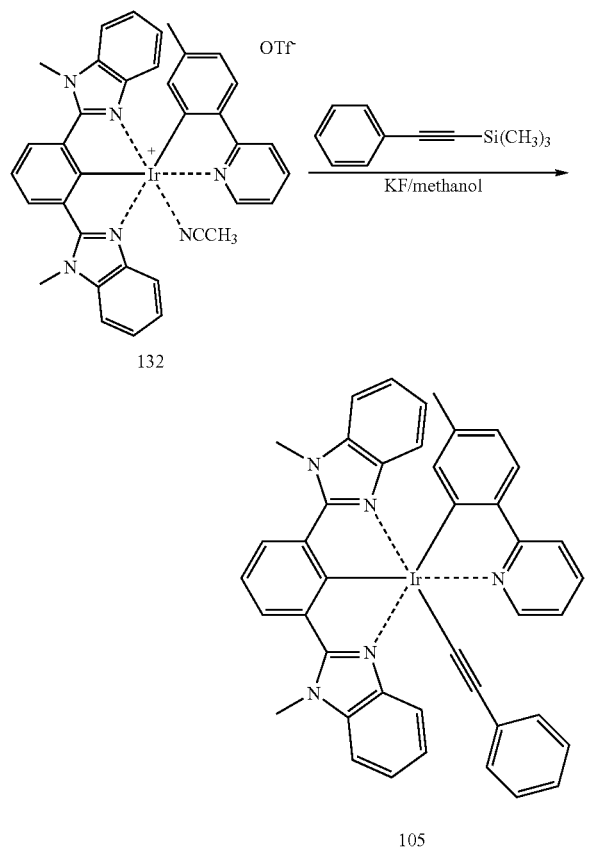

Potassium fluoride in an amount of 0.339 mmol (0.02 g), 1-trimethylsilyl-2-phenyl acetylene in an amount of 0.113 mmol (0.02 g) and methanol in an amount of 10 milliliter were placed into an eggplant type flask having a capacity of 100 milliliter, and the resultant solution was stirred at room temperature for 30 minutes under an atmospheric nitrogen gas flow. Subsequently, adding Metal-Complex Compound 132 in an amount of 0.056 mmol (0.05 g), the resultant solution was refluxed under heating for 2 hours. After the resultant solution was cooled by leaving it standing, a generated precipitate was collected by filtration, washed with the use of methanol and ether and then, dissolved into methylene chloride, and after ether was diffused, 0.024 g of orange powders as Metal-Complex Compound 105 were obtained (yield: 54%). It was confirmed in accordance with ESI-MS that the orange powders were the aimed compound. The result of the measurement in accordance with ESI-MS is shown as the following:

ESI-MS: calcd for IrC$_{42}$H$_{32}$N$_5$=799, found, m/z 799 (100)

Figure 8:
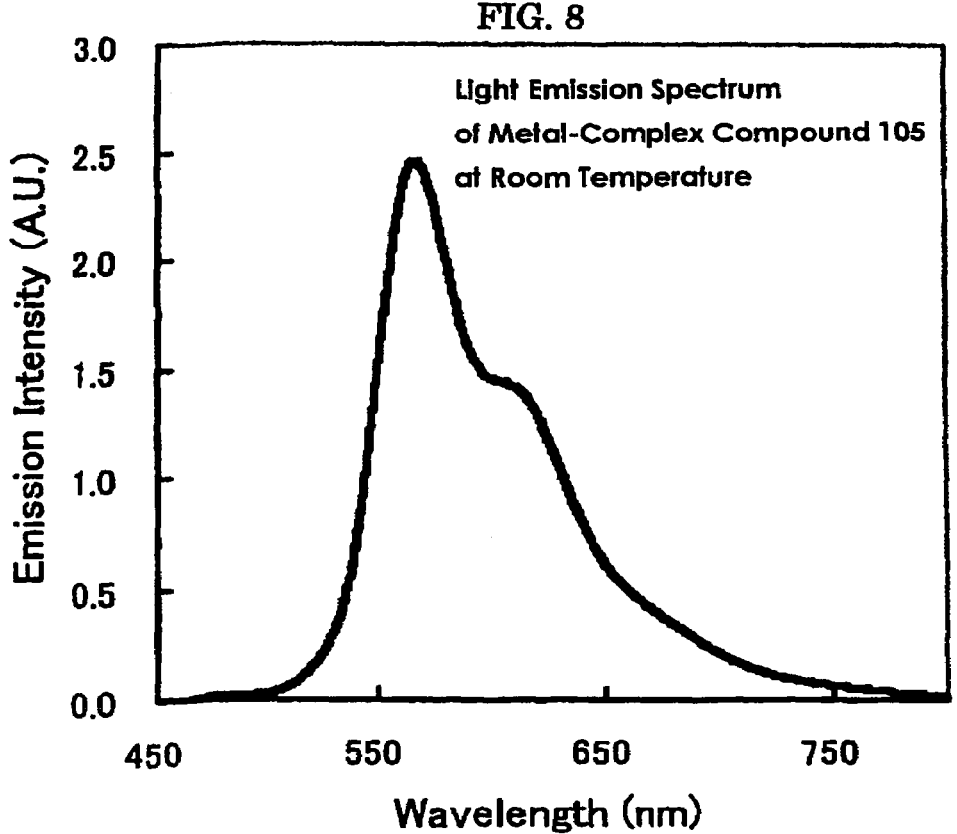
FIG. 8 is a diagram showing a light emission spectrum of Metal-Complex Compound 105 in the present invention at room temperature.

It was confirmed in accordance with a measurement of light emission spectrum about Metal-Complex Compound 105 obtained, that λ max=568 nm (excitation wavelength: 400 nm) (refer to FIG. 8).

Synthesis Example 12

Synthesis of Metal-Complex Compound 32

The route for synthesis of the above Metal-Complex Compound 32 is shown as follows:

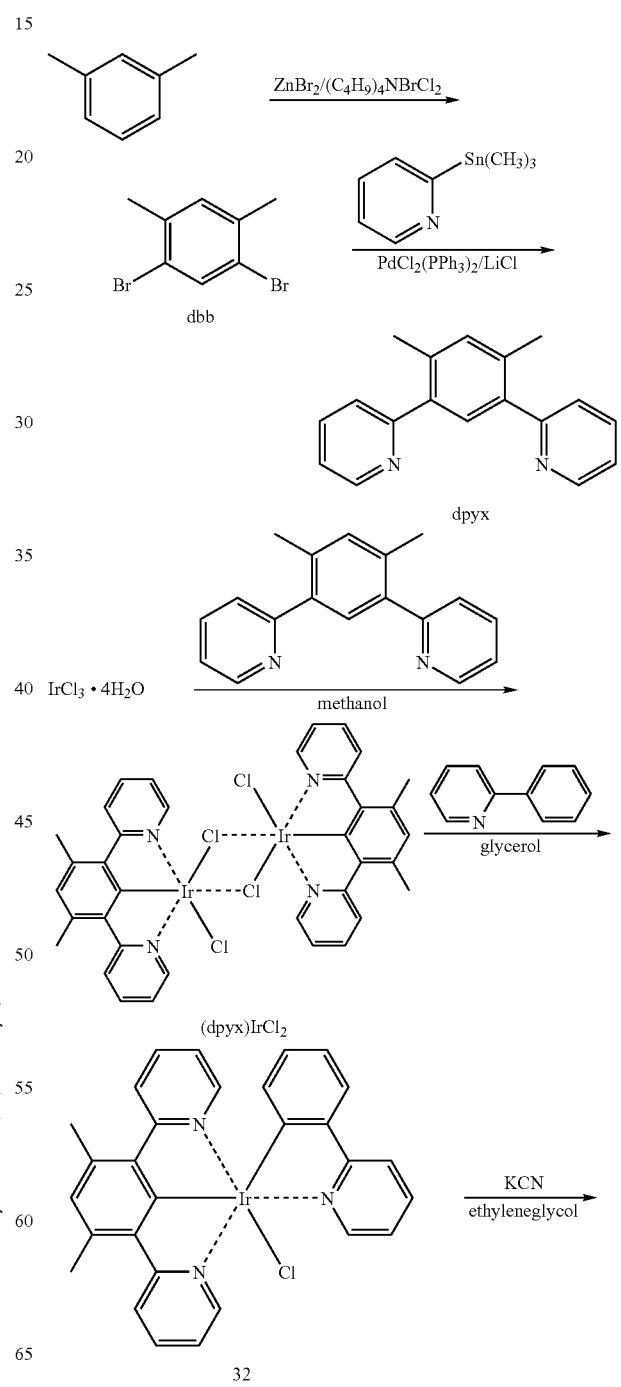

-continued

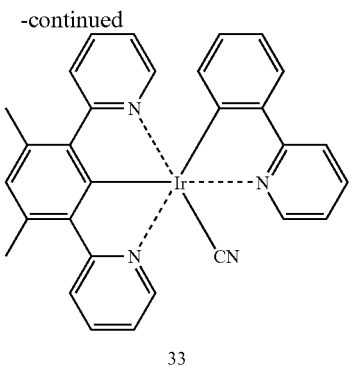

33

(1) Synthesis of dbb

Into an eggplant type flask having a capacity of 200 milliliter, m-xylene in an amount of 7.5 mmol (0.795 g), zinc bromide in an amount of 33.6 mmol (7.56 g) and nitromethane in an amount of 60 milliliter were placed, and the resultant solution was stirred at room temperature, followed by adding 15.8 mmol (6.19 g) of tetra n-butylammonium dichlorobromate little by little while dividing into several times. After stirring the resultant solution at room temperature for 44 hours, sodium sulfite aqueous solution was added and the solution was extracted with the use of ether. An organic layer was removed through pressure reduction and as a result, a yellow solid was obtained. After pouring hexane on the yellow solid, the resultant mixture was heated up to the temperature of about 85° C., and the resultant solution was filtered. The filtrate was removed through pressure reduction and as a result, 0.945 g of white solid as the aimed substance dbb was obtained (yield: 48%).

(2) Synthesis of dpyx

Into an eggplant type flask having a capacity of 200 milliliter, dbb in an amount of 5.11 mmol (1.35 g), (2-pyridyl) trimethyl tin in an amount of 15.3 mmol (3.71 g), Pd (PPh$_3$)$_2$Cl$_2$ in an amount of 0.408 mmol (0.286 g), lithium chloride in an amount of 51.1 mmol (2.17 g) and toluene as a solvent in an amount of 20 milliliter were placed and the resultant solution was refluxed for 3 days. After the resultant solution was cooled by leaving it standing, saturated potassium fluoride aqueous solution was added and the resultant solution was stirred for 30 minutes. After filtering the resultant solution, dichloromethane and 5% sodium hydrogen carbonate aqueous solution were added to the filtrate and the resultant solution was extracted. Adding sodium sulfate into an organic layer and dehydrating the resultant mixture, the organic layer was removed through pressure reduction, and the remained substance was refined by means of silica gel column chromatography (hexane:ether=4:1). After re-crystallizing the resultant substance with the use of heated hexane, white crystals of dpyx in an amount of 0.31 g was obtained yield: 33%). m.p.: 89 to 90° C.

(3) Synthesis of (dpyx)IrCl$_2$

Iridic chloride in an amount of 0.92 mmol (0.342 g), dpyx in an amount of 0.92 mmol (0.24 g) and methanol in an amount of 20 milliliter were placed into an eggplant type flask having a capacity of 100 milliliter, and the resultant solution was refluxed for a day under the atmospheric nitrogen gas flow. After the resultant solution was cooled by leaving it standing, the solution was filtered and dried and as a result, 0.18 g of yellow crystals as the aimed substance was obtained (yield: 37%).

(4) Synthesis of Metal-Complex Compound 32

Into an eggplant type flask having a capacity of 100 milliliter, (dpyx)IrCl$_2$ in an amount of 0.096 mmol (0.1 g), 2-phenyl pyridine in an amount of 0.234 mmol (0.036 g) and glycerin in an amount of 20 milliliter were placed, and the resultant solution was exposed to microwave irradiation by means of 660 W microwave irradiation equipment (ZMW-007 type; produced by Shikoku Instrumentation Co., Ltd) for 10 minutes, followed by refluxing under heating. After the resultant solution was cooled to room temperature by leaving it standing, 50 milliliter of pure water was added and a precipitate was collected by filtration, washed with the use of hexane and diethylether and then, the resultant solution was refined with the use of methylene chloride and as a result, yellow crystals of Metal-Complex Compound 32 in an amount of 0.064 g were obtained (yield: 52%). It was confirmed in accordance with ESI-MS that the yellow crystals were the aimed compound. The result of the measurement in accordance with ESI-MS is shown as the following:

ESI-MS: calcd for IrC$_{29}$H$_{28}$ClN$_3$=641, found, m/z=641 (100)

$^1$H-NMR (CD$_3$CN): δ 9.84 (d, 1H), 8.07 (d, 1H), 7.99 (d, 2H), 7.96 (t, 1H), 7.52-7.57 (m, 6H), 6.84 (s, 1H), 6.76 (t, 2H), 6.55 (t, 1H), 6.34 (t, 1H), 5.70 (d, 1H), 2.72 (s, 6H)

Figure 9:
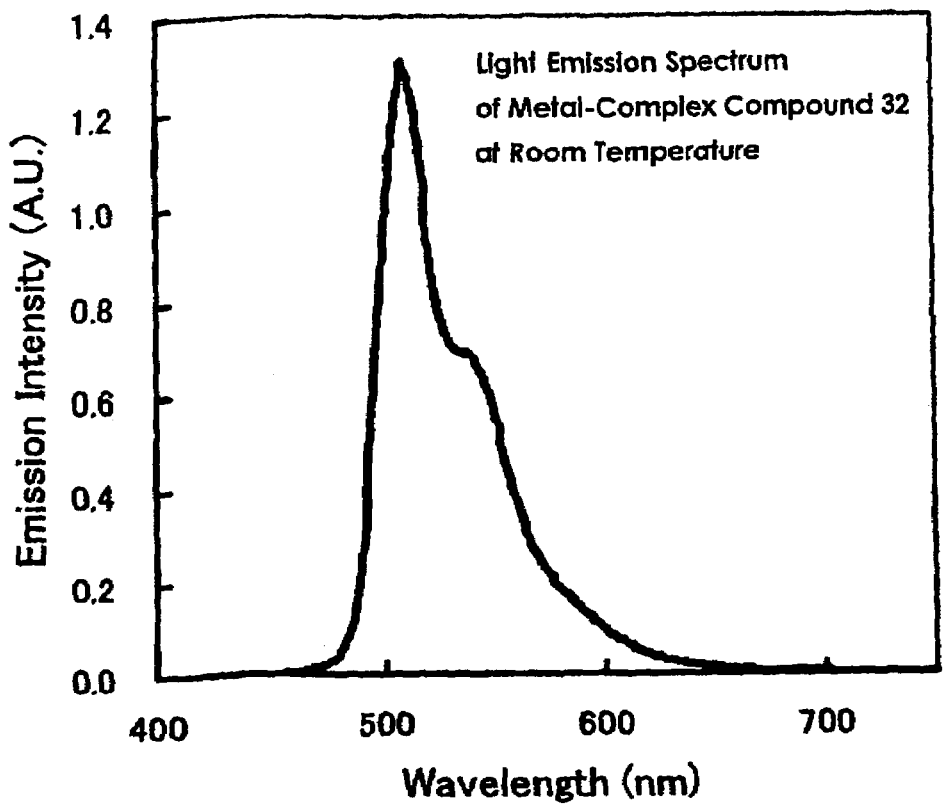
FIG. 9 is a diagram showing a light emission spectrum of Metal-Complex Compound 32 in the present invention at room temperature.

It was confirmed in accordance with a measurement of light emission spectrum about Metal-Complex Compound 32 obtained, that λ man 504 nm (excitation wavelength: 400 nm) (refer to FIG. 9).

Synthesis Example 13

Synthesis of Metal-Complex Compound 33

Metal-Complex Compound 32 in an amount of 0.078 mmol (0.05 g), potassium cyanide in an amount of 0.156 mmol (0.01 g) and ethylene glycol in an amount of 10 milliliter were placed into an eggplant type flask having a capacity of 100 milliliter, and the resultant solution was exposed to microwave irradiation for 2.5 minutes under the atmospheric nitrogen gas flow, followed by refluxing under heating. After the resultant solution was cooled to room temperature by leaving it standing, 50 milliliter of pure water was added and a precipitate was collected by filtration, washed with the use of hexane and diethylether and then, the resultant solution was re-crystallized with the use of methylene chloride and as a result, orange crystals of Metal-Complex Compound 33 in an amount of 0.032 g were obtained (yield: 65%). It was confirmed in accordance with ESI-MS that the orange crystals were the aimed compound. The result of the measurement in accordance with ESI-MS is shown as the following:

ESI-MS: calcd for IrC$_{80}$H$_{23}$N$_4$=631, found, m/z=631 (100)

$^1$H-NMR (CD$_8$CN): δ 9.79 (d, 1H), 8.14 (d, 1H), 8.10 (d, 2H), 8.05 (t, 1H), 7.72 (d, 2H), 7.65 (dt, 3H), 7.56 (t, 1H), 6.96 (s, 1H), 6.82 (t, 2H), 6.68 (t, 1H), 6.46 (t, 1H), 5.75 (d, 1H), 2.80 (s, 6H)

Figure 10:
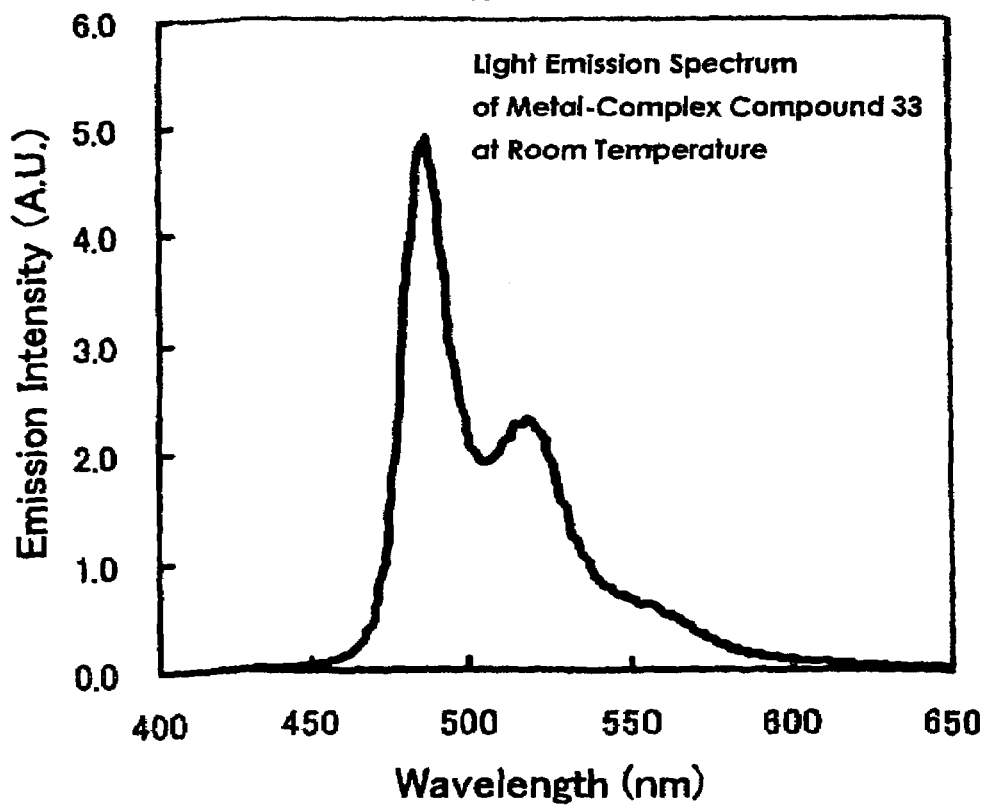
FIG. 10 is a diagram showing a light emission spectrum of Metal-Complex Compound 33 in the present invention at room temperature.

It was confirmed in accordance with a measurement of light emission spectrum about Metal-Complex Compound 33 obtained, that λ max=484 nm (excitation wavelength: 400 nm) (refer to FIG. 10).

Synthesis Example 14

Synthesis of Metal-Complex Compound 16

The route for synthesis of the above Metal-Complex Compound 16 is shown as follows:

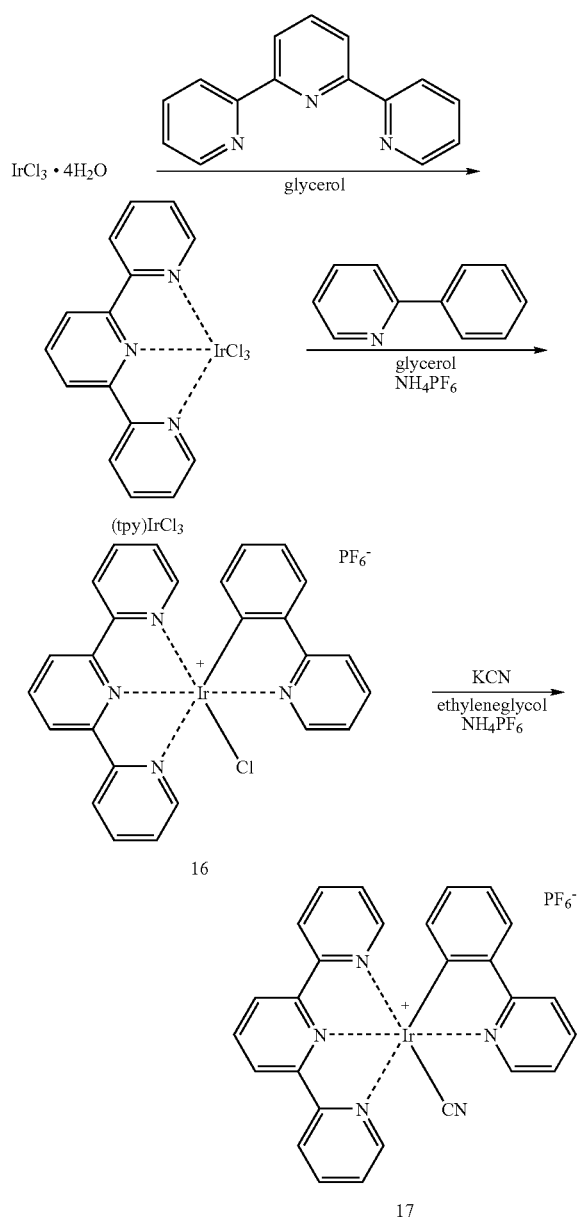

(1) Synthesis of (tpy)IrCl$_3$

Iridic chloride in an amount of 0.27 mmol (0.1 g), 2,2'6', 6"terpyridine in an amount of 0.27 mmol (0.06 g) and ethylene glycol in an amount of 20 milliliter were placed into an eggplant type flask having a capacity of 100 milliliter, and the resultant solution was stirred with heating at a temperature of 100° C. for 3 hours under the atmospheric nitrogen gas flow. After the resultant solution was cooled by leaving it standing, 40 milliliter of ethanol was added and centrifugal separation of a precipitate was conducted and then, the precipitate was collected by filtration. The precipitate was washed with the use of chloroform and ether, followed by drying, and as a result, 0.12 g of the aimed substance was obtained (yield: 82%).

(2) Synthesis of Metal-Complex Compound 16

Into an eggplant type flask having a capacity of 100 milliliter, complex (tpy) IrCl$_3$ in an amount of 0.38 mmol (0.20 g), 2-phenyl pyridine in an amount of 0.46 mmol (0.07 g) and glycerin in an amount of 20 milliliter were placed, and the resultant solution was exposed to microwave irradiation for 12 minutes under an atmospheric nitrogen gas flow, allowed by refluxing under heating. After the resultant solution was cooled by leaving it standing, hexafluorophosphate ammonium aqueous solution was added and the generated precipitate was separated by filtration and washed with the use of hexane. The resultant crystals were re-crystallized with the use of acetonitrile/ether, and as a result, yellow crystals of Metal-Complex Compound 16 in an amount of 0.245 g were obtained (yield: 84%). It was confirmed in accordance with ESI-MS that the yellow crystals were the aimed compound. The result of the measurement in accordance with ESI-MS is shown as the following:

ESI-MS: calcd for IrC$_{26}$H$_{19}$ClF$_6$N$_4$P=760, found, m/z=760 (100)

Figure 11:
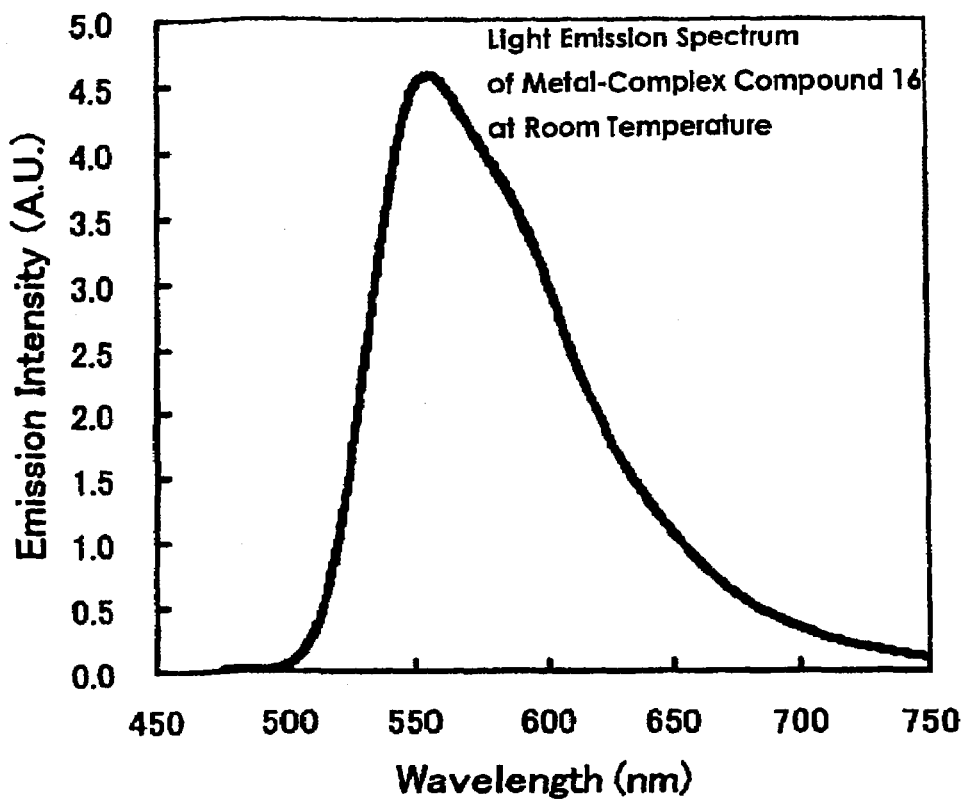
FIG. 11 is a diagram showing a light emission spectrum of Metal-Complex Compound 16 in the present invention at room temperature.

It was confirmed in accordance with a measurement of light emission spectrum about Metal-Complex Compound 16 obtained, that λ max=545 nm (excitation wavelength: 400 nm) (refer to FIG. 11).

Synthesis Example 15

Synthesis of Metal-Complex Compound 17

As described in the route for synthesis of the above Metal-Complex Compound 14, Metal-Complex Compound 16 in an amount of 0.13 mmol (0.10 g), potassium cyanide in an amount of 0.263 mmol (0.017 g) and ethylene glycol in an amount of 10 milliliter were placed into an eggplant type flask having a capacity of 100 milliliter, and the resultant solution was exposed to microwave irradiation for 3 minutes under the atmospheric nitrogen gas flow, followed by refluxing under heating. After the resultant solution was cooled by leaving it standing, hexafluorophosphate ammonium aqueous solution was added and the generated precipitate was separated by filtration and washed with the use of hexane. The resultant crystals were re-crystallized with the use of acetonitrile/ether, and as a result, orange crystals of Metal-Complex Compound 17 in an amount of 0.055 g were obtained (yield: 56%). It was confirmed in accordance with ESI-MS that the orange crystals were the aimed compound. The result of the measurement in accordance with ESI-MS is shown as the following:

ESI-MS: calcd for IrC$_{27}$H$_{49}$F$_6$N$_4$P=751, found, m/z=751 (100)

Further, in accordance with the Fourier Transform-Infrared spectroscopy (FT-IR) measurement, an existence of cyano group in the aimed compound was confirmed because a peculiar absorption at 2212 cm$^{-1}$ was found.

Figure 12:
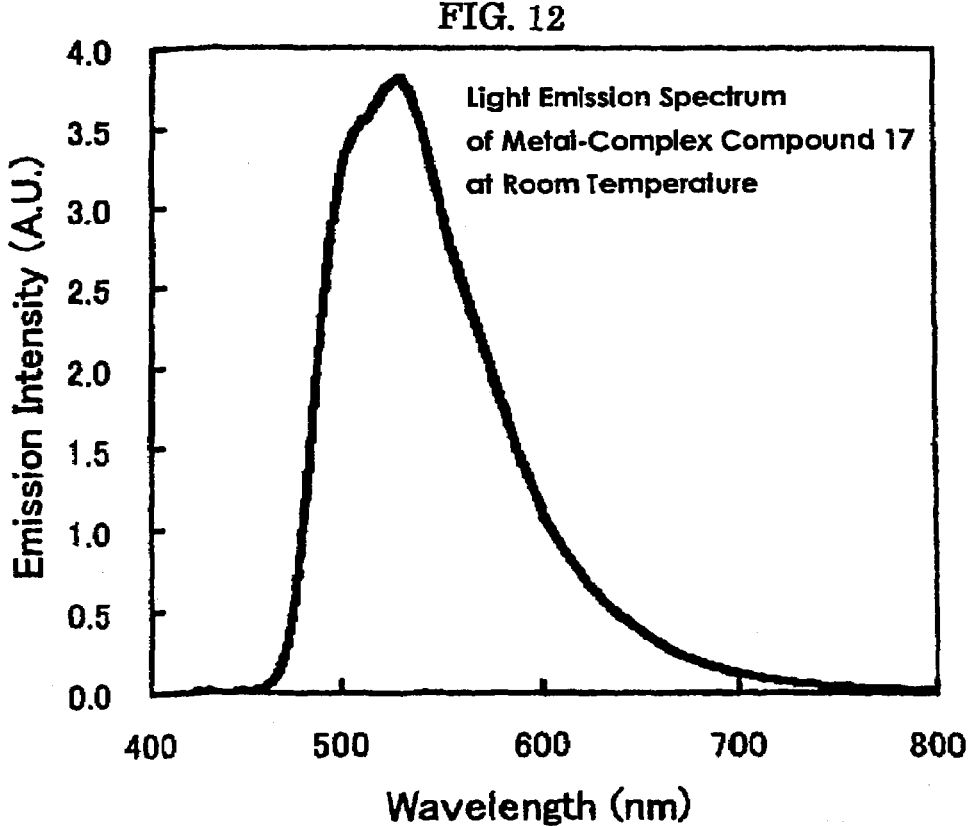
FIG. 12 is a diagram showing a light emission spectrum of Metal-Complex Compound 17 in the present invention at room temperature.

It was confirmed in accordance with a measurement of light emission spectrum about Metal-Complex Compound 17 obtained, that λ max=512 nm (excitation wavelength: 400 nm) (refer to FIG. 12).

Synthesis Example 16

Synthesis of Metal-Complex Compound 85

The route for synthesis of the above Metal-Complex Compound 85 is shown as follows:

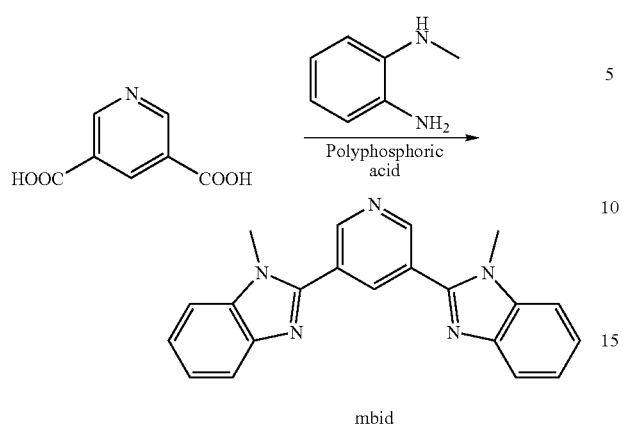

mbid

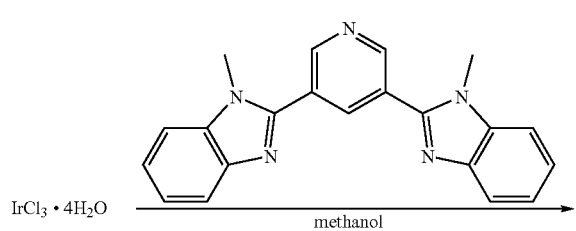

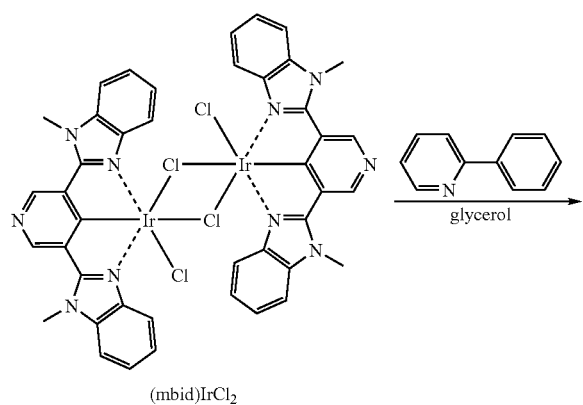

(mbid)IrCl₂

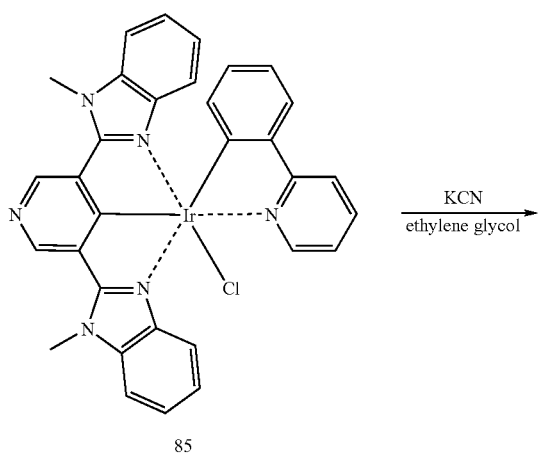

85

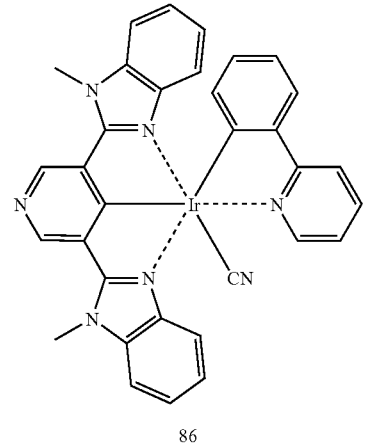

86

(1) Synthesis of mbid

Pyridine 3,5-dicarboxylic acid in an amount of 0.018 mmol (3.0 g), N-methyl-1,2-phenylenediamine in an amount of 0.036 mmol (4.4 g) and polyphosphoric acid in an amount of 35 milliliter were placed into an eggplant type flask having a capacity of 200 milliliter, and the resultant solution was reacted at a temperature of 100° C. for 15 hours and subsequently at a temperature of 200° C. for 11 hours, followed by cooling with leaving it standing. Throwing the reactant into 300 milliliter of pure water, and after neutralizing with the use of 5M sodium hydroxide aqueous solution, the precipitate was separated by filtration. After washing the precipitate with the use of pure water, it was dissolved into methanol bleached with the use of activated carbon, and then, adding pure water, white crystals of the aimed substance in an amount of 5.9 g were obtained yield: 97%).

(2) Synthesis of (mbid)IrCl₂

Iridic chloride in an amount of 1.07 mmol (0.4 g), mbid in an amount of 2.18 mmol (0.74 g) and methanol in an amount of 40 milliliter were placed into an eggplant type flask having a capacity of 100 milliliter, and the resultant solution was refluxed with heating for 6 hours under the atmospheric nitrogen gas flow. After the resultant solution was cooled by leaving it standing, the precipitate was collected by filtration and as a result, yellowish ocher crystals as the aimed substance were obtained (yield: 96%).

(3) Synthesis of Metal-Complex Compound 85

Into an eggplant type flask having a capacity of 100 milliliter, (mbid) IrCl₂ in an amount of 0.083 mmol (0.1 g), 2-phenyl pyridine in an amount of 0.166 mmol (0.026 g) and glycerin in an amount of 20 milliliter were placed, and the resultant solution was exposed to microwave irradiation for 5 minutes under an atmospheric nitrogen gas flow, followed by refluxing under heating. After the resultant solution was cooled by leaving it standing, 0.200 milliliter of pure water was added and the resultant mixture was extracted with the use of methylene chloride in an amount of 250 milliliter. After removing the solvent from an organic layer by pressure reduction, 20 milliliter of pure water was added, and the generated precipitate was collected by filtration, and as a result of washing with the use of ether, orange crystals of the aimed substance in an amount of 0.074 g was obtained (yield: 62%). It was confirmed in accordance with ESI-MS that the orange crystals were the aimed compound. The result of the measurement in accordance with ESI-MS is shown as the following:

ESI-MS: calcd for $IrC_{32}H_{24}ClN_6$=720, found, m/z=720 (100)

Synthesis Example 17

Synthesis of Metal-Complex Compound 86

As described in the route for synthesis of the above Metal-Complex Compound 16, Metal-Complex Compound 85 in an amount of 0.22 mmol (0.16 g), potassium cyanide in an amount of 0.14 mmol (0.028 g) and ethylene glycol in an amount of 20 milliliter were placed into an eggplant type flask having a capacity of 100 milliliter, and the resultant solution was exposed to microwave irradiation for 3 minutes under the atmospheric nitrogen gas flow, followed by refluxing under heating. After the resultant solution was cooled by leaving it standing, 70 milliliter of pure water was added and the resultant mixture was extracted with the use of methylene chloride in an amount of 150 milliliter. After removing the solvent from an organic layer by pressure reduction, 0.20 milliliter of pure water was added, and the generated precipitate was collected by filtration, and washed with the use of ether. Impurities were removed with the use of methylene chloride and as a result, yellow crystals as the aimed substance in an amount of 0.089 g were obtained (yield: 56%). It was confirmed in accordance with ESI-Ms that the yellow crystals were the aimed compound. The result of the measurement in accordance with ESI-MS is shown as the following:

ESI-MS: calcd for $IrC_{88}H_{24}N_7$=710, found, m/z=710 (100)

Further, in accordance with the FT-IR measurement, an existence of cyano group in the aimed compound was confirmed because a peculiar absorption at 2204 $cm^{-1}$ was found.

Figure 13:
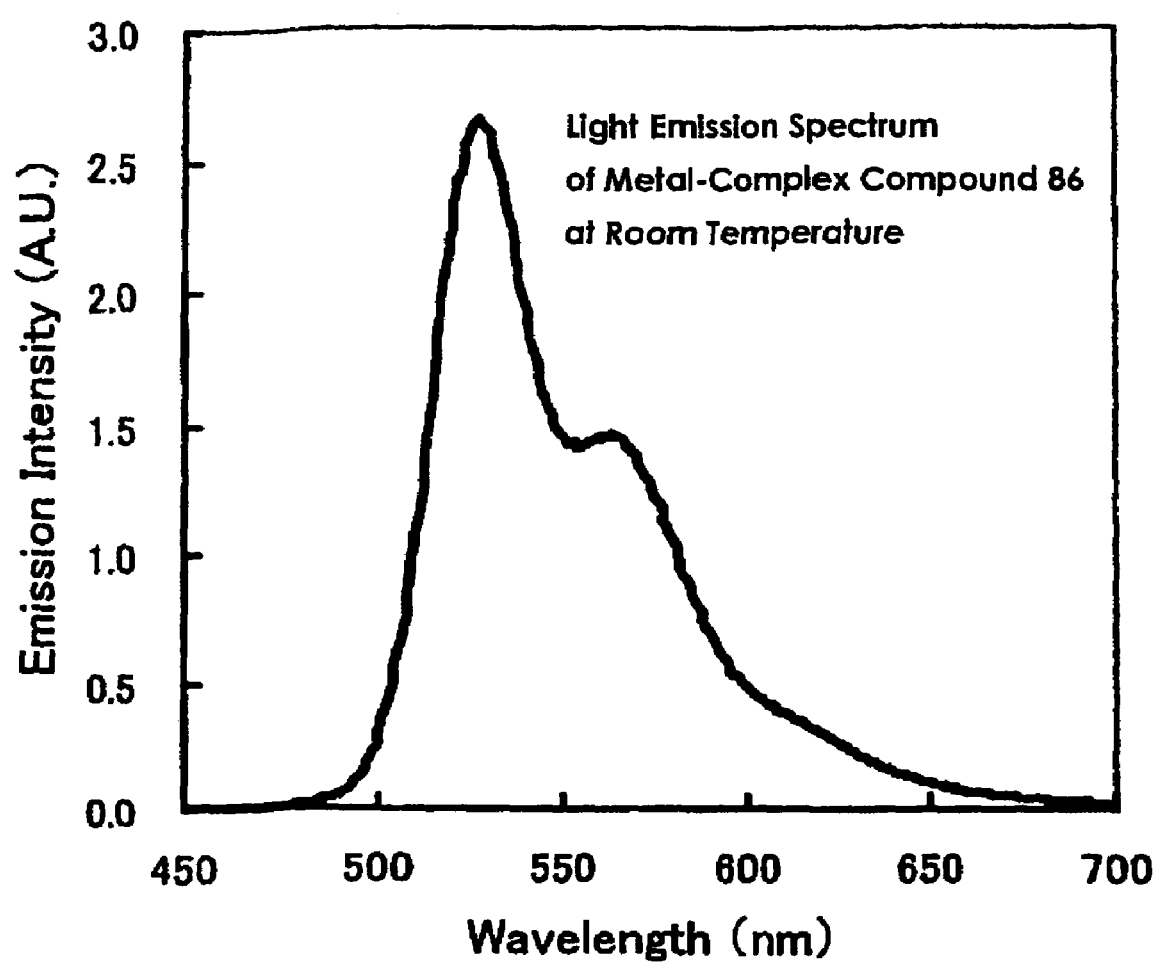
FIG. 13 is a diagram showing a light emission spectrum of Metal-Complex Compound 86 in the present invention at room temperature.

It was confirmed in accordance with a measurement of light emission spectrum about Metal-Complex Compound 86 obtained, that λ max=524 nm (excitation wavelength: 400 nm) (refer to FIG. 13).

Physical properties about phosphorus photoluminescence of the synthesized complex are shown in Table 1 below. In comparison with known $Ir(ppy)_3$ (Compound A), all the synthesized complex have greater values in either $K_r$ (radiation velocity) or $K_{nr}$ (non-radiation velocity). Therefore, it verifies that the values of phosphorus light quantum yield fall within a range of 0.63 to 0.86, which is excitingly great.

TABLE 1

| Synthesis Example | Metal-Complex Compound | Phosphorus light quantum yield | $K_r (10^5 s^{-1})$ | $K_{nr} (10^5 s^{-1})$ |
|---|---|---|---|---|
| 1 | 5 | 0.63 | 5.25 | 3.08 |
| 2 | 6 | 0.84 | 3.87 | 0.74 |
| 5 | 124 | 0.86 | 5.28 | 0.86 |
| 6 | 7 | 0.85 | 3.40 | 0.60 |
| 7 | 103 | 0.77 | 5.50 | 1.64 |
| 11 | 105 | 0.75 | 5.14 | 1.71 |
| Reference Example | fac-$Ir(ppy)_3$X | 0.40 | 2.1 | 3.2 |

XM. E. Thompson et. al., J. Am. Chem. Soc., 125, 7377 (2003)

Example 1

Fabrication of Organic EL Device

A glass substrate (manufactured by GEOMATEC Company) of 25 mm×75 mm×1.1 mm thickness having an ITO transparent electrode was cleaned by application of ultrasonic wave in isopropyl alcohol for 5 minutes and then by exposure to ozone generated by ultraviolet light for 30 minutes. On the substrate, a film of polyethylene dihydroxy thiophene (PEDOT) for the use of the hole injecting layer with film thickness of 100 nm was formed in accordance with a spin coating process and then, a chloroform solution having a concentration of 0.5% by weight prepared by mixing Metal-Complex Compound 6 synthesized in Synthesis Example 2 in an amount of 7% by weight to Host Material H below and dissolved into a chloroform solvent made by bubbling nitrogen gas for 15 minutes under the same atmosphere was applied over PEDOT by means of a spin coating process to form a film. The coated film worked as a light emitting layer. The film thickness was 60 nm. On the film formed above, a film of BAlq below having a thickness 25 nm was formed. The formed film of BAlq worked as the hole barrier layer. On the film formed above, a film of Alq having a thickness 5 nm was formed. The film of Alq worked as the electron injecting layer. Subsequently, lithium fluoride was deposited up to 0.1 nm in thickness and then, aluminum was deposited up to 150 nm in thickness. The Al/LiF worked as a cathode. An organic EL device was fabricated in the manner described above.

The device fabricated above was sealed and examined by passing electric current. Green light was emitted at a luminance of 102 $cd/m^2$ under a voltage of 7.9 V and a current density of 0.68 $mA/cm^2$. The CIE chromaticity coordinates were (0.28, 0.63), and the current efficiency was 15.0 cd/A.

Host Material H

BAlq

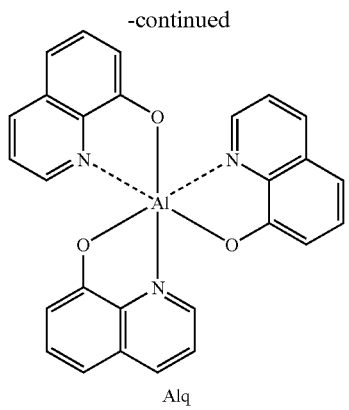

Alq

Comparative Example 1

An organic EL device was fabricated similarly as Example 1 except that the following Metal-Complex Compound D below described in publicly known literature Inog. Chem., 6513 (2004) was used instead of Metal-Complex Compound 6. The device fabricated above was sealed and examined by passing electric current. Orange light was emitted at a luminance of 101 cd/m² under a voltage of 8.8 V and a current density of 0.68 mA/cm². The CIE chromaticity coordinates were (0.51, 0.48), and the current efficiency was 6.5 cd/A.

Metal-Complex Compound D

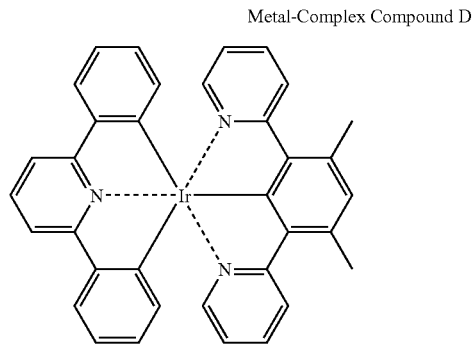

As the foregoing description, despite employing the same central metal and the tridentate chelate ligand, a case in the present invention where a metal-complex compound with the optimized ligand structure reduces the wavelength of light emission shorter, and provides an organic EL device of an enhanced current efficiency.

INDUSTRIAL APPLICABILITY

As described above in detail, the present invention provides an organic EL device which emits blue light with high purity and of short wavelength with an enhanced current efficiency. Accordingly, the present invention is applicable for a field such as various display devices, display panels, backlights, illuminating light sources, beacon lights, signboards, and interior designs, particularly suitable as display device for color displays.

What is claimed is:

1. A neutral metal-complex compound which comprises a tridentate chelate ligand having a partial structure represented by a following general formula (I):

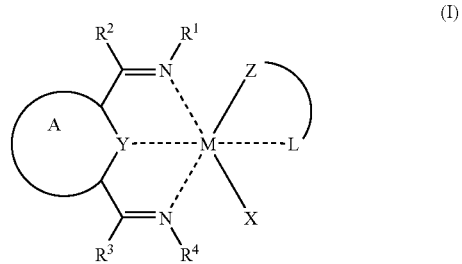

wherein M represents any one metal atom of Group 9 in Periodic Table;

L—Z represents an organic group expressed by N(nitrogen)-C(carbon) or O(oxygen)-O(oxygen);

X represents a monovalent ligand having an atom of Groups 14 to 17 in Periodic Table;

Y represents a carbon atom;

A represents a cycloalkane moiety having 5 to 20 carbon atoms and further may have a substituent, an aromatic hydrocarbon group having 6 to 20 carbon atoms and further may have a substituent or a heterocyclic group having 2 to 20 carbon atoms and further may have a substituent indicating that a circle enclosing the sign A shows a ring structure comprising Y;

$R^1$ to $R^4$ each independently represents a hydrogen atom, a cyano group, a halogen atom, an alkyl group having 1 to 12 carbon atoms and further may have a substituent, an alkylamino group having 1 to 12 carbon atoms and further may have a substituent, an arylamino group having 6 to 20 carbon atoms and further may have a substituent, an alkoxy group having 1 to 12 carbon atoms and further may have a substituent, an alkoxy halide group having 1 to 12 carbon atoms and further may have a substituent, an aryloxy group having 6 to 20 carbon atoms and further may have a substituent, an aromatic hydrocarbon group having 6 to 20 carbon atoms and further may have a substituent, a heterocyclic group having 3 to 20 carbon atoms and further may have a substituent, an alkyl halide group having 1 to 12 carbon atoms and further may have a substituent, an alkenyl group having 1 to 12 carbon atoms and further may have a substituent, an alkynyl group having 1 to 12 carbon atoms and further may have a substituent or a cycloalkyl groups having 1 to 12 carbon atoms and further may have a substituent; and $R^1$ & $R^2$ or $R^3$ & $R^4$ may bond each other to form a ring structure.

2. The metal-complex compound according to claim 1, wherein X in the general formula (I) is a cyano group, a chlorine atom, a bromine atom or an iodine atom.

3. The metal-complex compound according to claim 1, wherein M in the general formula (I) is an iridium atom.

4. The metal-complex compound according to claim 1, wherein said tridentate chelate ligand in the general formula (I) is any one of compounds shown by following general formulae (1), (3), (10)-(12), (14), and (20):

(1)
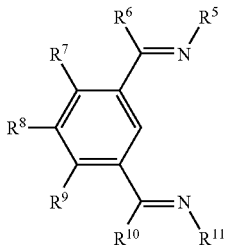

(3)
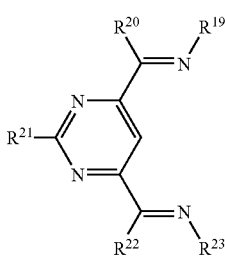

(10)
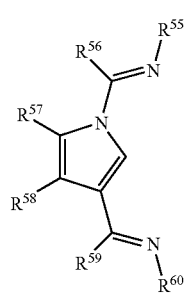

(11)
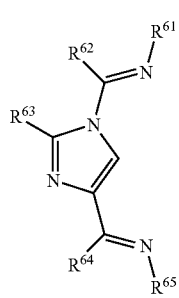

(12)
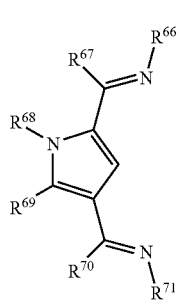

(14)
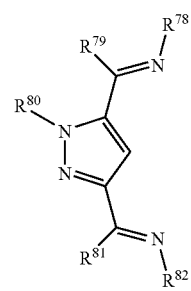

(20)
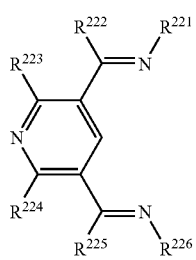

wherein $R^5$ to $R^{98}$ and $R^{207}$ to $R^{232}$ each independently represents a hydrogen atom, a cyano group, a halogen atom, an alkyl group having 1 to 12 carbon atoms and further may have a substituent, an alkylamino group having 1 to 12 carbon atoms and further may have a substituent, an arylamino group having 6 to 20 carbon atoms and further may have a substituent, an alkoxy group having 1 to 12 carbon atoms and further may have a substituent, an alkoxy halide group having 1 to 12 carbon atoms and further may have a substituent, an aryloxy group having 6 to 20 carbon atoms and further may have a substituent, an aromatic hydrocarbon group having 6 to 20 carbon atoms and further may have a substituent, a heterocyclic group having 3 to 20 carbon atoms and further may have a substituent, an alkyl halide group having 1 to 12 carbon atoms and further may have a substituent, an alkenyl group having 1 to 12 carbon atoms and further may have a substituent, an alkynyl group having 1 to 12 carbon atoms and further may have a substituent or a cycloalkyl groups having 1 to 12 carbon atoms and further may have a substituent; wherein $R^5$ to $R^{98}$ and $R^{207}$ to $R^{232}$ each independently exists two or more allowing that $R^5$ to $R^{98}$ and $R^{207}$ to $R^{232}$ each are the same with or different from each other; and each adjacent couple among $R^5$ to $R^{98}$ and $R^{207}$ to $R^{232}$ may bond each other to form a ring structure.

5. The metal-complex compound according to claim 1, wherein said tridentate chelate ligand in the general formula (I) is any one of compounds shown by following general formulae (22), (24), (26), (29), and (30):

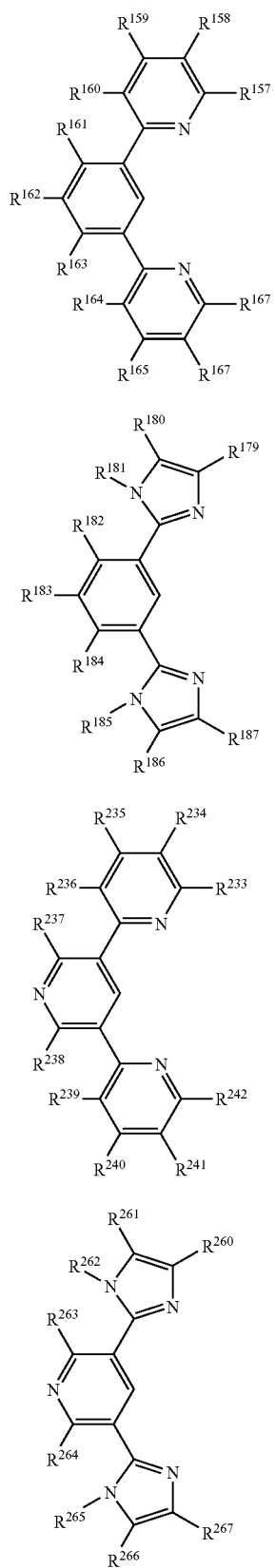

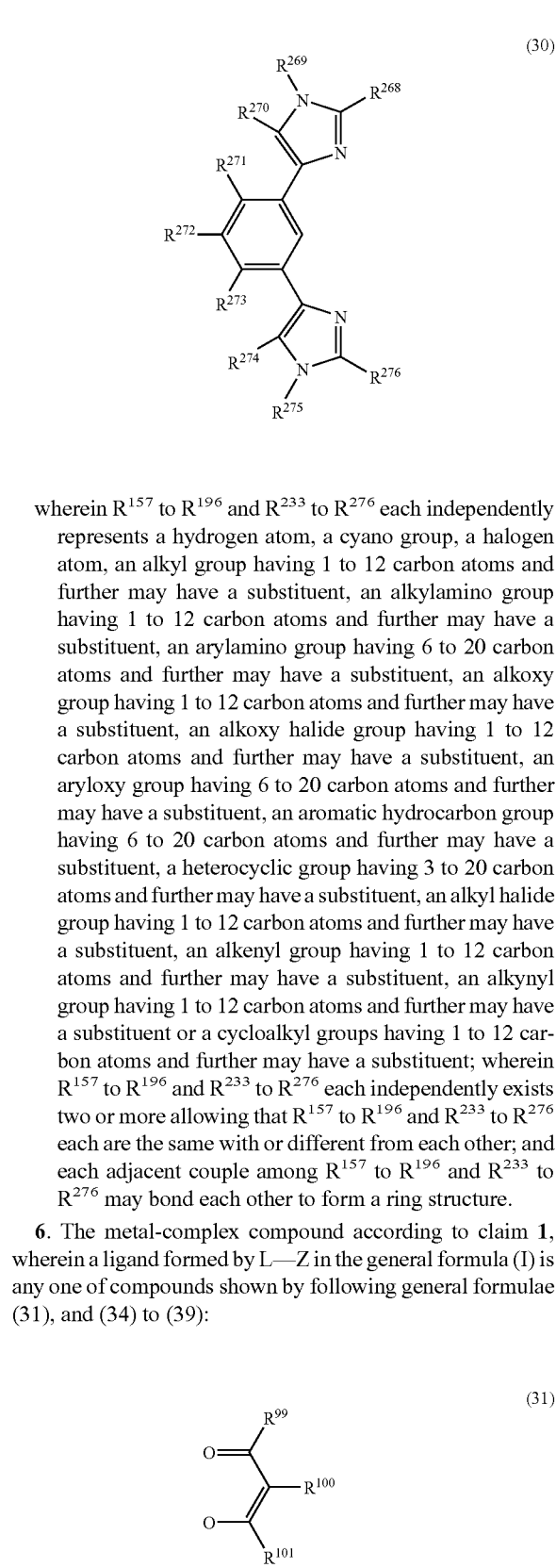

wherein $R^{157}$ to $R^{196}$ and $R^{233}$ to $R^{276}$ each independently represents a hydrogen atom, a cyano group, a halogen atom, an alkyl group having 1 to 12 carbon atoms and further may have a substituent, an alkylamino group having 1 to 12 carbon atoms and further may have a substituent, an arylamino group having 6 to 20 carbon atoms and further may have a substituent, an alkoxy group having 1 to 12 carbon atoms and further may have a substituent, an alkoxy halide group having 1 to 12 carbon atoms and further may have a substituent, an aryloxy group having 6 to 20 carbon atoms and further may have a substituent, an aromatic hydrocarbon group having 6 to 20 carbon atoms and further may have a substituent, a heterocyclic group having 3 to 20 carbon atoms and further may have a substituent, an alkyl halide group having 1 to 12 carbon atoms and further may have a substituent, an alkenyl group having 1 to 12 carbon atoms and further may have a substituent, an alkynyl group having 1 to 12 carbon atoms and further may have a substituent or a cycloalkyl groups having 1 to 12 carbon atoms and further may have a substituent; wherein $R^{157}$ to $R^{196}$ and $R^{233}$ to $R^{276}$ each independently exists two or more allowing that $R^{157}$ to $R^{196}$ and $R^{233}$ to $R^{276}$ each are the same with or different from each other; and each adjacent couple among $R^{157}$ to $R^{196}$ and $R^{233}$ to $R^{276}$ may bond each other to form a ring structure.

6. The metal-complex compound according to claim 1, wherein a ligand formed by L—Z in the general formula (I) is any one of compounds shown by following general formulae (31), and (34) to (39):

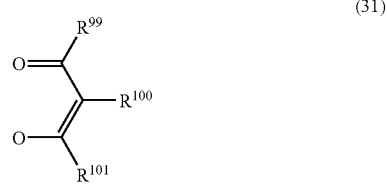

(34)
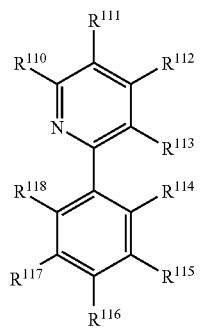

(35)
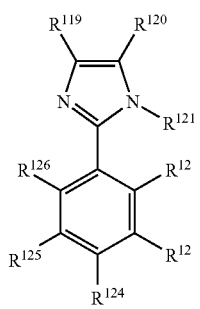

(36)
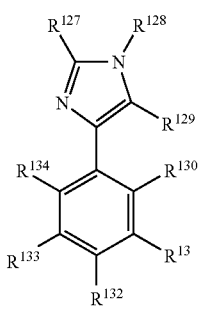

(37)
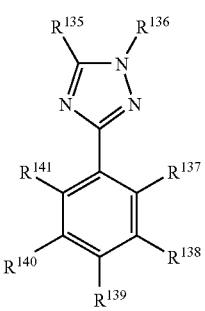

(38)
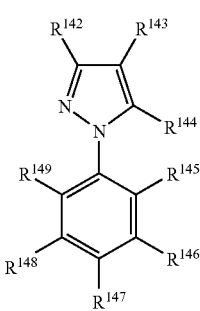

(39)
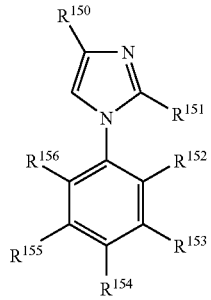

wherein $R^{99}$ to $R^{156}$ each independently represents a hydrogen atom, a cyano group, a halogen atom, an alkyl group having 1 to 12 carbon atoms and further may have a substituent, an alkylamino group having 1 to 12 carbon atoms and further may have a substituent, an arylamino group having 6 to 20 carbon atoms and further may have a substituent, an alkoxy group having 1 to 12 carbon atoms and further may have a substituent, an alkoxy halide group having 1 to 12 carbon atoms and further may have a substituent, an aryloxy group having 6 to 20 carbon atoms and further may have a substituent, an aromatic hydrocarbon group having 6 to 20 carbon atoms and further may have a substituent, a heterocyclic group having 3 to 20 carbon atoms and further may have a substituent, an alkyl halide group having 1 to 12 carbon atoms and further may have a substituent, an alkenyl group having 1 to 12 carbon atoms and further may have a substituent, an alkynyl group having 1 to 12 carbon atoms and further may have a substituent or a cycloalkyl groups having 1 to 12 carbon atoms and further may have a substituent; wherein $R^{99}$ to $R^{156}$ each independently exists two or more allowing that $R^{99}$ to $R^{156}$ each are the same with or different from each other; and each adjacent couple among $R^{99}$ to $R^{156}$ may bond each other to form a ring structure.

7. The metal-complex compound according to claim 1, which is shown by any one of following general formulae (I-1) to (I-9):

(I-1)
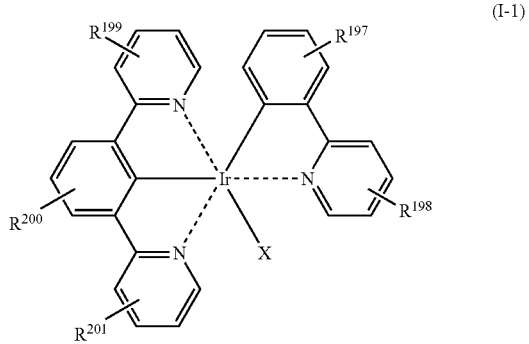

-continued
(I-2)
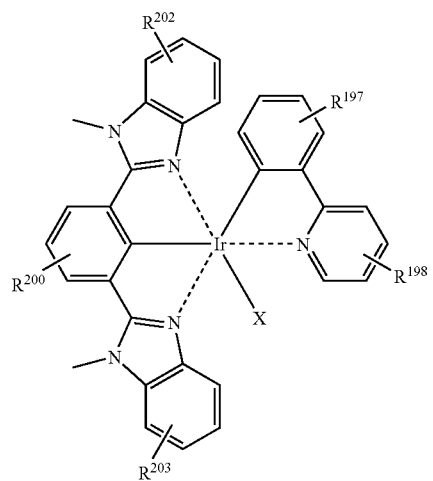
(I-3)
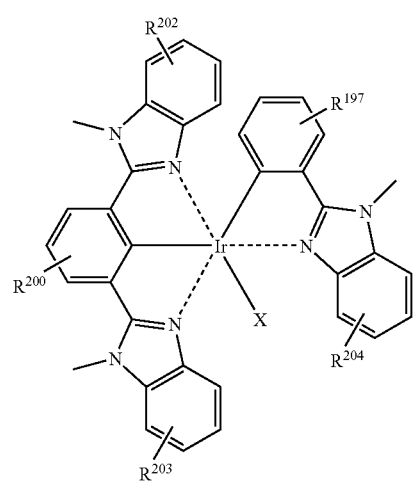
(I-4)
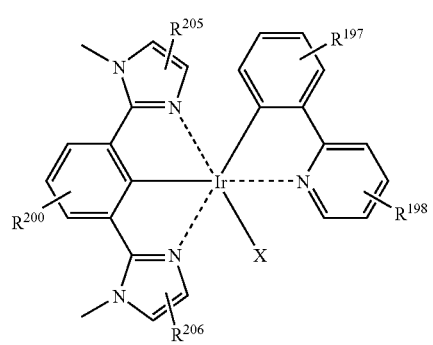
-continued
(I-5)
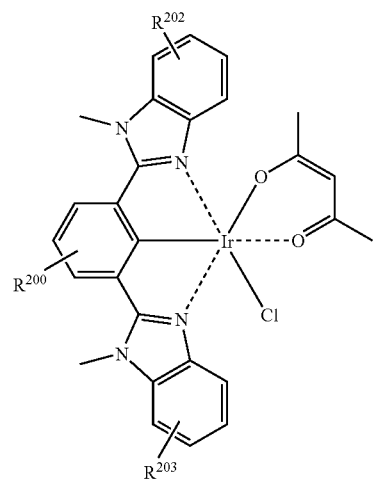
(I-6)
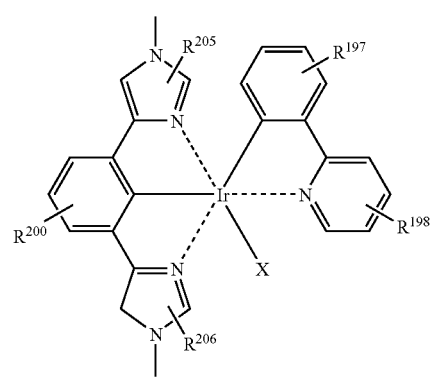
(I-7)
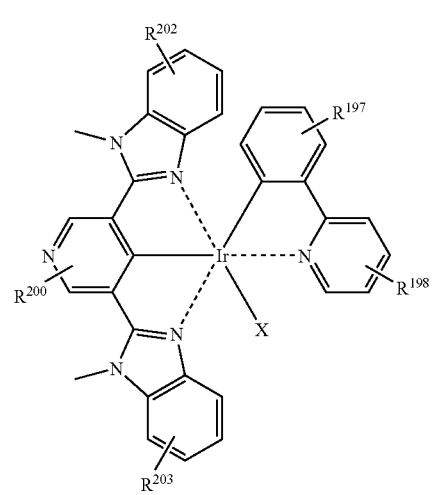

-continued

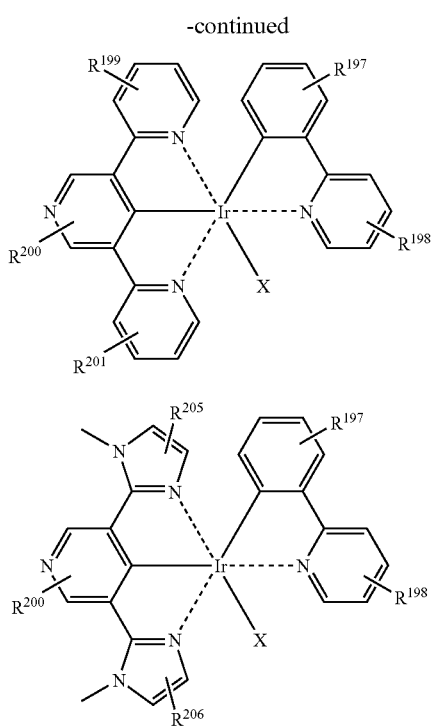

(I-8)

(I-9)

wherein $R^{197}$ to $R^{206}$ each independently represents a hydrogen atom, a cyano group, a halogen atom, an alkyl group having 1 to 12 carbon atoms and further may have a substituent, an alkylamino group having 1 to 12 carbon atoms and further may have a substituent, an arylamino group having 6 to 20 carbon atoms and further may have a substituent, an alkoxy group having 1 to 12 carbon atoms and further may have a substituent, an alkoxy halide group having 1 to 12 carbon atoms and further may have a substituent, an aryloxy group having 6 to 20 carbon atoms and further may have a substituent, an aromatic hydrocarbon group having 6 to 20 carbon atoms and further may have a substituent, a heterocyclic group having 3 to 20 carbon atoms and further may have a substituent, an alkyl halide group having 1 to 12 carbon atoms and further may have a substituent, an alkenyl group having 1 to 12 carbon atoms and further may have a substituent, an alkynyl group having 1 to 12 carbon atoms and further may have a substituent or a cycloalkyl groups having 1 to 12 carbon atoms and further may have a substituent; wherein $R^{197}$ to $R^{206}$ each independently exists two or more allowing that $R^{197}$ to $R^{206}$ each are the same with or different from each other; and each adjacent couple among $R^{197}$ to $R^{206}$ may bond each other to form a ring structure.

8. An organic electroluminescence device which comprises at least one organic thin film layer sandwiched between a pair of electrode consisting of an anode and a cathode, wherein the organic thin film layer comprises the metal-complex compound according to any one of claims 1 and 2-7, which emits light by applying an electric voltage between the pair of electrode.

9. The organic electroluminescence device according to claim 8, wherein said metal-complex compound is contained in a light emitting layer.

10. The organic electroluminescence device according to claim 9, which emits bluish light.

11. The organic electroluminescence device according to claim 8, wherein said organic thin film layer comprising the metal-complex compound is formed by coating.

* * * * *